US007176289B1

United States Patent
Daniel et al.

(10) Patent No.: US 7,176,289 B1
(45) Date of Patent: Feb. 13, 2007

(54) MODULATION OF ENDOTHELIAL CELL SURFACE RECEPTOR ACTIVITY IN THE REGULATION OF ANGIOGENESIS

(75) Inventors: Thomas O. Daniel, Nashville, TN (US); Takamune Takahashi, Nashville, TN (US); Raymond Mernaugh, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/516,728

(22) Filed: Mar. 1, 2000

Related U.S. Application Data

(63) Continuation-in-part of application No. 09/152,160, filed on Sep. 11, 1998, now Pat. No. 6,248,327.

(51) Int. Cl.
*C07K 16/00* (2006.01)
*C12P 21/08* (2006.01)

(52) U.S. Cl. ................... 530/388.1; 530/387.1
(58) Field of Classification Search ............. 424/130.1, 424/143.1, 146.1, 139.1, 133.1, 152.1, 156.1; 530/388.22, 388.85
See application file for complete search history.

(56) References Cited

U.S. PATENT DOCUMENTS

| 5,595,911 | A | 1/1997 | Tonks |
| 5,660,827 | A | 8/1997 | Thorpe et al. |
| 5,733,876 | A | 3/1998 | O'Reilly et al. |
| 5,753,230 | A | 5/1998 | Brooks et al. |
| 5,762,918 | A | 6/1998 | Thorpe |
| 5,766,591 | A | 6/1998 | Brooks et al. |
| 5,776,427 | A | 7/1998 | Thorpe et al. |
| 5,863,781 | A | 1/1999 | Tonks |
| 6,114,140 | A | 9/2000 | Tonks et al. |
| 6,552,169 | B1 | 4/2003 | Tonks et al. ............ 530/350 |

FOREIGN PATENT DOCUMENTS

| EP | 0520029 B1 | 5/1995 |
| EP | 708831 | 5/1995 |
| WO | WO91/13989 A1 | 9/1991 |
| WO | WO95/30008 A1 | 11/1995 |
| WO | WO98/04712 A1 | 2/1998 |
| WO | WO98/04712 A3 | 3/1998 |
| WO | WO99/02704 A1 | 1/1999 |
| WO | WO00/15258 A | 3/2000 |

OTHER PUBLICATIONS

Kung HF et al (Zhongguo Yi Xue Ke Xue Yuan Xue Bao. Feb. 2001;23(1):2-7—Abstract Only.*
Takahashi et al., "Glomerular Endothelial Localization of Receptor Tyrosine Phosphatase," Journal of the American Society of Nephrology, vol. 9, p. 368A, (Sep., 1998).—Abstract only.
PCT International Search Report for corresponding PCT application No. PCT/US99/19965.
Takahashi et al., "Endothelial Cell Receptor Tyrosine Phosphatase/Density Enhanced Phosphatase-1, ECRTP/DEP-1, is an Oligomerization Responsive Angiostatic Switch," The FASEB Journal, vol. 13 (No. 5), p. A694, (Mar. 15, 1999).
De La Fuente-Garcia et al., "CD148 is a Membrane Protein Turosine Phosphatase Present in All Hematopoietic Lineages and is Involved in Signal Transduction on Lymphocytes," Blood, vol. 91 (No. 8), p. 2800-2809, (Apr. 15, 1998).
Tangye et al., "CD148: a Receptor-Type Protein Tyrosine Phosphatase Involved in the Regulation of Human T Cell Activation," The Journal of Immunology, vol. 161 (No. 7), p. 3249-3255, (Oct. 1, 1998).
Takahashi et al., "Endothelial Localization of Receptor Tyrosine Phosphatase, ECRTP/DEP-1, Developing and Mature Renal Vasculature," The Journal of the American Society of Nephrology, vol. 10 (No. 10), p. 2135-2145, (1999).
Stockinger et al., "New Human Leukocyte Clusters of Differentiation," Transfusion, vol. 38 (No. 5), p. 499-505, (1998).
Angel de la Fuente-Garcia et al., CD148 Is a Membrane Protein Tyrosine Phosphatase Present in All Hematopoietic Lineages and is Involved in Signal Transduction on Lymphocytes, *Blood* 91(8):2800-2809 (Apr. 15, 1998.
Jallal et al., The Receptor-like Protein-tyrosine Phosphatase DEP-1 is Constitutively Associated with a 64-kDa Protein Serine/Threonine Kinase, *J. of Biological Chemistry* 272(18):12158-12163 (May 2, 1997).
Takahashi et al., Endothelial Localization of Receptor Tyrosine Phosphatase, ECRTP/DEP-1, in Developing and Mature Renal Vasculature, *J. Am. Soc. Nephrol.* 10:2135-2145 (1999).
Kishimoto et al., Leucocyte Typing VI: White Cell Differentiation Antigens, *Proceedings of the Sixth International Workshop and Conference, Kobe, Japan* (Nov. 10-14, 1996).

(Continued)

*Primary Examiner*—Christopher Yaen
(74) *Attorney, Agent, or Firm*—Jenkins, Wilson, Taylor & Hunt, P.A.

(57) ABSTRACT

A method of modulating angiogenesis in a vertebrate subject, the method comprising administering to the vertebrate subject an ECRTP/DEP-1 activity-modulating amount of a composition, whereby an ECRTP/DEP-1 within the vertebrate subject is contacted by the composition; and modulating angiogenesis through the contacting of the ECRTP/DEP-1 with the composition. Optionally, the composition includes a monoclonal antibody which preferentially binds ECRTP/DEP-1. Methods for screening for modulators of ECRTP/DEP-1 are also disclosed.

10 Claims, 14 Drawing Sheets

OTHER PUBLICATIONS

Product Analysis Sheet, Mouse(monoclonal) Anti-Human CD148 Unconjugated *Biosource* (Undated).

del Pozo et al., Expression on human eosinophils of CD148: a membrane tyrosine phosphatase. Implications in the effector function of eosinophils, *J. of Leukocyte Biology* 68:31-37 (Jul. 2000).

Hundt et al., Functional characterization of receptor-type protein tyrosine phosphatase CD148 (HPTP eta/DEP-1) in Fc gamma receptor IIa signal transduction of human neutrophils, *Eur. J. Immunol.* 27(12):3532-3535 (Dec. 1997) (ABSTRACT).

Tangye et al., CD148: A Receptor-Type Protein Tyrosine Phosphatase Involed in the Regulation of Human T Cell Activation, *J. of Immunology* 3249-3255 (1998).

IPER for corresponding PCT Appl. No. PCT/US01/06178 dated Oct. 7, 2004.

Honda et al., "Molecular Cloning, Characterization, and Chromosomal Localization of a Novel Protein-Tyrosine Phosphatase, HPTP", Blood, vol. 84, (1994) pp. 4186-4194.

Borges et al., "Cloning and Characterization of Rat Density-Enhanced Phosphatase-1, a Protein Tyrosine Phosphatase Expressed by Vascular Cells", Circulation Research, vol. 79, No. 3, (Sep. 1996) pp. 570-580.

Keane et al., "The Protein Tyrosine Phosphatase DEP-1 is Induced During Differentiation and Inhibits Growth of Breast Cancer Cells", Cancer Research, vol. 56, (Sep. 15, 1996) pp. 4236-4243.

Ostman et al., "Expression of DEP-1, a Receptor-Like Protein-Tyrosine-Phosphatase, is Enhanced with Increasing Cell Density", Proc. Natl. Acad. Sci. USA, vol. 91, (Oct. 1994) pp. 9680-9684.

Memo concerning the Official Action reported in the Covering Letter for Australian Patent Application No. 2001239898 dated May 24, 2005.

International Preliminary Examination Report for corresponding PCT Appl. No. PCT/US01/067178 dated Dec. 7, 2004.

Honda et al., "Molecular Cloning, Characterization, and Chromosomal Localization of a Novel Protein-Tyrosine Phosphatase, HPTP", Blood, vol. 84, (1994) pp. 4186-4194.

Borges et al., "Cloning and Characterization of Rat Density-Enhanced Phosphatase-1, a Protein Tyrosine Phosphatase Expressed by Vascular Cells", Circulation Research, vol. 79, No. 3, (Sep. 1996) pp. 570-580.

Keane et al., "The Protein Tyrosine Phosphatase DEP-1 is Induced During Differentiation and Inhibits Growth of Breast Cancer Cells", Cancer Research, vol. 56, (Sep. 15, 1996) pp. 4236-4243.

Ostman et al., "Expression of DEP-1, a Receptor-Like Protein-Tyrosine-Phosphatase, is Enhanced with Increasing Cell Density", Proc. Natl. Acad. Sci. USA, vol. 91, (Oct. 1994) pp. 9680-9684.

* cited by examiner

Artery

Glomerulus

SEQUENCE LISTING

```
<160> NUMBER OF SEQ ID NOS: 4

<210> SEQ ID NO 1
<211> LENGTH: 8
<212> TYPE: PRT
<213> ORGANISM: Homo sapiens

<400> SEQUENCE: 1

Gln Ser Arg Asp Thr Glu Val Leu
1               5

<210> SEQ ID NO 2
<211> LENGTH: 4
<212> TYPE: PRT
<213> ORGANISM: Artificial
<220> FEATURE:
<223> OTHER INFORMATION: Artifical peptide spacer

<400> SEQUENCE: 2

Leu Ala Leu Ala
1

<210> SEQ ID NO 3
<211> LENGTH: 5117
<212> TYPE: DNA
<213> ORGANISM: Homo sapiens
<220> FEATURE:
<221> NAME/KEY: CDS
<222> LOCATION: (350)..(4363)
<300> PUBLICATION INFORMATION:
<301> AUTHORS: Ostman,A., Yang,Q. and Tonks,N.K.
<302> TITLE: Expression of DEP-1, a receptor-like
      protein-tyrosine-phosphatase, is enhanced with increasing cell
      density
<303> JOURNAL: Proc. Natl. Acad. Sci. U.S.A.
<304> VOLUME: 91
```

```
<305> ISSUE: 21
<306> PAGES: 9680-9684
<307> DATE: 1994-10-11
<308> DATABASE ACCESSION NUMBER: U10886
<309> DATABASE ENTRY DATE: 1994-06-15
<313> RELEVANT RESIDUES: (1)..(5117)

<400> SEQUENCE: 3
ccccagccgc atgacgcgcg gaggaggcag cgggacgagc gcgggagccg ggaccgggta     60
gccgcgcgct gggggtgggc gccgctcgct ccgccccgcg aagcccctgc gcgctcaggg    120
acgcggcccc cccgcggcag ccgcgctagg ctccggcgtg tggccgcggc cgccgccgcg    180
ctgccatgtc tccgggcaag ccggggcggg cggagcgggg acgaggcgga ccggctggcg    240
gaggaggagg cgaaggagac ggcaggaggc ggcgacgacg gtgcccgggc tcgggcgcac    300
ggcggggccc gattcgcgcg tccggggcac gttccaggc gcgcggggc atg aag ccg    358
                                                    Met Lys Pro
                                                      1 gcg gcg cgg gag gcg cgg ctg cct ccg cgc tcg ccc ggg ctg cgc tgg    406
Ala Ala Arg Glu Ala Arg Leu Pro Pro Arg Ser Pro Gly Leu Arg Trp
     5                  10                  15 gcg ctg ccg ctg ctg ctg ctg ctg cgc ctg ggc cag atc ctg tgc         454
Ala Leu Pro Leu Leu Leu Leu Leu Arg Leu Gly Gln Ile Leu Cys
 20                  25                  30                  35 gca ggt ggc acc cct agt cca att cct gac cct tca gta gca act gtt    502
Ala Gly Gly Thr Pro Ser Pro Ile Pro Asp Pro Ser Val Ala Thr Val
             40                  45                  50 gcc aca ggg gaa aat ggc ata acg cag atc agc agt aca gca gaa tcc    550
Ala Thr Gly Glu Asn Gly Ile Thr Gln Ile Ser Ser Thr Ala Glu Ser
         55                  60                  65 ttt cat aaa cag aat gga act gga aca cct cag gtg gaa aca aac acc    598
Phe His Lys Gln Asn Gly Thr Gly Thr Pro Gln Val Glu Thr Asn Thr
     70                  75                  80 agt gag gat ggt gaa agc tct gga gcc aac gat agt tta aga aca cct    646
Ser Glu Asp Gly Glu Ser Ser Gly Ala Asn Asp Ser Leu Arg Thr Pro
 85                  90                  95 gaa caa gga tct aat ggg act gat ggg gca tct caa aaa act ccc agt    694
Glu Gln Gly Ser Asn Gly Thr Asp Gly Ala Ser Gln Lys Thr Pro Ser
100                 105                 110                 115 agc act ggg ccc agt cct gtg ttt gac att aaa gct gtt tcc atc agt    742
Ser Thr Gly Pro Ser Pro Val Phe Asp Ile Lys Ala Val Ser Ile Ser
             120                 125                 130 cca acc aat gtg atc tta act tgg aaa agt aat gac aca gct gct tct    790
Pro Thr Asn Val Ile Leu Thr Trp Lys Ser Asn Asp Thr Ala Ala Ser
         135                 140                 145 gag tac aag tat gta gta aag cat aag atg gaa aat gag aag aca att    838
Glu Tyr Lys Tyr Val Val Lys His Lys Met Glu Asn Glu Lys Thr Ile
     150                 155                 160 act gtt gtg cat caa cca tgg tgt aac atc aca ggc tta cgt cca gcg    886
Thr Val Val His Gln Pro Trp Cys Asn Ile Thr Gly Leu Arg Pro Ala
165                 170                 175 act tca tat gta ttc tcc atc act cca gga ata ggc aat gag act tgg    934
Thr Ser Tyr Val Phe Ser Ile Thr Pro Gly Ile Gly Asn Glu Thr Trp
180                 185                 190                 195 gga gat ccc aga gtc ata aaa gtc atc aca gag ccg atc cca gtt tct    982
Gly Asp Pro Arg Val Ile Lys Val Ile Thr Glu Pro Ile Pro Val Ser
             200                 205                 210 gat ctc cgt gtt gcc ctc acg ggt gtg agg aag gct gct ctc tcc tgg   1030
Asp Leu Arg Val Ala Leu Thr Gly Val Arg Lys Ala Ala Leu Ser Trp
         215                 220                 225
```

```
                                      -continued agc aat ggc aat ggc acc gcc tcc tgc cgg gtt ctt ctt gaa agc att    1078
Ser Asn Gly Asn Gly Thr Ala Ser Cys Arg Val Leu Leu Glu Ser Ile
        230                 235                 240 gga agc cat gag gag ttg act caa gac tca aga ctt cag gtc aat atc    1126
Gly Ser His Glu Glu Leu Thr Gln Asp Ser Arg Leu Gln Val Asn Ile
245                 250                 255 tcg gac ctg aag cca ggg gtt caa tac aac atc aac ccg tat ctt cta    1174
Ser Asp Leu Lys Pro Gly Val Gln Tyr Asn Ile Asn Pro Tyr Leu Leu
260                 265                 270                 275 caa tca aat aag aca aag gga gac ccc ttg ggc aca gaa ggt ggc ttg    1222
Gln Ser Asn Lys Thr Lys Gly Asp Pro Leu Gly Thr Glu Gly Gly Leu
            280                 285                 290 gat gcc agc aat aca gag aga agc cgg gca ggg agc ccc acc gcc cct    1270
Asp Ala Ser Asn Thr Glu Arg Ser Arg Ala Gly Ser Pro Thr Ala Pro
                295                 300                 305 gtg cat gat gag tcc ctc gtg gga cct gtg gac cca tcc tcc ggc cag    1318
Val His Asp Glu Ser Leu Val Gly Pro Val Asp Pro Ser Ser Gly Gln
            310                 315                 320 cag tcc cga gac acg gaa gtc ctg ctt gtc ggg tta gag cct ggc acc    1366
Gln Ser Arg Asp Thr Glu Val Leu Leu Val Gly Leu Glu Pro Gly Thr
325                 330                 335 cga tac aat gcc acc gtt tat tcc caa gca gcg aat ggc aca gaa gga    1414
Arg Tyr Asn Ala Thr Val Tyr Ser Gln Ala Ala Asn Gly Thr Glu Gly
340                 345                 350                 355 cag ccc cag gcc ata gag ttc agg aca aat gct att cag gtt ttt gac    1462
Gln Pro Gln Ala Ile Glu Phe Arg Thr Asn Ala Ile Gln Val Phe Asp
            360                 365                 370 gtc acc gct gtg aac atc agt gcc aca agc ctg acc ctg atc tgg aaa    1510
Val Thr Ala Val Asn Ile Ser Ala Thr Ser Leu Thr Leu Ile Trp Lys
                375                 380                 385 gtc agc gat aac gag tcg tca tct aac tat acc tac aag ata cat gtg    1558
Val Ser Asp Asn Glu Ser Ser Ser Asn Tyr Thr Tyr Lys Ile His Val
            390                 395                 400 gcg ggg gag aca gat tct tcc aat ctc aac gtc agt gag cct cgc gct    1606
Ala Gly Glu Thr Asp Ser Ser Asn Leu Asn Val Ser Glu Pro Arg Ala
405                 410                 415 gtc atc ccc gga ctc cgc tcc agc acc ttc tac aac atc aca gtg tgt    1654
Val Ile Pro Gly Leu Arg Ser Ser Thr Phe Tyr Asn Ile Thr Val Cys
420                 425                 430                 435 cct gtc cta ggt gac atc gag ggc acg ccg ggc ttc ctc caa gtg cac    1702
Pro Val Leu Gly Asp Ile Glu Gly Thr Pro Gly Phe Leu Gln Val His
            440                 445                 450 acc ccc cct gtt cca gtt tct gac ttc cga gtg aca gtg gtc agc acg    1750
Thr Pro Pro Val Pro Val Ser Asp Phe Arg Val Thr Val Val Ser Thr
                455                 460                 465 acg gag atc ggc tta gca tgg agc agc cat gat gca gaa tca ttt cag    1798
Thr Glu Ile Gly Leu Ala Trp Ser Ser His Asp Ala Glu Ser Phe Gln
            470                 475                 480 atg cat atc aca cag gag gga gct ggc aat tct cgg gta gaa ata acc    1846
Met His Ile Thr Gln Glu Gly Ala Gly Asn Ser Arg Val Glu Ile Thr
485                 490                 495 acc aac caa agt att atc att ggt ggc ttg ttc cct gga acc aag tat    1894
Thr Asn Gln Ser Ile Ile Ile Gly Gly Leu Phe Pro Gly Thr Lys Tyr
500                 505                 510                 515 tgc ttt gaa ata gtt cca aaa gga cca aat ggg act gaa ggg gca tct    1942
Cys Phe Glu Ile Val Pro Lys Gly Pro Asn Gly Thr Glu Gly Ala Ser
            520                 525                 530 cgg aca gtt tgc aat aga act gtt ccc agt gca gtg ttt gac atc cac    1990
Arg Thr Val Cys Asn Arg Thr Val Pro Ser Ala Val Phe Asp Ile His
                535                 540                 545
```

-continued

```
gtg gtc tac gtc acc acc acg gag atg tgg ctg gac tgg aag agc cct        2038
Val Val Tyr Val Thr Thr Thr Glu Met Trp Leu Asp Trp Lys Ser Pro
550                 555                 560 gac ggt gct tcc gag tat gtc tac cat tta gtc ata gag tcc aag cat        2086
Asp Gly Ala Ser Glu Tyr Val Tyr His Leu Val Ile Glu Ser Lys His
    565                 570                 575 ggc tct aac cac aca agc acg tat gac aaa gcg att act ctc cag ggc        2134
Gly Ser Asn His Thr Ser Thr Tyr Asp Lys Ala Ile Thr Leu Gln Gly
580                 585                 590                 595 ctg att ccg ggc acc tta tat aac atc acc atc tct cca gaa gtg gac        2182
Leu Ile Pro Gly Thr Leu Tyr Asn Ile Thr Ile Ser Pro Glu Val Asp
        600                 605                 610 cac gtc tgg ggg gac ccc aac tcc act gca cag tac aca cgg ccc agc        2230
His Val Trp Gly Asp Pro Asn Ser Thr Ala Gln Tyr Thr Arg Pro Ser
            615                 620                 625 aat gtg tcc aac att gat gta agt acc aac acc aca gca gca act tta        2278
Asn Val Ser Asn Ile Asp Val Ser Thr Asn Thr Thr Ala Ala Thr Leu
                630                 635                 640 agt tgg cag aac ttt gat gac gcc tct ccc acg tac tcc tac tgc ctt        2326
Ser Trp Gln Asn Phe Asp Asp Ala Ser Pro Thr Tyr Ser Tyr Cys Leu
645                 650                 655 ctt att gag aag gct gga aat tcc agc aac gca aca caa gta gtc acg        2374
Leu Ile Glu Lys Ala Gly Asn Ser Ser Asn Ala Thr Gln Val Val Thr
660                 665                 670                 675 gac att gga att act gac gct aca gtc act gaa tta ata cct ggc tca        2422
Asp Ile Gly Ile Thr Asp Ala Thr Val Thr Glu Leu Ile Pro Gly Ser
        680                 685                 690 tca tac aca gtg gag atc ttt gca caa gta ggg gat ggg atc aag tca        2470
Ser Tyr Thr Val Glu Ile Phe Ala Gln Val Gly Asp Gly Ile Lys Ser
            695                 700                 705 ctg gaa cct ggc cgg aag tca ttc tgt aca gat cct gcg tcc atg gcc        2518
Leu Glu Pro Gly Arg Lys Ser Phe Cys Thr Asp Pro Ala Ser Met Ala
                710                 715                 720 tcc ttc gac tgc gaa gtg gtc ccc aaa gag cca gcc ctg gtt ctc aaa        2566
Ser Phe Asp Cys Glu Val Val Pro Lys Glu Pro Ala Leu Val Leu Lys
725                 730                 735 tgg acc tgc cct cct ggc gcc aat gca ggc ttt gag ctg gag gtc agc        2614
Trp Thr Cys Pro Pro Gly Ala Asn Ala Gly Phe Glu Leu Glu Val Ser
740                 745                 750                 755 agt gga gcc tgg aac aat gcg acc cac ctg gag agc tgc tcc tct gag        2662
Ser Gly Ala Trp Asn Asn Ala Thr His Leu Glu Ser Cys Ser Ser Glu
        760                 765                 770 aat ggc act gag tat aga acg gaa gtc acg tat ttg aat ttt tct acc        2710
Asn Gly Thr Glu Tyr Arg Thr Glu Val Thr Tyr Leu Asn Phe Ser Thr
            775                 780                 785 tcg tac aac atc agc atc acc act gtg tcc tgt gga aag atg gca gcc        2758
Ser Tyr Asn Ile Ser Ile Thr Thr Val Ser Cys Gly Lys Met Ala Ala
                790                 795                 800 ccc acc cgg aac acc tgc act act ggc atc aca gat ccc cct cct cca        2806
Pro Thr Arg Asn Thr Cys Thr Thr Gly Ile Thr Asp Pro Pro Pro Pro
805                 810                 815 gat gga tcc cct aat att aca tct gtc agt cac aat tca gta aag gtc        2854
Asp Gly Ser Pro Asn Ile Thr Ser Val Ser His Asn Ser Val Lys Val
820                 825                 830                 835 aag ttc agt gga ttt gaa gcc agc cac gga ccc atc aaa gcc tat gct        2902
Lys Phe Ser Gly Phe Glu Ala Ser His Gly Pro Ile Lys Ala Tyr Ala
        840                 845                 850 gtc att ctc acc acc ggg gaa gct ggt cac cct tct gca gat gtc ctg        2950
Val Ile Leu Thr Thr Gly Glu Ala Gly His Pro Ser Ala Asp Val Leu
```

-continued

| | | | | |
|---|---|---|---|---|
| | 855 | 860 | 865 | |
| aaa tac acg tat gac gat ttc aaa aag gga gcc tca gat act tat gtg | | | | 2998 |
| Lys Tyr Thr Tyr Asp Asp Phe Lys Lys Gly Ala Ser Asp Thr Tyr Val | | | | |
| 870 875 880 | | | | |
| aca tac ctc ata aga aca gaa gaa aag gga cgt tct cag agc ttg tct | | | | 3046 |
| Thr Tyr Leu Ile Arg Thr Glu Glu Lys Gly Arg Ser Gln Ser Leu Ser | | | | |
| 885 890 895 | | | | |
| gaa gtt ttg aaa tat gaa att gac gtt ggg aat gag tca acc aca ctt | | | | 3094 |
| Glu Val Leu Lys Tyr Glu Ile Asp Val Gly Asn Glu Ser Thr Thr Leu | | | | |
| 900 905 910 915 | | | | |
| ggt tat tac aat ggg aag ctg gaa cct ctg ggc tcc tac cgg gct tgt | | | | 3142 |
| Gly Tyr Tyr Asn Gly Lys Leu Glu Pro Leu Gly Ser Tyr Arg Ala Cys | | | | |
| 920 925 930 | | | | |
| gtg gct ggc ttc acc aac att acc ttc cac cct caa aac aag ggg ctc | | | | 3190 |
| Val Ala Gly Phe Thr Asn Ile Thr Phe His Pro Gln Asn Lys Gly Leu | | | | |
| 935 940 945 | | | | |
| att gat ggg gct gag agc tat gtg tcc ttc agt cgc tac tca gat gct | | | | 3238 |
| Ile Asp Gly Ala Glu Ser Tyr Val Ser Phe Ser Arg Tyr Ser Asp Ala | | | | |
| 950 955 960 | | | | |
| gtt tcc ttg ccc cag gat cca ggt gtc atc tgt gga gcg gtt ttt ggc | | | | 3286 |
| Val Ser Leu Pro Gln Asp Pro Gly Val Ile Cys Gly Ala Val Phe Gly | | | | |
| 965 970 975 | | | | |
| tgt atc ttt ggt gcc ctg gtt att gtg act gtg gga ggc ttc atc ttc | | | | 3334 |
| Cys Ile Phe Gly Ala Leu Val Ile Val Thr Val Gly Gly Phe Ile Phe | | | | |
| 980 985 990 995 | | | | |
| tgg aga aag aag agg aaa gat gca aag aat aat gaa gtg tcc ttt | | | | 3379 |
| Trp Arg Lys Lys Arg Lys Asp Ala Lys Asn Asn Glu Val Ser Phe | | | | |
| 1000 1005 1010 | | | | |
| tct caa att aaa cct aaa aaa tct aag tta atc aga gtg gag aat | | | | 3424 |
| Ser Gln Ile Lys Pro Lys Lys Ser Lys Leu Ile Arg Val Glu Asn | | | | |
| 1015 1020 1025 | | | | |
| ttt gag gcc tac ttc aag aag cag caa gct gac tcc aac tgt ggg | | | | 3469 |
| Phe Glu Ala Tyr Phe Lys Lys Gln Gln Ala Asp Ser Asn Cys Gly | | | | |
| 1030 1035 1040 | | | | |
| ttc gca gag gaa tac gaa gat ctg aag ctt gtt gga att agt caa | | | | 3514 |
| Phe Ala Glu Glu Tyr Glu Asp Leu Lys Leu Val Gly Ile Ser Gln | | | | |
| 1045 1050 1055 | | | | |
| cct aaa tat gca gca gaa ctg gct gag aat aga gga aag aat cgc | | | | 3559 |
| Pro Lys Tyr Ala Ala Glu Leu Ala Glu Asn Arg Gly Lys Asn Arg | | | | |
| 1060 1065 1070 | | | | |
| tat aat aat gtt ctg ccc tat gat att tcc cgt gtc aaa ctt tcg | | | | 3604 |
| Tyr Asn Asn Val Leu Pro Tyr Asp Ile Ser Arg Val Lys Leu Ser | | | | |
| 1075 1080 1085 | | | | |
| gtc cag acc cat tca acg gat gac tac atc aat gcc aac tac atg | | | | 3649 |
| Val Gln Thr His Ser Thr Asp Asp Tyr Ile Asn Ala Asn Tyr Met | | | | |
| 1090 1095 1100 | | | | |
| cct ggc tac cac tcc aag aaa gat ttt att gcc aca caa gga cct | | | | 3694 |
| Pro Gly Tyr His Ser Lys Lys Asp Phe Ile Ala Thr Gln Gly Pro | | | | |
| 1105 1110 1115 | | | | |
| tta ccg aac act ttg aaa gat ttt tgg cgt atg gtt tgg gag aaa | | | | 3739 |
| Leu Pro Asn Thr Leu Lys Asp Phe Trp Arg Met Val Trp Glu Lys | | | | |
| 1120 1125 1130 | | | | |
| aat gta tat gcc atc att atg ttg act aaa tgt gtt gaa cag gga | | | | 3784 |
| Asn Val Tyr Ala Ile Ile Met Leu Thr Lys Cys Val Glu Gln Gly | | | | |
| 1135 1140 1145 | | | | |
| aga acc aaa tgt gag gag tat tgg ccc tcc aag cag gct cag gac | | | | 3829 |
| Arg Thr Lys Cys Glu Glu Tyr Trp Pro Ser Lys Gln Ala Gln Asp | | | | |
| 1150 1155 1160 | | | | |
| tat gga gac ata act gtg gca atg aca tca gaa att gtt ctt ccg | | | | 3874 |

-continued

| | | | | | | | | | | | |
|---|---|---|---|---|---|---|---|---|---|---|---|
| Tyr | Gly | Asp | Ile | Thr | Val | Ala | Met | Thr | Ser | Glu | Ile | Val | Leu | Pro |
| | | | 1165 | | | | 1170 | | | | 1175 | | | |

```
gaa tgg acc atc aga gat ttc aca gtg aaa aat atc cag aca agt      3919
Glu Trp Thr Ile Arg Asp Phe Thr Val Lys Asn Ile Gln Thr Ser
            1180                1185                1190 gag agt cac cct ctg aga cag ttc cat ttc acc tcc tgg cca gac      3964
Glu Ser His Pro Leu Arg Gln Phe His Phe Thr Ser Trp Pro Asp
        1195                1200                1205 cac ggt gtt ccc gac acc act gac ctg ctc atc aac ttc cgg tac      4009
His Gly Val Pro Asp Thr Thr Asp Leu Leu Ile Asn Phe Arg Tyr
    1210                1215                1220 ctc gtt cgt gac tac atg aag cag agt cct ccc gaa tcg ccg att      4054
Leu Val Arg Asp Tyr Met Lys Gln Ser Pro Pro Glu Ser Pro Ile
1225                1230                1235 ctg gtg cat tgc agt gct ggg gtc gga agg acg ggc act ttc att      4099
Leu Val His Cys Ser Ala Gly Val Gly Arg Thr Gly Thr Phe Ile
            1240                1245                1250 gcc att gat cgt ctc atc tac cag ata gag aat gag aac acc gtg      4144
Ala Ile Asp Arg Leu Ile Tyr Gln Ile Glu Asn Glu Asn Thr Val
        1255                1260                1265 gat gtg tat ggg att gtg tat gac ctt cga atg cat agg cct tta      4189
Asp Val Tyr Gly Ile Val Tyr Asp Leu Arg Met His Arg Pro Leu
    1270                1275                1280 atg gtg cag aca gag gac cag tat gtt ttc ctc aat cag tgt gtt      4234
Met Val Gln Thr Glu Asp Gln Tyr Val Phe Leu Asn Gln Cys Val
1285                1290                1295 ttg gat att gtc aga tcc cag aaa gac tca aaa gta gat ctt atc      4279
Leu Asp Ile Val Arg Ser Gln Lys Asp Ser Lys Val Asp Leu Ile
            1300                1305                1310 tac cag aac aca act gca atg aca atc tat gaa aac ctt gcg ccc      4324
Tyr Gln Asn Thr Thr Ala Met Thr Ile Tyr Glu Asn Leu Ala Pro
        1315                1320                1325 gtg acc aca ttt gga aag acc aat ggt tac atc gcc taa ttccaaagga  4373
Val Thr Thr Phe Gly Lys Thr Asn Gly Tyr Ile Ala
    1330                1335 ataacctttc tggagtgaac cagaccgtcg cacccacagc gaaggcacat gccccgatgt   4433
cgacatgttt ttatatgtct aatatcttaa ttctttgttc tgttttgtga gaactaattt   4493
tgagggcatg aagctgcata tgatagatga caaattgggg ctgtcggggg ctgtggatgg   4553
gtggggagca aatcatctgc attcctgatg accaatggga tgaggtcact ttttttttt    4613 tccccttga ggattgcgga aaaccaggaa aagggatcta tgattttttt ttccaaaaca   4673
atttcttttt taaaaagact attttatatg attcacatgc taaagccagg attgtgttgg   4733
gttgaatata ttttaagtat cagaggtcta ttttaccta ctgtgtcttg gaatctagcc     4793
gatggaaaat acctaattgt ggatgatgat tgcgcaggga ggggtacgtg gcacctcttc   4853
cgaatgggtt ttctatttga acatgtgcct tttctgaatt atgcttccac aggcaaaact   4913
cagtagagat ctatattttt gtactgaatc tcataattgg aatatcgga atatttaaac    4973 agtagcttag catcagaggt ttgcttcctc agtaacattt ctgttctcat ttgatcaggg   5033
gaggcctctt tgccccggcc ccgcttcccc tgccccgtg tgatttgtgc tccattttttt   5093 cttccctttt ccctcccagt tttc                                         5117

<210> SEQ ID NO 4
<211> LENGTH: 1337
<212> TYPE: PRT
<213> ORGANISM: Homo sapiens
```

<400> SEQUENCE: 4

```
Met Lys Pro Ala Ala Arg Glu Ala Arg Leu Pro Pro Arg Ser Pro Gly
1               5                   10                  15

Leu Arg Trp Ala Leu Pro Leu Leu Leu Leu Leu Arg Leu Gly Gln
            20                  25                  30

Ile Leu Cys Ala Gly Gly Thr Pro Ser Pro Ile Pro Asp Pro Ser Val
            35                  40                  45

Ala Thr Val Ala Thr Gly Glu Asn Gly Ile Thr Gln Ile Ser Ser Thr
            50                  55                  60

Ala Glu Ser Phe His Lys Gln Asn Gly Thr Gly Thr Pro Gln Val Glu
65                  70                  75                  80

Thr Asn Thr Ser Glu Asp Gly Glu Ser Ser Gly Ala Asn Asp Ser Leu
                85                  90                  95

Arg Thr Pro Glu Gln Gly Ser Asn Gly Thr Asp Gly Ala Ser Gln Lys
                100                 105                 110

Thr Pro Ser Ser Thr Gly Pro Ser Pro Val Phe Asp Ile Lys Ala Val
                115                 120                 125

Ser Ile Ser Pro Thr Asn Val Ile Leu Thr Trp Lys Ser Asn Asp Thr
130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
                165                 170                 175

Arg Pro Ala Thr Ser Tyr Val Phe Ser Ile Thr Pro Gly Ile Gly Asn
                180                 185                 190

Glu Thr Trp Gly Asp Pro Arg Val Ile Lys Val Ile Thr Glu Pro Ile
                195                 200                 205

Pro Val Ser Asp Leu Arg Val Ala Leu Thr Gly Val Arg Lys Ala Ala
                210                 215                 220

Leu Ser Trp Ser Asn Gly Asn Gly Thr Ala Ser Cys Arg Val Leu Leu
225                 230                 235                 240

Glu Ser Ile Gly Ser His Glu Glu Leu Thr Gln Asp Ser Arg Leu Gln
                245                 250                 255

Val Asn Ile Ser Asp Leu Lys Pro Gly Val Gln Tyr Asn Ile Asn Pro
                260                 265                 270

Tyr Leu Leu Gln Ser Asn Lys Thr Lys Gly Asp Pro Leu Gly Thr Glu
            275                 280                 285

Gly Gly Leu Asp Ala Ser Asn Thr Glu Arg Ser Arg Ala Gly Ser Pro
290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
                340                 345                 350

Thr Glu Gly Gln Pro Gln Ala Ile Glu Phe Arg Thr Asn Ala Ile Gln
                355                 360                 365

Val Phe Asp Val Thr Ala Val Asn Ile Ser Ala Thr Ser Leu Thr Leu
                370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415
```

```
Pro Arg Ala Val Ile Pro Gly Leu Arg Ser Ser Thr Phe Tyr Asn Ile
            420                 425                 430

Thr Val Cys Pro Val Leu Gly Asp Ile Glu Gly Thr Pro Gly Phe Leu
        435                 440                 445

Gln Val His Thr Pro Val Pro Val Ser Asp Phe Arg Val Thr Val
    450                 455                 460

Val Ser Thr Thr Glu Ile Gly Leu Ala Trp Ser Ser His Asp Ala Glu
465                 470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Gly Gly Leu Phe Pro Gly
            500                 505                 510

Thr Lys Tyr Cys Phe Glu Ile Val Pro Lys Gly Pro Asn Gly Thr Glu
            515                 520                 525

Gly Ala Ser Arg Thr Val Cys Asn Arg Thr Val Pro Ser Ala Val Phe
530                 535                 540

Asp Ile His Val Val Tyr Val Thr Thr Thr Glu Met Trp Leu Asp Trp
545                 550                 555                 560

Lys Ser Pro Asp Gly Ala Ser Glu Tyr Val Tyr His Leu Val Ile Glu
                565                 570                 575

Ser Lys His Gly Ser Asn His Thr Ser Thr Tyr Asp Lys Ala Ile Thr
            580                 585                 590

Leu Gln Gly Leu Ile Pro Gly Thr Leu Tyr Asn Ile Thr Ile Ser Pro
            595                 600                 605

Glu Val Asp His Val Trp Gly Asp Pro Asn Ser Thr Ala Gln Tyr Thr
610                 615                 620

Arg Pro Ser Asn Val Ser Asn Ile Asp Val Ser Thr Asn Thr Thr Ala
625                 630                 635                 640

Ala Thr Leu Ser Trp Gln Asn Phe Asp Asp Ala Ser Pro Thr Tyr Ser
            645                 650                 655

Tyr Cys Leu Leu Ile Glu Lys Ala Gly Asn Ser Ser Asn Ala Thr Gln
                660                 665                 670

Val Val Thr Asp Ile Gly Ile Thr Asp Ala Thr Val Thr Glu Leu Ile
            675                 680                 685

Pro Gly Ser Ser Tyr Thr Val Glu Ile Phe Ala Gln Val Gly Asp Gly
            690                 695                 700

Ile Lys Ser Leu Glu Pro Gly Arg Lys Ser Phe Cys Thr Asp Pro Ala
705                 710                 715                 720

Ser Met Ala Ser Phe Asp Cys Glu Val Val Pro Lys Glu Pro Ala Leu
                725                 730                 735

Val Leu Lys Trp Thr Cys Pro Pro Gly Ala Asn Ala Gly Phe Glu Leu
            740                 745                 750

Glu Val Ser Ser Gly Ala Trp Asn Asn Ala Thr His Leu Glu Ser Cys
            755                 760                 765

Ser Ser Glu Asn Gly Thr Glu Tyr Arg Thr Glu Val Thr Tyr Leu Asn
770                 775                 780

Phe Ser Thr Ser Tyr Asn Ile Ser Ile Thr Thr Val Ser Cys Gly Lys
785                 790                 795                 800

Met Ala Ala Pro Thr Arg Asn Thr Cys Thr Thr Gly Ile Thr Asp Pro
                805                 810                 815

Pro Pro Pro Asp Gly Ser Pro Asn Ile Thr Ser Val Ser His Asn Ser
            820                 825                 830
```

-continued

```
Val Lys Val Lys Phe Ser Gly Phe Glu Ala Ser His Gly Pro Ile Lys
        835                 840                 845
Ala Tyr Ala Val Ile Leu Thr Thr Gly Glu Ala Gly His Pro Ser Ala
        850                 855                 860
Asp Val Leu Lys Tyr Thr Tyr Asp Asp Phe Lys Lys Gly Ala Ser Asp
865                 870                 875                 880
Thr Tyr Val Thr Tyr Leu Ile Arg Thr Glu Glu Lys Gly Arg Ser Gln
        885                 890                 895
Ser Leu Ser Glu Val Leu Lys Tyr Glu Ile Asp Val Gly Asn Glu Ser
        900                 905                 910
Thr Thr Leu Gly Tyr Tyr Asn Gly Lys Leu Glu Pro Leu Gly Ser Tyr
        915                 920                 925
Arg Ala Cys Val Ala Gly Phe Thr Asn Ile Thr Phe His Pro Gln Asn
        930                 935                 940
Lys Gly Leu Ile Asp Gly Ala Glu Ser Tyr Val Ser Phe Ser Arg Tyr
945                 950                 955                 960
Ser Asp Ala Val Ser Leu Pro Gln Asp Pro Gly Val Ile Cys Gly Ala
                965                 970                 975
Val Phe Gly Cys Ile Phe Gly Ala Leu Val Ile Val Thr Val Gly Gly
        980                 985                 990
Phe Ile Phe Trp Arg Lys Lys Arg  Lys Asp Ala Lys Asn  Asn Glu Val
        995                 1000                1005
Ser Phe  Ser Gln Ile Lys Pro  Lys Lys Ser Lys Leu  Ile Arg Val
    1010                1015                1020
Glu Asn  Phe Glu Ala Tyr Phe  Lys Lys Gln Gln Ala  Asp Ser Asn
    1025                1030                1035
Cys Gly  Phe Ala Glu Glu Tyr  Glu Asp Leu Lys Leu  Val Gly Ile
    1040                1045                1050
Ser Gln  Pro Lys Tyr Ala Ala  Glu Leu Ala Glu Asn  Arg Gly Lys
    1055                1060                1065
Asn Arg  Tyr Asn Asn Val Leu  Pro Tyr Asp Ile Ser  Arg Val Lys
    1070                1075                1080
Leu Ser  Val Gln Thr His Ser  Thr Asp Asp Tyr Ile  Asn Ala Asn
    1085                1090                1095
Tyr Met  Pro Gly Tyr His Ser  Lys Lys Asp Phe Ile  Ala Thr Gln
    1100                1105                1110
Gly Pro  Leu Pro Asn Thr Leu  Lys Asp Phe Trp Arg  Met Val Trp
    1115                1120                1125
Glu Lys  Asn Val Tyr Ala Ile  Ile Met Leu Thr Lys  Cys Val Glu
    1130                1135                1140
Gln Gly  Arg Thr Lys Cys Glu  Glu Tyr Trp Pro Ser  Lys Gln Ala
    1145                1150                1155
Gln Asp  Tyr Gly Asp Ile Thr  Val Ala Met Thr Ser  Glu Ile Val
    1160                1165                1170
Leu Pro  Glu Trp Thr Ile Arg  Asp Phe Thr Val Lys  Asn Ile Gln
    1175                1180                1185
Thr Ser  Glu Ser His Pro Leu  Arg Gln Phe His Phe  Thr Ser Trp
    1190                1195                1200
Pro Asp  His Gly Val Pro Asp  Thr Thr Asp Leu Leu  Ile Asn Phe
    1205                1210                1215
Arg Tyr  Leu Val Arg Asp Tyr  Met Lys Gln Ser Pro  Pro Glu Ser
    1220                1225                1230
Pro Ile  Leu Val His Cys Ser  Ala Gly Val Gly Arg  Thr Gly Thr
```

-continued

```
               1235                1240                1245
Phe Ile Ala Ile Asp Arg Leu Ile Tyr Gln Ile Glu Asn Glu Asn
    1250                1255                1260
Thr Val Asp Val Tyr Gly Ile Val Tyr Asp Leu Arg Met His Arg
    1265                1270                1275
Pro Leu Met Val Gln Thr Glu Asp Gln Tyr Val Phe Leu Asn Gln
    1280                1285                1290
Cys Val Leu Asp Ile Val Arg Ser Gln Lys Asp Ser Lys Val Asp
    1295                1300                1305
Leu Ile Tyr Gln Asn Thr Thr Ala Met Thr Ile Tyr Glu Asn Leu
    1310                1315                1320
Ala Pro Val Thr Thr Phe Gly Lys Thr Asn Gly Tyr Ile Ala
    1325                1330                1335
```

MODULATION OF ENDOTHELIAL CELL SURFACE RECEPTOR ACTIVITY IN THE REGULATION OF ANGIOGENESIS

CROSS REFERENCE TO RELATED APPLICATIONS

This application is a continuation-in-part of U.S. patent application Ser. No. 09/152,160, filed Sep. 11, 1998, now U.S. Pat. No. 6,248,327, herein incorporated by reference in its entirety.

GRANT STATEMENT

This work was supported by NIH grants DK38517 and CA 68485. The U.S. Government has certain rights in the invention.

TECHNICAL FIELD

The present invention relates generally to the modulation of the activity of an endothelial cell surface receptor in the regulation of endothelial cell proliferation and migration and in the regulation of angiogenesis. More particularly, the present invention relates to the modulation of ECRTP/DEP-1 activity in the regulation of endothelial cell proliferation and migration and in the regulation of angiogenesis.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels. The term "endothelial modulating activity" means the capability of a molecule to modulate angiogenesis in general and, for example, to stimulate or inhibit the growth of endothelial cells in culture. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, and abnormal growth by endothelial cells and supports the pathological damage seen in these conditions. The diverse pathological disease states in which unregulated angiogenesis is present have been grouped together as angiogenic dependent or angiogenic associated diseases.

It is also recognized that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

The development of renal glomerular capillaries is anatomically segregated and temporally staged in a multi-step process. The process involves recruitment of endothelial progenitors from adjacent mesenchyme, assembly of an arborized branching network, and maturation and specialization of endothelial cells adjacent to mesangial and visceral epithelial cells. Receptors for extracellular matrix components, cell surface molecules and growth factors have been assigned roles to mediate steps in this assembly process. See e.g., Wallner et al., *Microsc Res Tech* 39:261–284 (1997); Takahashi et al., *Kidney Int* 53:826–835 (1998).

Vascular endothelial growth factor (VEGF) is an important participant, as it is induced in S stage developing glomerular epithelial cells, and endothelial progenitors that are recruited to glomerular capillaries from the adjacent metanephric mesenchyme express the VEGF receptor, flk-1. Robert et al., *Am J Physiol* 271:F744–F753 (1996).

Neutralizing VEGF antibodies interrupt postnatal murine glomerular capillary development. Kitamoto et al., *J Clin Invest* 99:2351–2357 (1997). Deletion of either PDGFβ receptor or PDGFβ genes in mice causes defective recruitment of mesangial cell precursors with failure of glomerular development. Soriano, P., *Genes Dev* 8:1888–1896 (1994); Leveen et al., *Genes Dev* 8:1875–1887 (1994). TGFβ1 expression and type II TGFβ receptors appear critical for vascular development in the embryonic yolk sac (prior to renal development), and type II receptors mediate in vitro capillary morphogenesis of endothelial cells derived from bovine glomeruli. Choime et al., *J Biol Chem* 270:21144–21150 (1995).

Early evidence suggests that Eph family receptors and their ephrin ligands participate in glomerular vascular development. EphB1 receptors are expressed in isolated mesenchymal cells in a pattern similar to that of flk-1, and high level expression of ephrin-B1 is seen at the vascular cleft of developing glomeruli, as well as in capillary endothelial cells of mature glomeruli. Daniel et al., *Kidney Int* 50:S-73–S-81 (1996). Oligomerized forms of ephrin-B1 stimulate in vitro assembly of human renal microvascular endothelial cells (HRMEC) into capillary-like structures. Stein et al., *Genes Dev* 12:667–678 (1998).

A selected subclass of receptor tyrosine phosphatases, including DPTP10D, serve important roles in directing axonal migration and neural network assembly. Desai et al., *Cell* 84:599–609 (1996). Recent data has identified mRNA expression of a related receptor phosphatase, ECRTP/DEP-1, in arterial sites in mammalian kidney. Borges et al., *Circulation Research* 79:570–580 (1996). To date, however, there has been no evidence to implicate receptor tyrosine phosphatases in microvascular or glomerular capillary assembly or maturation.

Vascular endothelial cells display a diverse range of vascular bed specific properties (Gumkowski et al., *Blood Vessels* 24:11–13 (1987)), yet the requirement to maintain a continuous, antithrombotic monolayer lining the vascular space imposes rigorous requirements that their proliferation, migration and differentiation be regulated by interendothelial contacts. Specialized intercellular contacts permit communication among interacting endothelial cells (Lampugnani et al., *J Cell Biol* 129:203–217 (1995)) yet the mechanisms regulating arrest of proliferation and migration in response to interendothelial contact have not been elucidated. Tight regulatory control over proliferation imposed by interendothelial cell contact is apparent in the low basal mitotic index among endothelial cells in existing vessels. Engerman et al., *Laboratory Investigation* 17:738–744 (1967). This is in contrast with the proliferative endothelial responses that are evoked by mechanical disruption of large vessels. More et al., *J Patho* 172:287–292 (1994). Similar proliferation and migration responses are stimulated at the margin of a confluent endothelial monolayer by "wounding", or physical removal cells from the packed monolayer. Coomber, *J Cell Biochem* 52:289–296 (1993).

The molecular basis for effects of interendothelial contact on migratory and proliferative responses is not defined, yet studies of cultured cells have shown that endothelial, fibroblast, and epithelial cells grow to confluency at a predictable density, then arrest proliferation (density arrest). Augenlicht and Baserga, *Exp Cell Res* 89:255–262 (1974); Beekhuizen and van Furth, *J Vascular Res* 31:230–239 (1994); Rijksen et al., *J Cell Physiol* 154:393–401 (1993). This phenomenon can be very relevant to the behavior of endothelial cells in vascular sites in situ. Indeed, model culture systems of endothelial "wounding" have shown that endothelial cells at the edge of an imposed "wound" rapidly extend lamellae, spread, migrate and proliferate to replace the deficit created by mechanical disruption of the monolayer. Coomber, *J Cell Biochem* 52:289–296 (1993).

Pallen and Tong observed that membrane-associated tyrosine phosphatase activity recovered from cultured Swiss 3T3 cells increased eight (8)-fold (expressed as activity/mg protein) as cells approached a density of $5 \times 10^4/cm^2$, while soluble fraction tyrosine phosphatase was unaffected by cell density. Pallen and Tong, *Proc Natl Acad Sci USA* 88:6996–7000 (1991). Ostman et al. determined that the abundance of a receptor tyrosine phosphatase cloned from HeLa cells and named DEP-1, is increased as cells approach high density. Ostman et al., *Proc Natl Acad Sci USA* 91:9680–9684 (1994). However, no links between molecules that evoke proliferation arrest and receptor tyrosine phosphatases have been made.

To date, available information does not indicate what sort of receptor-ligand interaction might mediate a cell surface generated signal for density or contact arrest. The identification of such a receptor-ligand interaction is therefore needed in that it will serve as a basis for intervention in a disorder wherein density or contact arrest, or the preclusion of density or contact arrest, has therapeutic value. Such disorders include disorders characterized by undesired angiogenesis, such as angiogenesis associated with tumor growth. Thus, what is also needed is a composition and method which can inhibit the unwanted growth of blood vessels, especially into tumors. The composition and method should attenuate the formation of the capillaries in the tumors thereby inhibiting the growth of the tumors.

SUMMARY OF THE INVENTION

In accordance with the present invention, a method of modulating angiogenesis in a vertebrate subject is provided. The method comprises administering to the vertebrate subject an ECRTP/DEP-1 activity modulating amount of a composition, whereby an ECRTP/DEP-1 within the vertebrate subject is contacted by the composition; and modulating angiogenesis through the contacting of the ECRTP/DEP-1 with the composition.

In accordance with the present invention a method of modulating endothelial cell migration and proliferation in a vertebrate subject is also provided. The method comprises administering to the vertebrate subject an ECRTP/DEP-1 activity-modulating amount of a composition, whereby an ECRTP/DEP-1 within the vertebrate subject is contacted by the composition; and modulating endothelial cell migration and proliferation through the contacting of the ECRTP/DEP-1 with the composition.

In accordance with the present invention there is also provided an antibody which preferentially binds the ECRTP/DEP-1. Optionally, the antibody comprises a monoclonal antibody or fragment or derivative thereof which preferentially binds the ECRTP/DEP-1.

In accordance with the present invention, a method for isolating an endogenous ligand for an ECRTP/DEP-1 is also provided. The method comprises the steps of contacting cells or cell lysates having the ligand with ECRTP/DEP-1; and isolating the ligand which binds with ECRTP/DEP-1.

A method of screening candidate substances for an ability to modulate ECRTP/DEP-1 biological activity is also disclosed. The method comprises establishing test samples comprising an ECRTP/DEP-1 polypeptide or fragment thereof; administering a candidate substance to the test samples; and measuring the interaction, effect, or combination thereof, of the candidate substance on the test sample to thereby determine the ability of the candidate substance to modulate ECRTP/DEP-1 biological activity.

In accordance with the present invention there are also provided methods for performing a screening assay for identifying a compound that modulates an activity of an ECRTP/DEP-1 in both a cell-based and a cell-free assay. In a cell-based assay, the method comprises the steps of establishing replicate test and control cultures of cells that express the ECRTP/DEP-1; administering a candidate compound to the cells in the test culture but not the control culture; measuring ECRTP/DEP-1 activity in cells in the test and the control cultures; and determining that the candidate compound modulates the ECRTP/DEP-1 activity in a cell if the ECRTP/DEP-1 activity measured for the test culture is greater or less than the ECRTP/DEP-1 activity measured for the control culture.

In a cell-free system, the method comprises the steps of establishing a control system comprising an ECRTP/DEP-1 and a ligand wherein the ECRTP/DEP-1 is capable of binding to the ligand; establishing a test system comprising the ECRTP/DEP-1, the ligand, and a candidate compound, measuring the binding affinity of the ECRTP/DEP-1, and the ligand in the control and the test systems; and determining that the candidate compound modulates ECRTP/DEP-1 activity in a cell-free system if the binding affinity measured for the test system is less than or greater than the binding affinity measured for the control system.

In another embodiment, the screening assay methods of the present invention pertain to comparing the effect of a candidate compound to inhibit growth of cells expressing exogenous ECRTP/DEP-1 compared with those not expressing ECRTP/DEP-1 and determining that the effect of altering ECRTP/DEP-1 activity is responsible by demonstrating the lack of activity of the candidate compound on cells not expressing ECRTP/DEP-1. Thus, the screening assays of the present invention show changes in growth that are responsive to changes in ECRTP/DEP-1 activity.

In accordance with the present invention there is also provided a method for delivering a therapeutic composition to a tissue in a patient, wherein the tissue is characterized as having undesirable endothelial cell proliferation. The method comprises the steps of introducing into the patient a biologically effective amount of an antibody operatively linked to a selected therapeutic agent, the antibody preferentially binding to an ECRTP/DEP-1 on the surface of the endothelial cells, whereby an ECRTP/DEP-1 within the vertebrate subject is contacted by the antibody; and delivering the therapeutic composition to the tissue through the contacting of the ECRTP/DEP-1 with the composition.

It is therefore an object of the present invention to localize and characterize a receptor-ligand interaction which mediates a cell surface-generated signal for cell growth and survival.

It is another object of the present invention to provide for the modulation of a cell surface receptor activity in endothelial cells to mediate a cell surface-generated signal for cell growth and survival.

It is still another object of the present invention to provide for the modulation of a cell surface receptor activity for use in the inhibition or stimulation of angiogenesis.

It is yet another object of the present invention to identify compounds which modulate a receptor-ligand interaction which mediates a cell surface-generated signal for density or contact arrest.

Some of the aspects and objects of the invention having been stated hereinabove, other aspects and objects will become evident as the description proceeds, when taken in connection with the accompanying Drawings and Examples as best described hereinbelow.

A single peptide sequence (#41) in the series represents amino acid residues in n-QSRDTEVL-c (SEQ ID NO: 1).

Figure 13A:
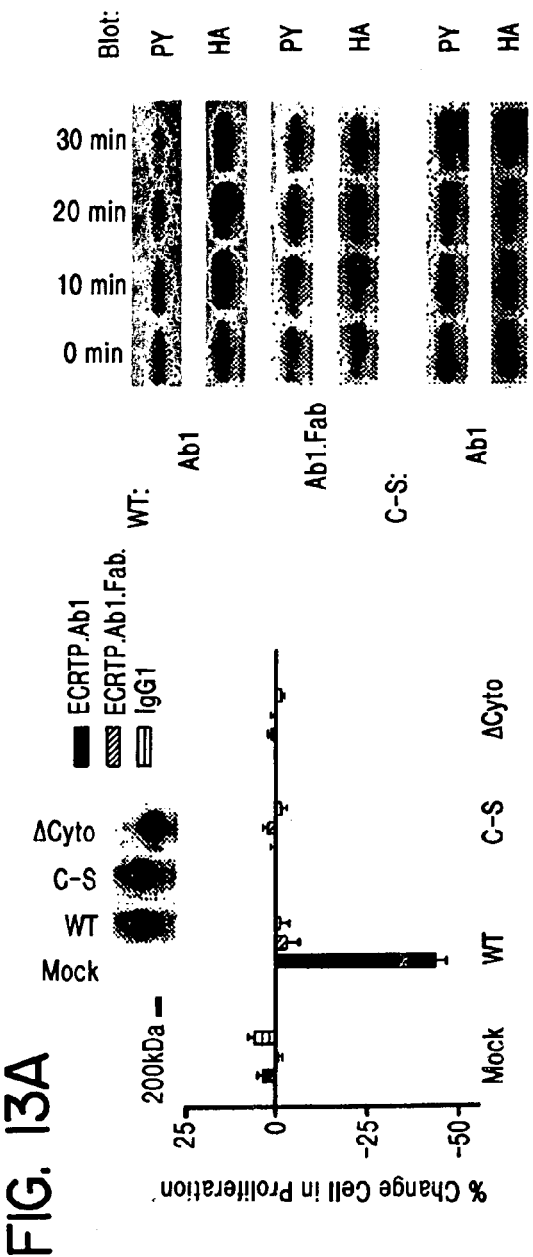

FIG. 13A is a combination of autoradiographs and a graph depicting that ECRTPAB-1 promotes dephosphorylation of ECRTP and arrests growth of transfected CHO cells expressing wild type ECRTP, but not mutant ECRTP proteins, C/S (catalytically inactivated point mutant) or cy (a cytoplasmic domain deletion). CHO cells were replated at 24 hours in the presence of ECRTPAb-1, ECRTPAb-1-Fab, or control IgG1 and assayed for cell number at 48 hours after transfection. In right panels, cells were transfected, cultured for 48 hours in serum-containing medium (5%), and exposed to 70 nM of ECRTPAb-1 or ECRTPAb-1-Fab for the times indicated. ECRTP was immunoprecipitated and assayed by immunoblot for phosphotyrosine content (anti-PY) and antigen recovery (anti-HA), as indicated. ECRTPAb-1, but not ECRTPAb-1-Fab, promoted acute dephosphorylation of wt but not catalytically inactive ECRTP.

Figure 13B:
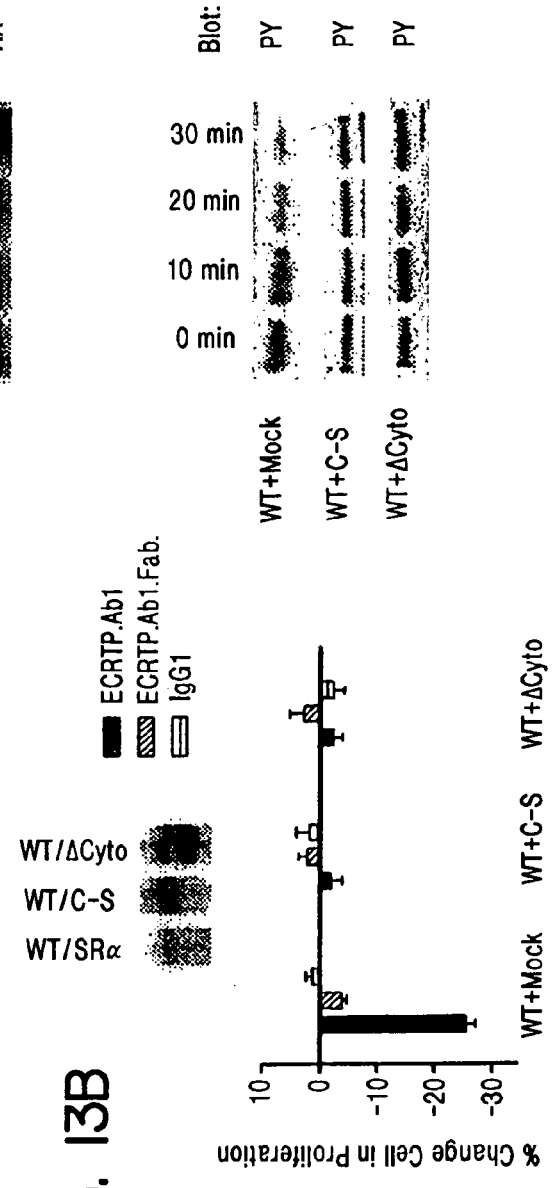

FIG. 13B is a combination of autoradiographs and a graph demonstrating that cotransfection of wild type ECRTP with either C/S or cy forms abrogates the dephosphorylation of ECRTP imposed by exposure of cells to ECRTPAb-1. These mutant forms function as dominant negative proteins to block the ECRTPAb-1-induced formation of catalytically active ECRTP dimers that arrest cell growth and promote ECRTP dephosphorylation.

DETAILED DESCRIPTION OF THE INVENTION

A mammalian transmembrane protein gene product called DEP-1 (for density enhanced phosphatase), ECRTP, PTPRJ, HPTPη, CD148, BYP, depending upon species and cDNA origin), was initially cloned from fibroblasts and was subsequently shown to be expressed (hereinafter referred to as an "ECRTP/DEP-1") on all hematopoietic lineages (de la Fuente-Garcia et al., *Blood* 91:2800–2809 (1998), including erythroid progenitor cells, megakaryocytes and platelets, lymphocytes, polymorphononuclear leukocytes and platelets, and very prominently in endothelial cells. Borges et al., *Circulation Research* 79:570–580 (1996), Schoecklmann et al., *J Am Soc Nephrol* 5:730 (1994)(abstract). This gene product has been shown to promote differentiation of erythroid progenitor cells (Kumet et al., *J Biol Chem* 271: 30916–30921 (1996)), to modulate lymphocyte function when crosslinked with other signaling proteins (de la Fuente-Garcia et al., *Blood* 91:2800–2809 (1998)); and to inhibit clonal expression of breast cancer cell lines overexpressing the protein (Keane et al., *Cancer Research* 56:4236–4243 (1996)).

In accordance with the present invention, it has been demonstrated that antibodies specific for ectodomain epitopes of the ECRTP/DEP-1 block endothelial migration and proliferation in response to phorbol myristate acetate and fetal bovine serum respectively. It is recognized that the biological activity to inhibit endothelial proliferation and migration is a strong indicator of angiogenesis inhibitory activity. Accordingly, the ECRTP/DEP-1 is also a mediator of inhibitory signals that block angiogenesis.

In accordance with the present invention, then, antibodies that aggregate the ECRTP/DEP-1, including monoclonal antibody ECRTPAb-1 described herein, inhibit angiogenesis. Indeed, monoclonal antibodies against the ectodomain of ECRTP/DEP-1 inhibit proliferation (as demonstrated by BrdU uptake experiments) and migration of endothelial cells. Fab fragments of the same monoclonal have no such activity. Accordingly, such monoclonal ECRTP/DEP-1 antibodies described herein and derivatives thereof, have biological activity as angiogenesis inhibitors.

An endogenous ligand for the receptor ectodomain signals endothelial growth arrest. Therefore, in accordance with the present invention, a method of screening for the endogenous ligand is provided. For example, the endogenous ligand is isolated through the preparation of fusion proteins of the ECRTP/DEP-1 ectodomain as affinity reagents to identify, establish assays for, and clone the putative natural ligand expressed on endothelial cells. The purified and isolated endogenous ligand thus also has therapeutic application as an angiogenesis inhibitor.

In accordance with the present invention, synthetic peptides and peptidomimetics can also be used to contact the ECRTP/DEP-1 to activate ECRTP/DEP-1 activity.

The ECRTP/DEP-1 is expressed on the luminal and interendothelial membranes of endothelial cells in microvascular and large arterial vessels of kidney and other organs, including but not limited to heart, spleen, muscle and skin. The ECRTP/DEP-1 localizes to interendothelial contacts in cultured endothelial cells, and in regions that overlap, but localization is not limited to the VE cadherin rich junctional complexes. ECRTP/DEP-1 activity (tyrosine phosphatase activity) increases approximately two times in confluent cells anticipating density mediated growth arrest. Moreover, over-expression of ECRTP/DEP-1 confers growth arrest on subconfluent endothelial cells. Thus, in accordance with the present invention, a method of modulating ECRTP/DEP-1 activity by contacting an ECRTP/DEP-1 with an ECRTP/DEP-1 modulating composition is contemplated. A method of screening for such a composition is also contemplated. Finally, a method of targeting a therapeutic composition to interendothelial contacts by preparing an antibody which preferably binds the ECRTP/DEP-1 and which is bound to the therapeutic composition in provided in accordance with the present invention.

A. General Considerations

The present invention relates generally to the discovery that angiogenesis is modulated by the ECRTP/DEP-1 and that activation of ECRTP/DEP-1 function inhibits angiogenesis. This discovery is important because of the role that angiogenesis plays in a variety of disease processes. By modulating angiogenesis, one can intervene in the disease, ameliorate the symptoms, and in some cases cure the disease.

Where the growth of new blood vessels is the cause of, or contributes to, the pathology associated with a disease, inhibition of angiogenesis will reduce the deleterious effects of the disease. Examples include rheumatoid arthritis, diabetic retinopathy, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, the ECRTP/DEP-1 localizes to endothelial cells and thus, primarily new vessel growth contains substantial ECRTP/DEP-1, and therefore the therapeutic methods do not adversely effect mature vessels. Furthermore, the ECRTP/DEP-1 is not widely distributed in normal tissues, but rather is found selectively on the surface of endothelial cells, thereby assuring that the therapy can be selectively targeted.

The discovery that binding the ECRTP/DEP-1 will effectively inhibit angiogenesis allows for the development of therapeutic compositions with potentially high specificity, and therefore relatively low toxicity. Thus although the invention discloses the preferred use of an anti-ECRTP/DEP-1 monoclonal antibody, one can design reagents which selectively bind ECRTP/DEP-1, and therefore do not have the side effect of modulating other biological processes other that those mediated by ECRTP/DEP-1.

As shown by the present teachings, it is possible to prepare monoclonal antibodies highly selective for immunoreaction with the ECRTP/DEP-1 that are similarly selective for modulation of ECRTP/DEP-1 function. In addition, peptides can be designed to be selective for binding to ECRTP/DEP-1, as described further herein. Prior to the discoveries of the present invention, it was not known that angiogenesis could be modulated in vivo by the use of reagents that modulate the biological function of ECRTP/DEP-1 or other receptor tyrosine phosphatase.

Other related methods are described in U.S. Pat. Nos. 5,753,230; 5,733,876; 5,762,918; 5,776,427; 5,766,591; and 5,660,827, the entire contents of each of which are herein incorporated by reference.

Following long-standing patent law convention, the terms "a" and "an" mean "one or more" when used in this application, including the claims.

B. Methods for Modulating of Angiogenesis

The invention provides for a method for the modulation of angiogenesis in a tissue, and thereby modulating events in the tissue which depend upon angiogenesis. Generally, the method comprises administering to the tissue a composition comprising an angiogenesis-modulating amount of an ECRTP/DEP-1 modulator. As disclosed herein the term "modulate" is meant to encompass both the inhibition or stimulation of angiogenesis. Thus, the therapeutic methods of the present invention pertain to both the inhibition or stimulation of angiogenesis, depending on the disorder to be treated.

Angiogenesis includes a variety of processes involving neovascularization of a tissue including "sprouting", vasculogenesis, or vessel enlargement, all of which angiogenesis processes are mediated by and dependent upon the expression of ECRTP/DEP-1. With the exception of traumatic wound healing, corpus luteum formation and embryogenesis, it is believed that many angiogenesis processes are associated with disease processes.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Karposi's sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention pertains to inhibition of angiogenesis, per se, in a tissue. The extent of angiogenesis in a tissue, and therefore the extent of inhibition achieved by the present methods, can be evaluated by a variety of methods, such as are described in the Examples for detecting an ECRTP/DEP-1-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all vertebrate species, including mammals, which are intended to be included in the term "patient". In this context, a mammal is understood to include any mammalian species in which treatment of diseases associated with angiogenesis is desirable, particularly agricultural and domestic mammalian species.

The methods of the present invention are particularly useful in the treatment of warm-blooded vertebrates. Therefore, the invention concerns mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a hemangioma or angiofibroma and the like cancer, and the angiogenesis to be inhibited is tumor tissue angiogenesis where there is neovascularization of a tumor tissue.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor. Stated differently, the present invention provides for a method of modulating tumor neovascularization by modulating tumor angiogenesis according to the present methods. Similarly, the invention provides a method of modulating tumor growth by practicing the angiogenesis-modulating methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention pertains to the practice of the method in conjunction with other therapies such as conventional chemotherapy or surgery directed against solid tumors and for control of establishment of metastases. The administration of angiogenesis inhibitor can be conducted before, during or after chemotherapy or surgery. For example, the angiogenesis inhibition methods of the present invention can be practiced for chronic maintenance. As additional example, the angiogenesis inhibition methods of the present invention can be practiced after a regimen of chemotherapy at times where the tumor tissue will be responding to the toxic assault by inducing angiogenesis to recover by the provision of a blood supply and nutrients to the tumor tissue. As a further example, the angiogenesis inhibition methods of the present invention can be practiced after surgery where solid tumors have been removed as a prophylaxis against metastases.

The present method for modulating angiogenesis in a tissue contemplates contacting a tissue in which angiogenesis is occurring, or is at risk for occurring, with a composition comprising a therapeutically effective amount of an ECRTP/DEP-1 modulator capable of binding the ECRTP/DEP-1. Thus, the method comprises administering to a patient a therapeutically effective amount of a physiologically tolerable composition containing an ECRTP/DEP-1 modulator of the invention.

The dosage ranges for the administration of the ECRTP/DEP-1 modulator depend upon the form of the modulator, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective amount is an amount of an ECRTP/DEP-1 receptor modulator sufficient to produce a measurable inhibition of angiogenesis in the tissue being treated, i.e., an angiogenesis-modulating amount. Inhibition of angiogenesis can be measured in situ by immunohistochemistry, as described herein, or by other methods known to one skilled in the art.

Insofar as an ECRTP/DEP-1 modulator can take the form of an ECRTP/DEP-1 ligand mimetic, and an anti-ECRTP/DEP-1 monoclonal antibody, or fragment thereof, it is to be appreciated that the potency, and therefore an expression of a "therapeutically effective" amount can vary. However, as shown by the present assay methods, one skilled in the art can readily assess the potency of a candidate ECRTP/DEP-1 modulator of the present invention.

ECRTP/DEP-1 modulator can be measured by a variety of means including inhibition of angiogenesis in the mouse corneal assay for angiogenesis described herein, binding of natural ligand or monoclonal antibody to an ECRTP/DEP-1 as described herein, and the like assays.

A preferred ECRTP/DEP-1 modulator has the ability to substantially bind to an ECRTP/DEP-1 in solution at modulator concentrations of less than one (1) micro molar ($\mu$M), preferably less than 0.1 $\mu$M, and more preferably less than 0.01 $\mu$M. By "substantially" is meant that at least a 50 percent reduction in endothelial cell proliferation and migration is observed by modulation in the presence of the an ECRTP/DEP-1 modulator, and at 50% reduction is referred to herein as an IC50 value.

A therapeutically effective amount of an ECRTP/DEP-1 modulator of the present invention in the form of a monoclonal antibody, or fragment thereof, is typically an amount such that when administered in a physiologically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. For example, for Mab ECRTP/DEP-1 (MW=about 150 kDa), 10 $\mu$g/mL=67×10$^{-9}$ M. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

A therapeutically effective amount of an ECRTP/DEP-1 modulator of the present invention in the form of a polypeptide is typically an amount of polypeptide such that when administered in a physiologically tolerable composition is sufficient to achieve a plasma concentration of from about 0.001 microgram ($\mu$g) per milliliter (mL) to about 10 $\mu$g/mL, preferably from about 0.05 $\mu$g/mL to about 1.0 ug/mL. Based on a polypeptide having a mass of about 15,000 grams per mole (i.e. 15,000 Da), the preferred plasma concentration in molarity is from about 0.0001 micro molar ($\mu$M) to about 1 milli molar (mM). Stated differently, the dosage per body weight can vary from about 0.01 mg/kg to about 30 mg/kg, and preferably from about 0.05 mg/kg to about 20 mg/kg, in one or more dose administrations daily, for one or several days.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic means.

The therapeutic compositions containing a monoclonal antibody or a polypeptide of the present invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

C. Therapeutic Compositions

The present invention contemplates therapeutic compositions useful for practicing the therapeutic methods described herein. Therapeutic compositions of the present invention contain a physiologically tolerable carrier together with an ECRTP/DEP-1 modulator as described herein, dissolved or dispersed therein as an active ingredient. In a preferred embodiment, the therapeutic ECRTP/DEP-1 modulator composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-modulating amount of an ECRTP/DEP-1 modulator of the present invention, typically formulated to contain an amount of at least 0.1 weight percent of modulator per weight of total therapeutic composition. A weight percent is a ratio by weight of modulator to total composition. Thus, for example, 0.1 weight percent is 0.1 grams of inhibitor per 100 grams of total composition.

D. Modulators of ECRTP/DEP-1

ECRTP/DEP-1 modulators are used in the present methods for modulating ECRTP/DEP-1 activity in tissues, including modulating angiogenesis in tissues. Thus, as used herein, the terms "modulate", "modulating", and "modulator" are meant to be construed to encompass inhibiting, blocking, promoting, stimulating, agonising, antagonizing, or otherwise affecting ECRTP/DEP-1 activity in tissues.

Such modulators can take a variety of forms that include compounds which interact with the ECRTP/DEP-1 in a manner such that functional interactions with natural ECRTP/DEP-1 ligands are mimicked, stimulated and/or inhibited, such as, for example, dimerization of ECRTP/DEP-1. Exemplary modulators include analogs of an ECRTP/DEP-1 natural ligand binding site on an ECRTP/DEP-1, mimetics of a natural ligand of an ECRTP/DEP-1 that mimic the structural region involved in an ECRTP/DEP-1-receptor ligand binding interactions, polypeptides having a sequence corresponding to the domain of a natural ligand of an ECRTP/DEP-1, and antibodies which immunoreact with either an ECRTP/DEP-1 or the natural ligand, all of which exhibit modulator activity as defined herein.

1. Polypeptides

In one embodiment, the invention contemplates ECRTP/DEP-1 modulators in the form of polypeptides. A polypeptide (peptide) ECRTP/DEP-1 modulator interacts with the extracellular domain of ECRTP/DEP-1 and promotes dimerization of ECRTP/DEP-1. A preferred ECRTP/DEP-1 modulator peptide corresponds in sequence to the natural ligand and promotes or antagonizes dimerization of ECRTP/DEP-1 ECRTP/DEP-1.

In one embodiment, a polypeptide of the present invention comprises no more than about 100 amino acid residues, preferably no more than about 60 residues, more preferably no more than about 30 residues. Peptides can be linear or cyclic. Thus, it should be understood that a subject polypeptide need not be identical to the amino acid residue sequence of an ECRTP/DEP-1 natural ligand, so long as it includes required binding sequences and is able to function as an ECRTP/DEP-1 modulator in an assay such as is described herein.

A subject polypeptide includes any analog, fragment or chemical derivative of a polypeptide which is an ECRTP/DEP-1 modulator. Such a polypeptide can be subject to various changes, substitutions, insertions, and deletions where such changes provide for certain advantages in its use. In this regard, an ECRTP/DEP-1 modulator polypeptide of the present invention corresponds to, rather than is identical to, the sequence of the natural ligand where one or more changes are made and it retains the ability to function as an ECRTP/DEP-1 modulator in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of the natural ligand of the ECRTP/DEP-1 in which one or more residues have been conservatively substituted with a functionally similar residue and which displays the ECRTP/DEP-1 modulator activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as chemical derivatives are those peptides which contain one or more naturally occurring amino acid derivatives of the twenty standard amino acids. For examples: 4-hydroxyproline can be substituted for proline; 5-hydroxylysine can be substituted for lysine; 3-methylhistidine can be substituted for histidine; homoserine can be substituted for serine; and ornithine can be substituted for lysine. Polypeptides of the present invention also include any polypeptide having one or more additions and/or deletions or residues relative to the sequence of a polypeptide whose sequence is shown herein, so long as the requisite activity is maintained. The term "fragment" refers to any subject polypeptide having an amino acid residue sequence shorter than that of a polypeptide disclosed herein.

When a polypeptide of the present invention has a sequence that is not identical to the sequence of an ECRTP/DEP-1 natural ligand, it is typically because one or more conservative or non-conservative substitutions have been made, usually no more than about 30 number percent, and preferably no more than 10 number percent of the amino acid residues are substituted. Additional residues can also be added at either terminus of a polypeptide for the purpose of providing a "linker" by which the polypeptides of the present invention can be conveniently affixed to a label or solid matrix, or carrier. Labels, solid matrices and carriers that can be used with the polypeptides of the present invention are described hereinbelow.

Amino acid residue linkers are usually at least one residue and can be 40 or more residues, more often 1 to 10 residues, but do not form ECRTP/DEP-1 ligand epitopes. Typical amino acid residues used for linking are tyrosine, cysteine, lysine, glutamic and aspartic acid, or the like. In addition, a subject polypeptide can differ, unless otherwise specified, from the natural sequence of an ECRTP/DEP-1 ligand by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases can be present. In this regard, polypeptide cyclization is also a useful terminal modification, and is particularly preferred also because of the stable structures formed by cyclization and in view of the biological activities observed for such cyclic peptides as described herein.

Any peptide of the present invention can be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv Enzymol, 32:221–96, 1969; Fields et al., Int. J. Peptide Protein Res., 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above can be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

2. Antibodies

The present invention describes, in one embodiment, ECRTP/DEP-1 modulators in the form of antibodies, including monoclonal antibodies, which immunoreact with an ECRTP/DEP-1 and bind the ECRTP/DEP-1 to modulate receptor activity as described herein. The invention also describes cell lines which produce the antibodies, methods for producing the cell lines, and methods for producing the antibodies, including monoclonal antibodies.

An antibody of the present invention can comprise an antibody molecule that 1) immunoreact with isolated ECRTP/DEP-1, and 2) bind to the ECRTP/DEP-1 to modulate its biological function. Preferably, an antibody of the present invention preferentially binds the ECRTP/DEP-1 ectodomain, which comprises amino acids 1–351 of ECRTP/DEP-1. More preferably, an antibody of the present invention preferentially binds an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein, of the ECRTP/DEP-1 ectodomain.

Preferred monoclonal antibodies which preferentially bind to ECRTP/DEP-1 include a monoclonal antibody having the immunoreaction characteristics of Mab ECRTPAb-1, having molecular weight of about 150 KDa respectively and which binds to the ectodomain of the ECRTP/DEP-1, as is described herein below. Mab ECRTPAb-1 is preferably secreted by hybridoma cell line ATCC HB12570. The hybridoma cell line ATCC HB12570 was deposited pursuant to Budapest Treaty requirements with the American Type Culture Collection (ATCC), 10801 University Boulevard, Manassas, Va., 20110-2209, U.S.A., on Sep. 18, 1998.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments.

Indeed, as described in the Examples set forth below, an Fab fragment, that is, a monovalent fragment, of the Mab ECRTPAb-1 releases density arrest. Thus, it is contemplated to be within the scope of the present invention that such a monovalent modulator is used to promote angiogenesis, or to promote endothelial cell migration and proliferation, or to release inhibitory influences on endothelial cells to serve as an adjunctive to other angiogenic stimuli. Thus, the terms "modulate", "modulating", and "modulator" are meant to be construed to encompass such promotion.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody can therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. Additional methods are described by Zola, *Monoclonal Antibodies: a Manual of Techniques*, CRC Press, Inc. (1987). The hybridoma supernates so prepared can be screened for the presence of antibody molecules that immunoreact with an ECRTP/DEP-1 and for inhibition of an ECRTP/DEP-1 to activate its biological function.

Briefly, to form the hybridoma from which the monoclonal antibody composition is produced, a myeloma or other self-perpetuating cell line is fused with lymphocytes obtained from the spleen of a mammal hyperimmunized with a source of an ECRTP/DEP-1, as described by Cheresh et al., *J. Biol Chem,* 262:17703–17711 (1987).

It is preferred that the myeloma cell line used to prepare a hybridoma be from the same species as the lymphocytes. Typically, a mouse of the strain 129 GIX+ is the preferred mammal. Suitable mouse myelomas for use in the present invention include the hypoxanthine-aminopterin-thymidine-sensitive (HAT) cell lines P3×63-Ag8.653, and Sp2/0-Ag14 that are available from the ATCC, Manassas, Va., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of the present invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques. Media useful for the preparation of these compositions are both well known in the art and commercially available and include synthetic culture media, inbred mice and the like. An exemplary synthetic medium is Dulbecco's minimal essential medium (DMEM—Dulbecco et al., *Virol* 8:396 (1959)) supplemented with 4.5 gm/1 glucose, 20 mM glutamine, and 20% fetal calf serum. An exemplary inbred mouse strain is the Balb/C.

Other methods of producing a monoclonal antibody, a hybridoma cell, or a hybridoma cell culture are also well known. See, for example, the method of isolating monoclonal antibodies from an immunological repertoire as described by Sastry, et al., *Proc Natl Acad Sci USA* 86:5728–5732 (1989); and Huse et al., *Science* 246:1275–1281 (1989).

Also contemplated by the present invention is the hybridoma cell, and cultures containing a hybridoma cell that produce a monoclonal antibody of the present invention. Particularly preferred is the hybridoma cell line that secretes monoclonal antibody Mab ECRTPAb-1 as described in the Examples presented below and as designated ATCC HB12570. Mab ECRTPAb-1 was prepared as described in the Examples. The invention thus contemplates, in one embodiment, a monoclonal antibody that has the immunoreaction characteristics of Mab ECRTPAb-1.

It is also possible to determine, without undue experimentation, if a monoclonal antibody has the same (i.e., equivalent) specificity (immunoreaction characteristics) as a monoclonal antibody of the present invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope. A preferred target molecule comprises a polypeptide fragment of the ECRTP/DEP-1 ectodomain includes an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention. A preferred target molecule comprises a polypeptide fragment of the ECRTP/DEP-1 ectodomain includes an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule. Preferably, an antibody of the present invention preferentially binds an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein, of the ECRTP/DEP-1 ectodomain.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of the present invention that is humanized by grafting to introduce components of the human immune system without substantially interfering with the ability of the antibody to bind antigen. Humanized antibodies can also be produced using animals engineering to produce humanized antibodies, such as those available from Medarex of Annandale, N.J. (mice) and Abgenix, Inc., of Fremont, Calif. (mice).

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid or phage-displayed libraries are prepared from RNA isolated from the spleen of the immunized animal, and phagemids expressing appropriate antibodies are selected by panning on endothelial tissue. This approach can also be used to prepared humanized antibodies. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein, such as ECRTP/DEP-1. Preferably, an antibody of the present invention preferentially binds an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein, of the ECRTP/DEP-1 ectodomain.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Antibodies*, vol. 113, Rosenburg and Moore eds., Springer-Verlag, New York, pp. 269–315 (1994).

Using a phage-displayed approach for the production of antibodies, scFv antibody clones that bind to the ECRTP/DEP-1 ectodomain have been identified. This was accomplished by competing off those phage displayed antibodies using ECRTPAb-1 disclosed herein. Fv regions are sequenced an bivalent functional reagents are designed and tested in a screening assay of the present invention disclosed herein below. Thus, a preferred source for an antibody, or derivative or fragment thereof, is a recombinant phage-displayed antibody library. The recombinant phage can comprise antibody encoding nucleic acids isolated from any suitable vertebrate species, including mammalian species such as mouse and rat; but preferably comprises antibody encoding nucleic acids isolated from human. Such antibodies are thus already "humanized".

3. Other Modulators

It is also envisioned that previously described and newly discovered angiogenesis inhibiting or endothelial cell growth suppressing chemical compounds are modulators of ECRTP/DEP-1 activity in tissues. Examples of such compounds include, but are not limited to, angiostatin, endostatin and thrombospondin. Accordingly, such compounds can be used in the modulation of ECRTP/DEP-1 activity in tissues, according to the methods of the present invention.

Given the disclosure of the ECRTP/DEP-1 activity in tissues herein, it is also contemplated that as yet undefined chemical compounds can be used to modulate ECRTP/DEP-1 activity in tissues in accordance with the methods of the present invention. In one embodiment, a modulator of the present invention interacts with an eight amino acid epitope having the sequence n-QSRDTEVL-c (SEQ ID NO: 1) of the ECRTP/DEP-1 ectodomain. The identification of such modulators is provided through the description of screening assays directed to ECRTP/DEP-1 activity in tissues presented herein.

D. Screening Assay

Skilled artisans will understand that the disclosure herein of the localization and function of the ECRTP/DEP-1, and in vitro assays relating to such localization and function, provides opportunities to screen for compounds that modulate, whether partially or completely, the functional activity of the ECRTP/DEP-1. In this context, "modulate" is intended to mean that the subject compound increases or decreases one or more functional activities of the ECRTP/DEP-1, such as but not limited to ECRTP/DEP-1 activity in cell growth, cell survival and angiogenesis.

Further, the screening assays illustrated in the Examples below include biochemical assays (e.g., measuring effects of anti-ECRTP/DEP-1 monoclonal antibodies on ECRTP/DEP-1 activity), and cellular in vitro assays (e.g., measuring the effects of ECRTP/DEP-1 over-expression on endothelial cell proliferation and migration and/or evaluating ECRTP/DEP-1 phosphorylation). The illustrative biochemical assays can be particularly useful in screening for compounds modulating an ECRTP/DEP-1 activity, while the cellular assays can be particularly useful in screening for compounds completely altering an ECRTP/DEP-1 activity. Thus, until the disclosure herein of the role of the ECRTP/DEP-1 in regulating cell growth, cell survival, endothelial cell proliferation and migration and in regulating angiogenesis, a motivation to screen for compounds that modulate ECRTP/DEP-1 activity was lacking in the prior art.

Those skilled in the art will understand that binding of a ligand at a molecular binding site can be modulated in a direct matter (e.g., by blocking the site), as well as modulated in an indirect manner (e.g., by conformational changes induced following binding of a second, i.e., different, ligand at a distant site). In this regard, it is likely that the binding site specificity of an ECRTP/DEP-1 for its endogenous ligand can be completely modulated or altered (i.e., to bind a different ligand) by agents that bind at distant sites in the ECRTP/DEP-1. Examples of compounds that can be screened in the latter several assays include at least nucleic acids (e.g., DNA oligonucleotide aptamers that bind proteins and alter their functions), proteins, antibodies and antibody fragments, carbohydrates, lectins, organic chemicals, and the like. Such screening assays can be useful for identifying candidate therapeutic agents that can provide drugs useful in animals and humans.

It is still further understood that due to the significance of the ECRTP/DEP-1 in cell growth, cell survival, endothelial cell migration and proliferation, in density induced growth arrest, and in modulation of angiogenesis, innate regulatory mechanisms exist in cells for regulating their activity by binding to an ECRTP/DEP-1, or to complexes containing an ECRTP/DEP-1. Such regulatory factors can include, at least: (a) cofactors that bind to the complex and exert regulatory action by destabilizing or stabilizing the complex; (b) agents that modulate or alter the activity of the complex by inducing conformational changes in the ECRTP/DEP-1 as they are bound in a complex; (c) enzymes that inactivate one or both members of a complex; and (d) cellular control factors (e.g., signal transduction second messengers, transcription regulating factors, DNA replication factors and the like) that bind an ECRTP/DEP-1 or ECRTP/DEP-1 complexes and modulate or alter functional activity. Those skilled in the art will recognize that the functional regions of an ECRTP/DEP-1 represent particularly attractive targets for three-dimensional molecular modeling and for construction of mimetic compounds, e.g., organic chemicals constructed to mimic the three-dimensional interactions between the ECRTP/DEP-1 and its endogenous binding partner, or other binding partner.

Utilizing the methods and compositions of the present invention, screening assays for the testing of candidate substances can be derived. A candidate substance is a substance which potentially can modulate endothelial cell growth, cell survival, cell migration and proliferation, density induced growth arrest and/or angiogenesis, and/or ECRTP/DEP-1 phosphorylation, by binding or other intramolecular interaction, with an ECRTP/DEP-1 that modulates endothelial cell growth, cell survival, cell migration and proliferation, density induced growth arrest and angiogenesis.

Thus, a method of screening candidate substances for an ability to modulate ECRTP/DEP-1 biological activity is also disclosed. The method comprises establishing a test sample comprising an ECRTP/DEP-1 polypeptide or fragment thereof; administering a candidate substance to the test sample; and measuring the interaction, effect, or combination thereof, of the candidate substance on the test sample to thereby determine the ability of the candidate substance to modulate ECRTP/DEP-1 biological activity.

The present invention also provides a process of screening substances for their ability to modulate or alter cell growth, cell survival, endothelial cell migration and proliferation, density induced growth arrest and/or angiogenesis and/or ECRTP/DEP-1 phosphorylation comprising the steps of providing a cell that contains a functional ECRTP/DEP-1 and testing the ability of selected substances to modulate or alter cell growth, cell survival, migration or proliferation of that cell, density induced growth arrest of the cell, or initiation of angiogenesis in the cell and/or evaluating ECRTP/DEP-1 phosphorylation in the cell.

A screening assay of the present invention generally involves determining the ability of a candidate substance to affect cell growth, cell survival, endothelial cell migration and proliferation, density induced growth arrest and/or angiogenesis, and/or ECRTP/DEP-1 phosphorylation in a target cell, such as the screening of candidate substances to identify those that modulate or alter cell growth, cell survival, endothelial cell migration and proliferation, density induced growth arrest and/or angiogenesis, and/or ECRTP/DEP-1 phosphorylation. Target cells can be either naturally occurring cells known to contain an ECRTP/DEP-1 or transfected cell produced in accordance with a process of transfection set forth herein and as are known in the art.

Thus, in one embodiment a method of screening a candidate substance for an ability to modulate a receptor tyrosine phosphatase in accordance with the present invention comprises establishing test samples comprising a receptor tyrosine phosphatase polypeptide; and administering a candidate substance to the test samples; measuring the interaction, effect, or combination thereof, of the candidate substance on the test sample to thereby determine the ability of the candidate substance to modulate receptor tyrosine phosphatase biological activity. A preferred receptor tyrosine phosphatase comprises ECRTP/DEP-1.

In another embodiment, a method of screening a candidate substance for an ability to modulate a receptor tyrosine phosphatase in accordance with the present invention comprises establishing a test sample comprising a receptor tyrosine phosphatase; administering a candidate substance to the test sample; and measuring a receptor tyrosine phosphatase biological activity in the test sample; detecting phosphotyrosine residues on the receptor tyrosine phosphatase; and determining that the candidate substance modulates the receptor tyrosine phosphatase if the receptor tyrosine phosphatase biological activity measured for the test sample is greater or less than the receptor tyrosine phosphatase biological activity measured for a control sample and if the amount of phosphotyrosine residues on the receptor tyrosine phosphatase is greater or less than an amount of phosphotyrosine residues on a receptor tyrosine phosphate derived from a control sample. A preferred receptor tyrosine phosphatase comprises ECRTP/DEP-1.

In yet another embodiment, a method of screening a candidate substance for an ability to modulate a receptor tyrosine phosphatase in accordance with the present invention comprises establishing replicate test and control cultures of cells that express the ECRTP/DEP-1; administering a candidate compound to the cells in the test culture but not the control culture; measuring ECRTP/DEP-1 activity in cells in the test and the control cultures; and determining that the candidate compound modulates the ECRTP/DEP-1 activity in a cell if the ECRTP/DEP-1 activity measured for the test culture is greater or less than the ECRTP/DEP-1 activity measured for the control culture.

The screening assay methods of the present invention also pertain to comparing the effect of a candidate compound to inhibit growth of cells expressing exogenous ECRTP/DEP-1 compared with those not expressing ECRTP/DEP-1 and determining that the effect of altering ECRTP/DEP-1 activity is responsible by demonstrating the lack of activity of the candidate compound on cells not expressing ECRTP/DEP-1. The screening assays of the present invention show changes in growth that are responsive to changes in ECRTP/DEP-1 activity. For example, the screening methods of the present invention are used to screen for biologically active counter-receptors (ligands) by screening for growth inhibitory activity in biological fractions (plasma, cell lysates, cell membrane extracted proteins) by comparing growth inhibition on CHO/ECRTP/DEP-1 to CHO parent cell lines.

In a cell-free system, a method of screening a candidate substance for an ability to modulate a receptor tyrosine phosphatase in accordance with the present invention comprises establishing a control system comprising an ECRTP/DEP-1, or fragment thereof and a ligand wherein the ECRTP/DEP-1 is capable of binding to the ligand; establishing a test system comprising the ECRTP/DEP-1, the ligand, and a candidate compound; measuring the binding affinity of the ECRTP/DEP-1 and the ligand in the control and the test systems; and determining that the candidate compound modulates ECRTP/DEP-1 activity in a cell-free system if the binding affinity measured for the test system is less than or greater than the binding affinity measured for the control system. Optionally, the ligand comprises an antibody which preferentially binds the ECRTP/DEP-1. In this case, it is preferred that the ligand comprise a monoclonal antibody.

In accordance with the present invention, a method of affinity screening of candidate modulator substances, including but not limited to antibodies, is provided. The method comprises: (a) contacting a candidate modulator substance with an ECRTP/DEP-1 polypeptide or fragment thereof under conditions favorable to binding the candidate modulator substance with an ECRTP/DEP-1 polypeptide or fragment thereof to form a complex therebetween; and (b) detecting the complex.

The complex can be detected in any suitable manner. For example, the complex can be detected via a label conjugated to the ECRTP/DEP-1 polypeptide or fragment thereof; via a labeled reagent that specifically binds to the complex subsequent to its formation; or via a competition assay with a substance. The ECRTP/DEP-1 polypeptide fragment can be a ECRTP/DEP-1 ectodomain fragment. Preferably, the ECRTP/DEP-1 ectodomain fragment comprises an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein. Optionally, the ECRTP/DEP-1 polypeptide or fragment thereof is conjugated with a detectable label. In this case, the detecting step comprises: (i) separating the complex from unbound labeled binding substance; and (ii) detecting the detectable label which is present in the complex or which is unbound.

An antibody, or derivative or fragment thereof, can be screened as a candidate modulator substance. As noted above, a preferred source for an antibody, or derivative or fragment thereof, is a recombinant phage-displayed antibody library. The recombinant phage can comprise antibody encoding nucleic acids isolated from any suitable vertebrate species, including mammalian species such as mouse and rat; but preferably comprises antibody encoding nucleic acids isolated from human. Such antibodies are thus already "humanized".

In another aspect, the present invention pertains to a kit for use in the aforementioned affinity screening method. The kit comprises a binding agent comprising a polypeptide fragment of the ECRTP/DEP-1 ectodomain that comprises an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein, contained in a first container.

The kit can further comprise a reagent or indicator that comprises a detectable label, the indicator containing in another container. Alternatively, the binding agent can comprise a detectable label or indicator. Preferably, the indicator is a radioactive label or an enzyme, or other suitable indicator.

Another technique for drug screening which can be used provides for high throughput screening of compounds having suitable binding affinity to the protein of interest as described in published PCT application WO 84/03564, herein incorporated by reference. In this method, as applied to the ECRTP/DEP-1 polypeptide, large numbers of different small test compounds are synthesized on a solid substrate, such as plastic pins or some other surface. The test compounds are reacted with the ECRTP/DEP-1 polypeptide, or fragments thereof, and washed. Bound ECRTP/DEP-1 polypeptide is then detected by methods well known in the art. Purified ECRTP/DEP-1 polypeptide can also be coated directly onto plates for use in the aforementioned drug screening techniques. Alternatively, non-neutralizing antibodies can be used to capture the peptide and immobilize it on a solid support.

A screening assay of the present invention can also involve determining the ability of a candidate substance to modulate, i.e. inhibit or promote ECRTP/DEP-1 biological activity and preferably, to thereby modulate the ECRTP/DEP-1 biological activity in target cells. Target cells can be either naturally occurring cells known to contain a polypeptide of the present invention or transfected cells produced in accordance with a process of transfection set forth herein above. The test samples can further comprise a cell or cell line that expresses the ECRTP/DEP-1; the present invention also contemplates a recombinant cell line suitable for use in the exemplary method. Such cell lines can be mammalian, or human, or they can from another organism, including but not limited to yeast. Exemplary assays including genetic screening assays and molecular biology screens such as a yeast two-hybrid screen that will effectively identify ECRTP/DEP-1-interacting genes important for endothelial cell migration and proliferation, density induced growth arrest, angiogenesis or other ECRTP/DEP-1-mediated cellular process. One version of the yeast two-hybrid system has been described (Chien et al., 1991, *Proc. Natl. Acad. Sci. USA*, 88:9578–9582) and is commercially available from Clontech (Palo Alto, Calif.).

A method of identifying modulators of the ECRTP/DEP-1 by rational drug design is also provided in accordance with the present invention. The method comprises the steps of designing a potential modulator for the ECRTP/DEP-1 that will form non-covalent bonds with amino acids in the substrate binding site in the catalytic domain (an intracellular site) or with the ECRTP/DEP-1 ectodomain based upon the structure of the ECRTP/DEP-1; synthesizing the modulator; and determining whether the potential modulator modulates the activity of the ECRTP/DEP-1.

Thus, the present invention pertains to screening and rational drug design methods for both ectodomain interactions, as well as catalytic modulators. For example, catalytic antagonists that release cells from growth arrest through modulation of the catalytic function independent of the ectodomain can be screened and designed. Additionally, a modulator of the present invention can be screened for interaction with an eight amino acid epitope having the sequence n-QSRDTEVL-c (SEQ ID NO: 1), or an eight amino acid epitope having an analog sequence of the sequence n-QSRDTEVL-c (SEQ ID NO: 1), the term "analog" as defined herein, of the ECRTP/DEP-1 ectodomain.

Modulators can be synthesized using techniques disclosed herein and as are known in the art. The determination of whether the modulator modulates the biological activity of the ECRTP/DEP-1 is made in accordance with the screening methods disclosed herein, or by other screening methods known in the art.

As is well known in the art, a screening assay provides a cell under conditions suitable for testing modulation or alteration of cell growth, cellendothelial cell migration and proliferation, density induced growth arrest, angiogenesis, and/or ECRTP/DEP-1 phosphorylation. These conditions include but are not limited to pH, temperature, tonicity, the presence of relevant factors involved in the cell cycle (e.g., growth factors), and relevant modifications to the polypeptide such as glycosylation or prenylation. It is contemplated that an ECRTP/DEP-1 can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of endothelial cell migration and proliferation, density induced growth arrest and/or angiogenesis in specific cells. Such factors include, for example, the presence and absence (withdrawal) of growth factor, interleukins, or colony stimulating factors.

E. Methods for Identifying Modulators of an ECRTP/DEP-1

The invention thus also pertains to assay methods for identifying candidate ECRTP/DEP-1 modulators. In these assay methods candidate molecules are evaluated for their potency in agonising an ECRTP/DEP-1 binding to natural ligands, and furthermore are evaluated for their potency in modulating angiogenesis in a tissue.

An exemplary assay measures angiogenesis in the chick chorioallantoic membrane (CAM) and is referred to as the CAM assay. The CAM assay has be described in detail by others, and further has been used to measure both angiogenesis and neovascularization of tumor tissues. See Ausprunk et al., *Am J Pathol* 79:597–618 (1975) and Ossonski et al., *Cancer Res* 40:2300–2309 (1980).

The CAM assay is a well recognized assay model for in vivo angiogenesis because neovascularization of whole tissue is occurring, and actual chick embryo blood vessels are growing into the CAM or into the tissue grown on the CAM. The CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

F. Preparation of Targeting Agent/Toxin Compounds, Including Immunotoxins

Methods for the production of the target agent/toxin agent compounds of the invention are described herein. The targeting agents, such as antibodies, of the invention can be linked, or operatively attached, to the toxins of the invention by either crosslinking or via recombinant DNA techniques, to produce, for example, targeted immunotoxins.

While the preparation of immunotoxins is, in general, well known in the art (se e.g., U.S. Pat. Nos. 4,340,535 and 5,776,427, and EP 44167, each of which incorporated herein by reference), certain advantages can be achieved through the application of certain preferred technology, both in the preparation of the immunotoxins and in their purification for subsequent clinical administration. For example, while numerous types of disulfide-bond containing linkers are known which can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

A wide variety of cytotoxic agents are known that can be conjugated to anti-endothelial cell antibodies. Examples include numerous useful plant-, fungus- or even bacteria-derived toxins, which, by way of example, include various A chain toxins, particularly ricin A chain, ribosome inactivating proteins such as saporin or gelonin, a-sarcin, aspergillin, restrictocin, ribonucleases such as placental ribonuclease, angiogenic, diphtheria toxin, and pseudomonas exotoxin, to name just a few.

However, it can be desirable from a pharmacologic standpoint to employ the smallest molecule possible that nevertheless provides an appropriate biological response. One can thus desire to employ smaller-chain peptides which will provide an adequate anti-cellular response.

Alternatively, one can find that the application of recombinant DNA technology to the toxin moiety will provide additional significant benefits in accordance the invention. For example, the cloning and expression of biologically active toxin candidates has now been described through the publications of others (O'Hare et al., *FEBS Lett* 210:731 (1987); Lamb et al., *Eur Jrnl Biochem* 148:265–270 (1985); Hailing et al., *Nucl Acids Res* 13:8019–8033 (1985)), it is now possible to identify and prepare smaller or otherwise variant peptides which nevertheless exhibit an appropriate toxin activity. Moreover, the use of cloned toxin candidates allows the application of site-directed mutagenesis, through which one can readily prepare and screen for mutated peptides and obtain additional useful moieties for use in connection with the present invention.

In cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including the particular cross-linking reagent used and the structures that are cross-linked, will be of some significance.

Cross-linking reagents are used to form molecular bridges that tie together functional groups of two different proteins (e.g., a toxin and a binding agent). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., the selected antibody or fragment) and through the thiol reactive group, the cross-linker, already tied up to the first protein, reacts with the cysteine residue (free sulfhydryl group) of the other protein.

The spacer arm between these two reactive groups of any cross-linkers can have various length and chemical composition. A longer spacer arm allows a better flexibility of the conjugate components while some particular components in the bridge (e.g., benzene group) can lend extra stability to the reactive group or an increased resistance of the chemical link to the action of various aspects (e.g., disulfide bond resistant to reducing agents).

An exemplary cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Thorpe et al., *Cancer Res* 47:5924–5931 (1987)). The use of such cross-linkers is well understood in the art.

Once conjugated, it will be important to purify the conjugate so as to remove contaminants such as unconjugated toxin or targeting agent. It is important to remove unconjugated targeting agent to reduce undesired toxicity and to avoid the possibility of competition for the antigen between conjugated and unconjugated species. In general, the most preferred purification technique will incorporate the use of Blue-Sepharose with a gel filtration or gel permeation step. Blue-Sepharose is a column matrix composed of Cibacron Blue 3GA and agarose, which has been found to be useful in the purification of immunoconjugates (Knowles & Thorpe, *Anal. Biochem* 120:440–443 (1987)). The use of Blue-Sepharose combines the properties of ion exchange with toxin binding to provide good separation of conjugated toxin from non-conjugated toxin. The Blue-Sepharose column allows the elimination of the free (non-conjugated) targeting agent (e.g., the antibody or fragment) from the conjugate preparation. To eliminate the free (non-conjugated) toxin a molecular exclusion chromatography step is preferred using either conventional gel filtration procedure or high performance liquid chromatography.

Standard recombinant DNA techniques that are well known to those of skill in the art can be utilized to express nucleic acids encoding the targeting agent/toxin compounds of the invention. These methods include, for example, in vitro recombinant DNA techniques, synthetic techniques and in vivo recombination/genetic recombination. DNA and RNA synthesis can, additionally, be performed using an automated synthesizers (see, for example, the techniques described in Sambrook et al., Molecular Cloning, A Laboratory Manual, Cold Spring Harbor Laboratory, New York (1989); and Ausubel et al., Current Protocols in Molecular Biology, Greene Publishing Associates and Wiley Interscience, New York (1989).

When produced via recombinant DNA techniques such as those described herein, the targeting agent/toxin compounds of the invention can be referred to herein as "fusion proteins". It is to be understood that such fusion proteins contain at least a targeting agent and a toxic moiety operatively attached, such that the fusion protein can be used in accordance with the methods of the present invention. The fusion proteins can also include additional peptide sequences, such as peptide spacers which operatively attach the targeting agent and toxin compound, as long as such additional sequences do not appreciably affect the targeting or toxin activities of the fusion protein.

Depending on the specific toxin compound used as part of the fusion protein, it can be necessary to provide a peptide spacer operatively attaching the targeting agent and the toxin compound which is capable of folding into a disulfide-bonded loop structure. Proteolytic cleavage within the loop would then yield a heterodimeric polypeptide wherein the targeting agent and the toxin compound are linked by only a single disulfide bond. See e.g., Lord et al., In *Genetically Engineered Toxins* (Ed. A. Frank, M. Dekker Publ., p. 183) (1992). An example of such a toxin is a Ricin A-chain toxin.

When certain other toxin compounds are utilized, a non-cleavable peptide spacer can be provided to operatively attach the targeting agent and the toxin compound of the fusion protein. Toxins which can be used in conjunction with non-cleavable peptide spacers are those which can, themselves, be converted by proteolytic cleavage, into a cytotoxic disulfide-bonded form (see e.g., Ogata et al., *J Biol Chem* 256:20678–20685 (1990)). An example of such a toxin compound is a *Pseudomonas* exotoxin compound.

Nucleic acids that can be utilized herein comprise nucleic acid sequences that encode a targeting agent of interest and nucleic acid sequences that encode a toxin agent of interest. Such target agent-encoding and toxin agent-encoding nucleic acid sequences are attached in a manner such that translation of the nucleic acid yields the targeting agent/toxin compounds of the invention.

Standard techniques, such as those described above can be used to construct expression vectors containing the above-described nucleic acids and appropriate transcriptional/translational control sequences. A variety of host-expression vector systems can be utilized. These include but are not limited to microorganisms such as bacteria (e.g., *E. coli, B. subtilis*) transformed with recombinant bacteriophage DNA, plasmid DNA or cosmid DNA expression vectors containing targeting agent/toxin coding sequences; yeast (e.g., *Saccharomyces, Pichia*) transformed with recombinant yeast expression vectors containing targeting agent/toxin coding sequences; insect cell systems infected with recombinant virus expression vectors (e.g., baculovirus) containing the targeting agent/toxin coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the targeting agent/toxin coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; lentiviral vectors).

In bacterial systems a number of expression vectors can be advantageously selected depending upon the use intended for the targeting agent/toxin compound being expressed. For example, when large quantities of targeting agent/toxin compound are to be produced for the generation of antibodies or to screen peptide libraries, vectors which direct the expression of high levels of fusion protein products that are readily purified can be desirable. Such vectors include but are not limited to the *E. coli* expression vector pUR278 (Ruther et al., *EMBO J.* 2:1791 (1983)), in which the targeting agent/toxin coding sequence can be ligated individually into the vector in frame with the lac Z coding region so that a fusion protein additionally containing a portion of the lac Z product is provided; pIN vectors (Inouye et al., *Nucleic Acids Res* 13:3101–3109 (1985); Van Heeke et al., *J Biol Chem* 264:5503–5509 (1989)); and the like. pGEX vectors can also be used to express foreign polypeptides, such as the targeting agent/toxin compounds as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the targeting agent/toxin protein of the fusion protein can be released from the GST moiety.

In an insect system, Autograph californica nuclear polyhidrosis virus (AcNPV) is used as a vector to express foreign genes. The virus grows in *Spodoptera frugiperda* cells. The targeting agent/toxin coding sequences can be cloned into non-essential regions (for example the polyhedrin gene) of the virus and placed under control of an AcNPV promoter (for example the polyhedrin promoter). Successful insertion of the targeting agent/toxin coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see e.g., Smith et al., *J Virol* 46:584 (1983); U.S. Pat. No. 4,215,051).

In mammalian host cells, a number of viral based expression systems can be utilized. In cases where an adenovirus is used as an expression vector, the targeting agent/toxin coding sequences can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing targeting agent/toxin proteins in infected hosts (see e.g., Logan et al., *Proc Natl Acad Sci USA* 81:3655–3659 (1984)). Specific initiation signals can also be required for efficient translation of inserted targeting agent/toxin coding sequences. These signals include the ATG initiation codon and adjacent sequences. Exogenous translational control signals, including the ATG initiation codon, can additionally need to be provided. One of ordinary skill in the art would readily be capable of determining this and providing the necessary signals. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., *Methods in Enzymol* 153:516–544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, etc. For long-term, high-yield production of recombinant proteins, stable expression is preferred. For example, cell lines which stably express constructs encoding the targeting agent/toxin compounds can be engineered. Rather than using expression vectors which contain viral origins of replication, host cells can be transformed with targeting agent/toxin DNA controlled by appropriate expression control elements (e.g., promoter, enhancer, sequences, transcription terminators, polyadenylation sites, etc.), and a selectable marker. Following the introduction of foreign DNA, engineered cells can be allowed to grow for one or two (1–2) days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems can be used, including, but not limited to, the herpes simplex virus thymidine kinase (Wigler et al., *Cell* 11:223 (1977)), hypoxanthine-guanine phosphoriboxyltransferase (Szybalska et al., *Proc Natl Acad Sci USA* 48:2026 (1962)), and adenine phosphoribosyltransferase genes (Lowy et al., *Cell* 22:817 (1980)) can be employed in tk-, hgprt- or aprt-cells, respectively. Also, antimetabolite resistance can be used as the basis of selection for dhfr, which confers resistance to methotrexate (Wigler et al., *Proc Natl Acad Sci USA* 77:3567 (1980); O'Hare et al., *Proc Natl Acad Sci USA* 78:1527 (1981)); gpt, which confers resistance to mycophenolic acid (Mulligan et al., *Proc Natl Acad Sci USA* 78:2072 (1981)); neo, which confers resistance to the aminoglycoside G-418 (Colberre-Garapin et al., *J Mol Biol* 150:1 (1981)); and hygro, which confers resistance to hygromycin (Santerre et al., *Gene* 30:147 (1984)).

After a sufficiently purified compound has been prepared, one will desire to prepare it into a pharmaceutical composition that can be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/mL with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences*, 16th Ed. Mack Publishing Company (1980), incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

A preferred parenteral formulation of the targeting agent/toxin compounds, including immunotoxins, in accordance with the present invention is 0.25 to 2.5 mg conjugate/mL in 0.15M NaCl aqueous solution at pH 7.5 to 9.0. The preparations can be stored frozen at $-10°$ C. to $-70°$ C. for at least one (1) year.

G. Attachment of Other Agents to Targeting Agents

It is contemplated that most therapeutic applications of the present invention will involve the targeting of a toxin moiety to the endothelium, particularly tumor endothelium. This is due to the much greater ability of most toxins to deliver a cell killing effect as compared to other potential agents. However, there can be circumstances, such as when the target antigen does not internalize by a route consistent with efficient intoxication by targeting agent/toxin compounds, such as immunotoxins, where one will desire to target chemotherapeutic agents such as antitumor drugs, other cytokines, antimetabolites, alkylating agents, hormones, and the like. The advantages of these agents over their non-targeting agent conjugated counterparts is the added selectivity afforded by the targeting agent, such as an antibody. Exemplary agents include, but are not limited to, such as steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to targeting agents, such as antibodies, for specific delivery to tissues is well established.

It is proposed that particular benefits can be achieved through the application of the invention to tumor imaging. Imaging of the tumor vasculature is believed to provide a major advantage when compared to present imaging techniques, in that the cells are readily accessible. Moreover, the technology for attaching paramagnetic, radioactive and even fluorogenic ions to targeting agents, such as antibodies, is well established. Many of these methods involve the use of a metal chelate complex employing, for example, an organic chelating agent such a DTPA attached to the antibody. See e.g., U.S. Pat. No. 4,472,509. In the context of the present invention the selected ion is thus targeted to the tumor endothelium by the targeting agent, such as an antibody, allowing imaging to proceed by means of the attached ion.

A variety of chemotherapeutic and other pharmacologic agents have now been successfully conjugated to antibodies and shown to function pharmacologically (see e.g., Vaickus et al., *Cancer Invest* 9:195–209 (1991)). Exemplary antineoplastic agents that have been investigated include doxorubicin, daunomycin, methotrexate, vinblastine, and various others. Dillman et al., *Antibody Immunocon Radiopharm* 1:65–77 (1988); Pietersz et al., *Antibody Immunoconj Radiopharm* 1:79–103 (1988). Moreover, the attachment of other agents such as neocarzinostatin (Kimura et al., *Immunogenetics* 11:373–381 (1980)), macromycin, trenimon (Ghose et al., *Meth. Enzymology* 93:280–333 (1983)) and α-amanitin has been described.

In addition to chemotherapeutic agents, the invention is contemplated to be applicable to the specific delivery of a wide variety of other agents to tumor vasculature. For example, under certain circumstances, one can desire to deliver a coagulant such as Russell's Viper Venom, activated Factor IX, activated Factor X or thrombin to the tumor vasculature. This will result in coagulation of the tumor's blood supply. One can also envisage targeting a cell surface lytic agent such as phospholipase C, (Flickinger & Trost, *Eu. J. Cancer* 12(2):159–60 (1976)) or cobra venom factor (CVF) (Vogel & Muller-Eberhard, *Anal. Biochem* 118(2): 262–268 (1981)) which should lyse the tumor endothelial cells directly. The operative attachment of such structures to targeting agents, such as antibodies, can be readily accomplished, for example, by protein—protein coupling agents such as SMPT. Moreover, one can desire to target growth factors, other cytokines or even bacterial endotoxin or the lipid A moiety of bacterial endotoxin to a selected cell type, in order, e.g., to achieve modulation of cytokine release. The attachment of such substances is again well within the skill in the art as exemplified by Ghose et al., *CRC Critical Reviews in Therapeutic Drug Carrier Systems* 3:262–359 (1987).

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent as described above. In the case of doxorubicin and daunomycin, attachment can be achieved by means of an acid labile acyl hydrazone or cis aconityl linkage between the drug and the antibody. Finally, in the case of methotrexate or aminopterin, attachment is achieved through a peptide spacer such as L-Leu-L-Ala-L-Leu-L-Ala (SEQ ID NO: 2), between the γ-carboxyl group of the drug and an amino acid of the antibody.

Alternatively, any such structures which are nucleic acid-encoded structures can be operatively attached to the targeting agents of the invention by standard recombinant DNA techniques, such as, for example, those discussed above.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Endothelial Localization of Receptor Tyrosine Phosphatase. ECRTP/DEP-1, in Developing and Mature Renal Vasculature Developmental assembly of the renal microvasculature is a precise process requiring spatially and temporally coordinated migration, assembly, differentiation and maturation of endothelial cells in the context of adjacent epithelial and mesangial cells. Molecular determinants of assembly are largely undefined, yet requirements for cell surface receptors to direct context appropriate endothelial responses are anticipated. Endothelial expression and distribution of the receptor tyrosine phosphatase, ECRTP/DEP-1, were evaluated during developmental assembly of the renal microvasculature. Monoclonal antibodies generated against ECRTP/DEP-1 ectodomain epitopes localize its expression to membrane surfaces of endothelial cells in glomerular, peritubular capillary and arterial renal circulations of mature human and murine kidney. During kidney development, ECRTP/DEP-1 immunostaining is evident on a subpopulation of metanephric mesenchymal cells and on putative progenitors of glomerular capillary endothelial cells early in their recruitment to developing glomeruli. ECRTP/DEP-1 is prominently displayed on luminal membrane surfaces with punctate accumulations at inter-endothelial contacts that overlap, but do not co-localize with VE cadherin. In vitro studies show that ECRTP/DEP-1 is recruited to positions of inter-endothelial contact in confluent cultured human renal and dermal microvascular endothelial cells, where its distribution overlaps, but again does not coincide with VE cadherin. Experimental dissociation of VE cadherin from endothelial junctional complexes does not redistribute ECRTP/DEP-1 away from inter-endothelial contacts. These findings indicate that ECRTP/DEP-1 ectodomains interact with proteins that are expressed on surfaces of endothelial cells and that are engaged by cell—cell contact, to convey signals for cell recognition, or arrest of migration or proliferation.

In order to identify receptor tyrosine phosphatases expressed in human renal microvascular endothelial cells (HRMEC), degenerate oligonucleotide primers derived from conserved phosphatase domains were used to amplify and sequence cDNAs representing expressed messages, according to methods described in Schoecklmann et al., *J Am Soc Nephrol* 5:730 (1994)(abstract). Among putative receptor cDNAs identified was one that was designated ECRTP (endothelial cell receptor tyrosine phosphatase), a product virtually identical to the DEP-1 (for density enhanced phosphatase) cDNA cloned by Ostman et al. from HeLa cells and regulated in abundance by cell density in WI-38 cells. Ostman et al., *Proc Natl Acad Sci USA* 91:9680–9684 (1994). ECRTP/DEP-1 (also called byp-1, HPTPh, and CD148) expression has been identified in neonatal smooth muscle cells, in breast and thryoid cancer cell lines, and in all hematopoietic lineages. Keane et al., *Cancer Research* 56:4236–4243 (1996); de la Fuente-Garcia et al., *Blood* 91:2800–2809 (1998). Although ECRTP/DEP-1 expression was identified in arterial endothelial cells of the kidney, in situ hybridization experiments failed to detect glomerular capillary localization of ECRTP/DEP-1 mRNA. Borges et al., *Circulation Research* 79:570–580 (1996). The developmental timing and distribution of its expression have not been previously reported.

Like other members of the Class III receptor tyrosine phosphatase family, including GLEPP-1, SAP-1, and DPTP 10D, ECRTP/DEP-1 is a type I membrane protein characterized by a large extracellular domain containing eight or more fibronectin type III repeats and a single cytoplasmic domain phosphatase catalytic domain. Ostman et al., *Proc Natl Acad Sci USA* 91:9680–9684 (1994). The GLEPP-1 receptor tyrosine phosphatase is structurally similar to ECRTP/DEP-1, yet shows renal expression limited to glomerular visceral epithelial cells, where it has been implicated in podocyte integrity. Thomas et al., *J Biol Chem* 269: 19953–19962 (1994). Unlike the MAM domain containing receptors, PTP μ κ and λ, available data do not support participation of class III receptors in homophilic binding, and ligands have not yet been identified.

Monoclonal antibodies were developed against ECRTP/DEP-1 ectodomain epitopes to characterize its distribution in the renal circulation of mature and developing kidney. ECRTP/DEP-1 is expressed at high levels in glomerular, peritubular and renal arterial endothelial cells and shows a pattern of distribution in vivo and in vitro that suggests it contributes to cell—cell recognition required for capillary assembly and maintenance.

Methods

Cell lines and cell culture—Primary human renal microvascular endothelial cells (HRMEC) were isolated, cultured, and used at third or fourth passage after thawing, as described. Martin et al., *In Vitro Cell Dev Biol* 33:261–269 (1997). Human dermal microvascular endothelial cells (HMEC-1 cells, CDC) were grown in MCDB131 media (Sigma Chemical Co. of St. Louis, Mo.) containing 15% fetal bovine serum (Hyclone Laboratories, Logan Utah, USA), 10 ng/ml epidermal growth factor (Collaborative Biomedical Products, Becton Dickinson, Bedford, Mass.), and 1 mg/ml hydrocortisone (Sigma Chemical Co. of St. Louis, Mo.) Ades et al., *J Invest Dermatol.* 99:683–690 (1992). Madin Darby Canine Kidney (MDCK) cells (kindly provided by L. Limbird, Vanderbilt Pharmacology) were grown in Dulbecco's minimal essential medium (DMEM, GIBCO BRL, Rockville, Md.) containing 4.5% D-glucose and supplemented with 10% fetal bovine serum. All growth medium was supplemented with 1 mM L-glutamine (GIBCO BRL, Rockville, Md.), 100 units/ml penicillin and 100 mg/ml streptomycin (GIBCO BRL, Rockville, Md.).

Generation of antibodies to recombinant ECRTP/DEP-1 proteins—Ectodomain (amino acids 175–536) and catalytic domain (amino acids 1048–1338) sequences of human, ECRTP/DEP-1 (SEQ ID NOs: 3 and 4; Ostman et al., *Proc Natl Acad Sci USA* 91:9680–9684 (1994)), were subcloned into the pRSET vector (Invitrogen, Carlsbad, Calif.). Recombinant fusion proteins were expressed in bacteria, purified by a kit sold under the registered trademark NI-AGAROSE AFFINITY™ by Invitrogen of Carlsbad, Calif., and characterized by SDS-PAGE as greater than 95% homogeneous proteins of 40 and 36 kDa, respectively. Mouse hybridoma antibodies (ECRTP-Ab1, ECRTP-Ab2) were generated against ECRTP/DEP-1 ectodomain (ECRTP/DEP-1$_{ec}$) protein by intra-peritoneal immunization, fusion with SP2-0 cells, ELISA screening, selection, expansion and purification by affinity chromatography on PROTEIN A-AGAROSE (Sigma Chemical Co. of St. Louis, Mo.).

Immunodetection of exogeneously expressed ECRTP/DEP-1—MDCK cells grown in 100 mm plastic dishes (sold under the registered trademark FALCON® by Becton, Dickinson and Company, Franklin Lakes, N.J.) were transfected with an expression plasmid pSRa DEP-1/3xHA that drives high level expression of the human ECRTP/DEP-1receptor modified by addition of three repeats of a hemagglutinin peptide (HA) to the carboxy terminus, using cationic lipid (LIPOFECTAMINE™, GIBCO BRL, Rockville, Md.) according to the manufacturer's protocol. Forty eight hours after transfection, cells were placed on ice, washed twice with ice cold PBS(–) and immediately lysed in 0.5 ml lysis buffer (50 mM HEPES pH 7.5, 50 mM NaCl, 5 mM EDTA, 2 μg/mL aprotinin, 1 μg/mL leupeptin, 1 mM PMSF). Lysates were clarified by centrifugation, and membrane receptors were recovered by batch adsorption to WGA-Agarose (Sigma Chemical Co. of St. Louis, Mo.) for 4 hours at 4° C. The resultant precipitates were resolved by 7% SDS-PAGE under reducing conditions, transferred to Immobilon-P transfer membranes (Millipore Corporation, Bedford, Mass.), and blocked in 5% non-fat dry milk in Tris-buffered saline (50 mM Tris HCl pH 7.5, 137 mM NaCl) containing 0.2% Tween 20 (TBST) overnight at 4° C. Blots were incubated with murine monoclonal ECRTPAbs 1 or 2 (10 μg/mL) or anti-HA (2.5 μg/mL) antibody followed by incubation with horseradish peroxidase-conjugated rabbit anti-mouse IgG antibody (Boehringer Mannheim, Indianapolis, Ind.). Membranes were washed with TBST, then developed using a chemiluminescent substrate (ECL, Amersham, Buckinghamshire, England) according to the manufacturer's instructions.

Generation of Stably Transfected MDCK Cells and Cell Staining—MDCK cells were transfected with an expression plasmid pCDNA3 DEP-1/3xHA (Invitrogen) using cationic lipids (Lipofectamine™, GIBCO BRL, Rockville, Md.) according to the manufacturer's protocol. Stable transfectants were selected by addition of G418 (GIBCO BRL, Rockville, Md.) to culture media at a final concentration of 800 μg/mL, and a single colony was obtained by limited dilution cloning. The cells were grown on glass coverslips (Fisher Scientific, Pittsburgh, Pa.) and fixed with 100% methanol for 10 min at –20° C. Coverslips were washed with phosphate buffered saline, blocked with 5% goat serum for 30 min at room temperature, incubated with ECRTPAb-2 (10 μg/mL) for 60 min, washed, then incubated with FITC conjugated goat anti-mouse IgG (Jackson Immunoresearch Laboratory, Westgrove, Pa.) for 60 min. Coverslips were mounted and analyzed by confocal microscopy (equipment sold under the registered trademark ZEISS® LSM410™ by Zeiss, Oberkochen, Germany). To preabsorb the immunoreactivity of ECRTP/DEP-1-Ab, 50 μg of ECRTP/DEP-1 proteins (Ec or Cy) were preincubated with ECRTPAb-2 for 4 hours at 4° C., microcentrifuged at 15,000 rpm for 20 min and the resultant supernatant was used to stain cells.

Tissue immunolocalization—Human kidney tissue was snap-frozen in a dry ice-acetone bath. Cryostat sections (4 mm) were fixed in acetone at –20° C. for 10 min, washed with phosphate buffered saline, and pre-adsorbed with avidin-biotin blocking reagents (Vector Laboratories, Inc. of Burlingame, Calif.) according to manufacturer's instructions. Sections were washed with phosphate buffered saline, blocked with 5% goat serum, incubated with monoclonal ECRTP/DEP-1 antibody (ECRTP-Ab1, 10 μg/mL, 10 min), washed, incubated with biotinylated goat anti-mouse IgG (Vector Laboratories, Inc. of Burlingame, Calif., 7.5 µg/mL, 60 min), washed, incubated with fluorescein isothiocyanate (FITC)-conjugated streptavidin (Pierce Chemical Company of Rockford, Ill., 4 µg/ml, 30 min) and finally washed with phosphate buffered saline. Coverslips were mounted (sold under the trademark Vectashield™ by Vector Laboratories, Inc. of Burlingame, Calif.) and analyzed by confocal microscopy (equipment sold under the registered trademark ZEISS® LSM410™ by Zeiss, Oberkochen, Germany). For colocalization experiments, acetone fixed frozen sections were blocked with 5% donkey serum, and incubated with mixture of ECRTP/DEP-1 antibody (10 µg/mL) and goat VE cadherin antibody (5 µg/mL, Santa Cruz Biotechnology Inc., Santa Cruz, Calif.) at room temperature for 60 minutes. Specific antibodies were detected using a mixture of FITC-conjugated donkey anti-mouse and rhodamine conjugated donkey anti-goat antibodies (Jackson Immunoresearch Laboratory, Westgrove, Pa.) at room temperature for 60 minutes. Specific immunostaining for each antigen was identified in overlapping images generated by analysis of the same section at 488 nm and 568 nm wavelengths, respectively, on a ZEISS® LSM410™ confocal microscope.

Immunolabeled murine kidney sections showed high background and required an alternative technique. The anti-ECRTP/DEP-1 mAb, ECRTP-Ab1, was directly coupled to FITC. Briefly, ECRTP-Ab1 (0.55 mL of 0.94 mg IgG/mL in 0.1 M sodium carbonate buffer, pH 9.0) was conjugated to 0.03 mL FITC solution (Sigma Chemical Co. of St. Louis, Mo., 1.0 mg/ml in DMSO) overnight at 4° C. The reaction was stopped by adding ammonium chloride to 50 mM final concentration. Following incubation for 2 hours at 4° C., the mixture was dialyzed exhaustively against phosphate buffered saline to remove unbound FITC. A mouse monoclonal IgG against rat glomerular basement membrane coupled to FITC using the identical protocol was used as a control. Hyink et al., *Am J Physiol* 270:F886–F899 (1996). Acetone fixed sections were blocked with 0.5M ammonium chloride, incubated for 30 min with MoAb-FITC conjugates, washed, and examined by epifluorescence microscopy. In some additional control experiments, the anti-DEP-FITC conjugate was mixed with a molar excess of the immunization peptide before incubation with the sections.

Immunoblots and Immunocytochemistry of Human Endothelial Cell Lines Human endothelial cells grown in 60 mm dishes were lysed at confluency in 0.5 mL of lysis buffer (20 mM TrisCl pH7.5, 50 mM NaCl, 1 mM EDTA, 0.5% Triton X-100, 0.5% SDS, 0.5% deoxycholate, 2 µg/mL aprotinin, 1 µg/mL leupeptin, 1 mM phenylmethylsulfonylfluoride) on ice for 30 minutes. Cleared lysate protein, 150 µg, was incubated with 10 µg/mL of affinity purified rabbit ECRTP/DEP-1 antibody or rabbit IgG (Sigma Chemical Co. of St. Louis, Mo.) at 4° C. for 4 hours, and immunoprecipitates were recovered using Protein-a Sepharose (Sigma Chemical Co. of St. Louis, Mo.). SDS-PAGE, and immunoblotting procedures were carried out as described above. Endothelial cells were grown on uncoated glass coverslips (Fisher Scientific, Pittsburgh, Pa.), then fixed with 50% methanol for 10 min at 4° C. Coverslips were washed with PBS, blocked with 5% goat serum for 30 min at room temperature, incubated with ECRTPAb-2 monoclonal antibody (10 µg/ml) or VE cadherin monoclonal antibody (2 µg/mL, BD Transduction Laboratory, Lexington, Ky.) for 60 min, washed, then incubated with biotinylated goat anti-mouse IgG (Vector Laboratories of Burlingame, Calif.) for 60 min, washed, and finally incubated with fluorescein conjugated (FITC) streptavidin (4 µg/ml, Pierce Chemical Company of Rockford, Ill.) for 30 min. Coverslips were mounted and analyzed by confocal microscopy (equipment sold under the registered trademark ZEISS® LSM410™ by Zeiss, Oberkochen, Germany).

Calcium Chelation to Disrupt Inter-Endothelial Cadherin Complexes—Confluent HMEC-1 cells grown on glass coverslips in DMEM media supplemented with 15% fetal bovine serum were exposed to addition of EGTA (ethylene glycol-bis(b-aminoethylether)-N,N,N',N',-tetraacetic acid, Sigma Chemical Co. of St. Louis, Mo.) to reach a final concentration of 5 mM. Cells were incubated for an additional 20 min, then fixed with 50% methanol at 4° C. for 10 min, washed with phosphate buffered saline, and stained with monoclonal ECRTP/DEP-1 antibody (10 µg/ml) or VE cadherin monoclonal antibody (2 µg/mL, BD Transduction Laboratory, Lexington, Ky.), as described above.

Figure 1A:
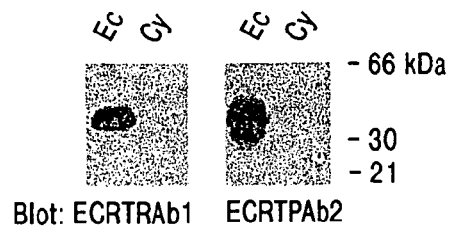
FIG. 1A depicts recognition by antibodies ECRTPAb-1 & ECRTPAb-2 of recombinant and over-expressed ECRTP/DEP-1 and is an autoradiograph depicting recombinant proteins representing extracellular (Ec) or cytoplasmic (Cy) domains of ECRTP/DEP-1 were expressed in bacteria and purified. Proteins (100 ng) were separated on a 15% SDS-polyacrylamide gels, transferred to PVDF membrane and probed with monoclonal antibodies ECRTPAb-1 or ECRTPAb-2, as indicated.
Figure 1B:
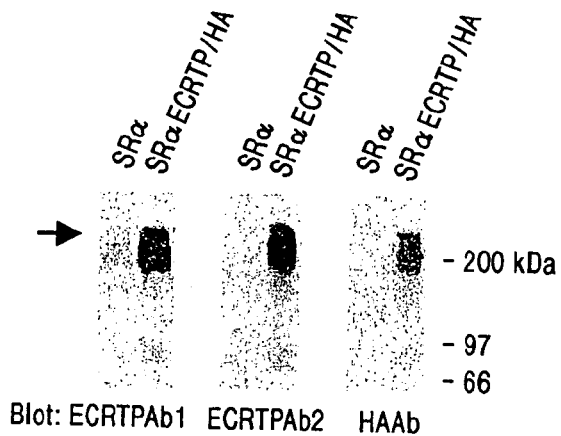
FIG. 1B depicts recognition by antibodies ECRTPAb-1 & ECRTPAb-2 of recombinant and over-expressed ECRTP/DEP-1 and is an autoradiograph depicting MDCK cells cultured in 100 mm dishes were transfected with 14 µg of empty pSRa vector (SRa) or pSRa-ECRTP/DEP-1/HA (SRa-ECRTP/HA) expression constructs and harvested at 48 hours after transfection. Membrane receptor proteins were recovered by WGA lectin-conjugated agarose from 150 µg of lysate protein. Lectin-adsorbed, eluted proteins were subjected to 7% SDS-PAGE, transferred to a PVDF membrane and probed with ECRTPAb-1, ECRTPAb-2, or anti-HA (HAAb) monoclonal antibodies, as indicated.

RESULTS—Monoclonal antibodies recognize recombinant and expressed ECRTP/DEP-1. Recombinant fusion proteins representing either ectodomain (Ec) or cytoplasmic domain (Cy) ECRTP/DEP-1 sequences were expressed in bacteria and used to immunize rabbits and/or mice. Shown in FIG. 1A, monoclonal antibodies, ECRTPAb-1 and ECRTPAb-2, specifically identify the ectodomain but not the cytoplasmic domain recombinant proteins. To ascertain whether these antibodies recognize the full length protein expressed in mammalian cells, MDCK cells were transiently transfected with either an empty expression plasmid (SRa) or one driving expression of a full length ECRTP/DEP-1 tagged on the carboxy terminus with a hemagglutinin epitope (SRa DEP-1/HA). Cell lysates from transfected cells were immunoprecipitated using the epitope-specific monoclonal anti-HA antibody, then probed with the antibodies indicated, including ECRTPAb-1 and ECRTPAb-2 (FIG. 1B). Both recognized the 220 kDa HA-tagged ECRTP/DEP-1.

Figure 1C:
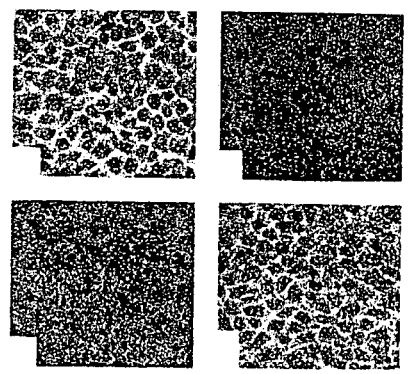
FIG. 1C is a series of photographs depicting MDCK cells stably transfected with the pSRa-ECRTP/DEP-1/HA plasmid were fixed with cold methanol and stained with ECRTPAb-2 (panels a, c & d) or a class matched control antibody (panel b). ECRTPAb-2 labeled lateral borders of cells in contact. Preincubation of ECRTPAb-2 with 50 µg of recombinant immunogen (Ec) blocked this staining (panel c), while an irrelevant recombinant protein (Cy) did not (panel d).
Figure 2A:
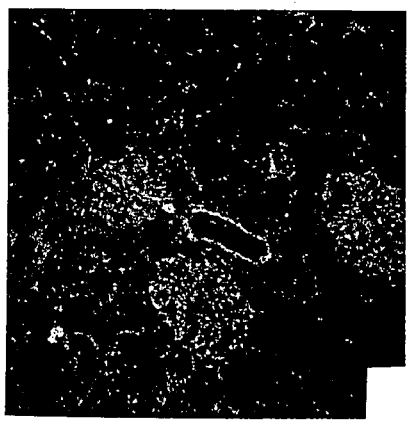
FIGS. 2A–2E are a series of photographs depicting the abundance of ECRTP/DEP-1 in endothelial cells of adult human kidney. Acetone fixed frozen sections (5 µm thickness) of human kidney were incubated with ECRTPAb-1 (panels A–D) or a class matched control monoclonal antibody (panel E) and bound antibody was detected by epifluorescence microscopy, as described in Methods. ECRTPAb-1 prominently labeled glomerular, peritubular and arterial endothelial cells. Magnifications were A) ×100; B) ×600; C) ×600; D ×400; and E) ×100.
Figure 2B:
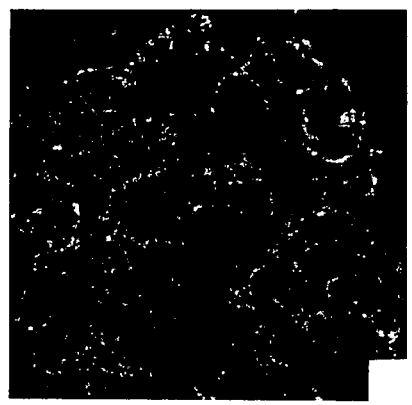
Figure 2C:
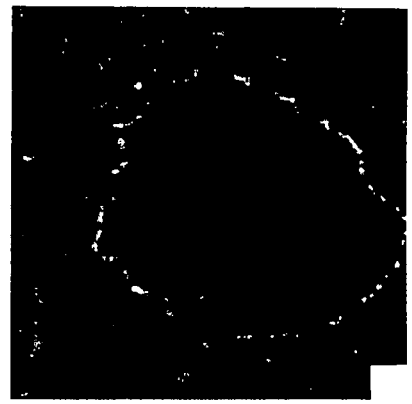
Figure 2D:
Figure 2E:
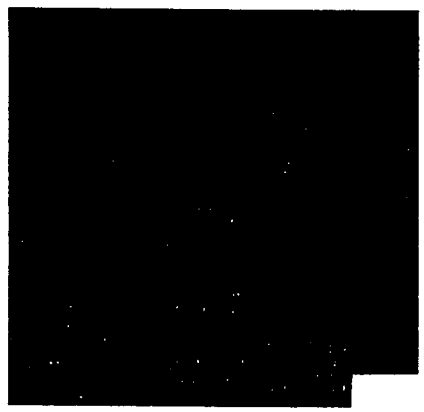

Finally, capacity of the monoclonal antibodies to specifically recognize the ECRTP/DEP-1 expressed in intact cells was assessed using MDCK cells stably transfected with ECRTP/DEP-1. Indirect epifluorescence staining with ECRTPAb-2 localized ECRTP/DEP-1 to lateral cell membranes (FIG. 1C, Panel a), a finding confirmed in confocal Z plane sections of MDCK cells grown to confluence on permeable membrane supports. Competition with the immunizing peptide (Ec) blocked immunostaining (FIG. 1C, Panel c) while the irrelevant cytoplasmic domain fusion peptide (Cy) did not (FIG. 1C, Panel d).

ECRTP/DEP-1 immunoreactivity localizes to endothelial cells of glomerular capillaries, peritubular capillaries and renal arteries. To determine the distribution of ECRTP/DEP-1 in mature mammalian kidney, indirect or direct immunofluorescence staining experiments were conducted on frozen sections from human and mouse sources. Shown in FIG. 2, ECRTP-Ab2 immunolocalizes ECRTP/DEP-1 expression to arterial, glomerular and peritubular capillaries, and in particular, to the endothelial cells in these sites. Higher magnification frames show predominant ECRTP/DEP-1 labeling along the luminal membranes of endothelial cells, at least in the arterial sites where endothelial membrane definition is most reliable (FIG. 3).

The punctate characteristic of the staining in the glomerular microcirculation led to the evaluation of whether ECRTP/DEP-1 was engaged in inter-endothelial junctional complexes. In double labeling studies using ECRTP-Ab1 and VE-cadherin antibodies, some overlap was evident (FIG. 3). In addition to the luminal endothelial membrane staining, a regional accumulation of ECRTP/DEP-1 was evident at points of inter-endothelial contact, overlapping, but not limited, to the endothelial junctional complexes that include VE cadherin. Lampugnani et al., *J Cell Biol* 129: 203–217 (1995) This pattern was evident in both arterial and peritubular capillaries. In extra-renal sites, capillary and large vessel endothelial cells of brain, lung, liver and spleen was identified and endocardial staining were also apparent.

Figure 4A:
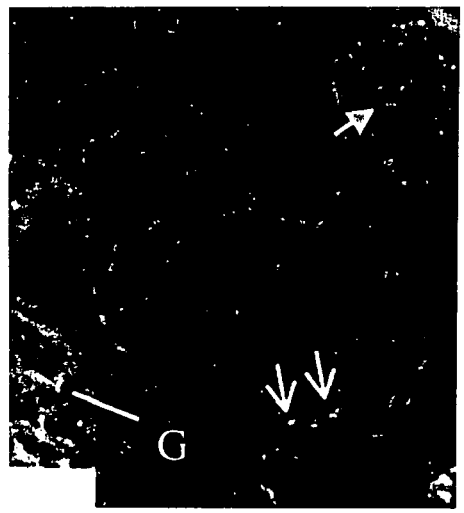
FIG. 4 is a series of photographs depicting ECRTP/DEP-1 expression in developing murine glomeruli. Cryostat kidney sections of embryonic day 14 (A), day 16 (B), postnatal day 6 (C) and adult mice (D) were immunolabeled with ECRTPAb-1 as described in the Methods of Example 1. In panels A & B; ECRTPAb-1 binds to cells dispersed in the mesenchymal area (arrow), to endothelial precursor cells (arrowhead) migrating to the vascular cleft of comma-shaped glomeruli and to endothelium of capillary stage glomeruli (G). In panels C & D, ECRTPAb-1 preferentially labels endothelial cells of the glomerulus (G), artery (A) and peritubular capillaries (arrow) in mature kidney. (Original magnification; A) ×400; B) ×200; C) ×200; and D) ×350.
Figure 4B:

Based on the prominent ECRTP/DEP-1 expression in vascular endothelium of mature kidney, temporal and spatial expression of this receptor during renal vascular development in mouse embryos was evaluated. Shown in FIG. 4, ECRTPAb-1 binds as an antigen, its murine ECRTP/DEP-1, based on its similar pattern of staining is mature murine and human kidneys, and based on the effect of the recombinant human immunogen (Ec) to block staining of the mouse tissue. In developing mouse kidneys at E14, E16, and postnatal day 6, (FIGS. 4A–C) conjugates of ECRTP-Ab1-FITC displayed a pattern of immunoreactivity that was strikingly similar to the pattern observed previously using antibodies against the VEGF receptor, flk-1, and the EphB1/ephrin-B1 receptor-ligand. Daniel et al., *Kidney Int* 50:S-73–S-81 (1996). Notably, ECRTP-Ab1-FITC bound to endothelial cells of developing glomeruli and microvessels in the fetal kidney cortex. Small but intense foci of bound antibody were observed on isolated cortical mesenchymal cells believed to be angioblasts (FIGS. 4A & 4B). Within vascular clefts of comma- and S-shaped developing glomeruli, a subpopulation of cells consistent with glomerular endothelial precursors were labeled (FIGS. 4A & 4B).

Figure 3A:
FIG. 3 depicts confocal localization of ECRTP/DEP-1 and VE cadherin in human kidney vasculature. Acetone fixed kidney sections were simultaneously labeled with ECRTPAb-1 and a polyclonal goat antibody against VE cadherin. Bound antibodies were detected using fluorescein conjungated anti-mouse (panels A, B, E, F) or rhodamine-conjugated anti-goat (panels C, D, E, F) Ig antibodies. ECRTPAb-1 (green) staining distributed over the entire endothelial membrane in large artery and glomerular capillaries (A, B) while VE cadherin labeling (red) is restricted to endothelial junctions (C, D). Overlapping confocal images demonstrated colocalization of ECRTP with VE cadherin at inter-endothelial junctions. (magnification×600).
Figure 3B:
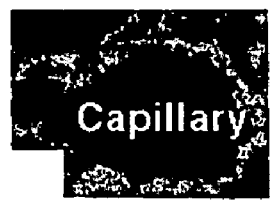
Figure 3C:
Figure 3D:
Figure 3E:
Figure 3F:
Figure 4C:
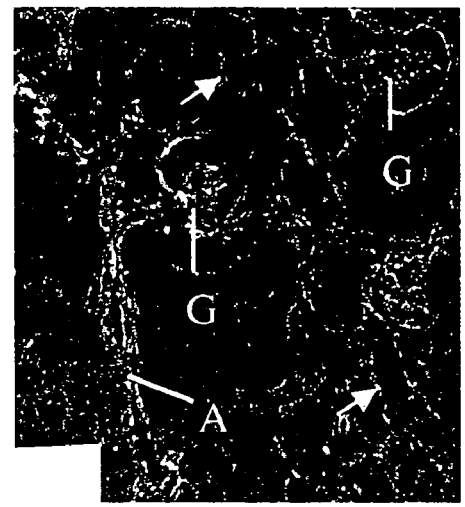
Figure 4D:
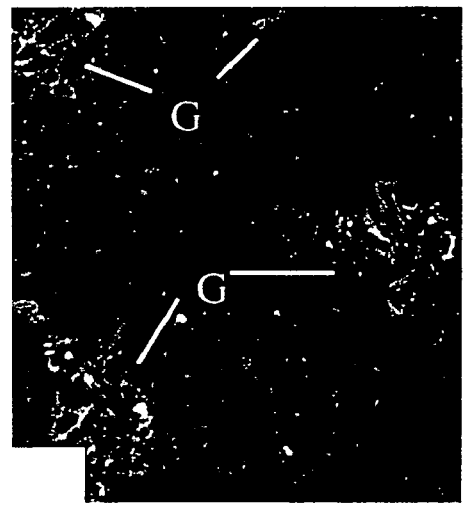

Immunolabeling for ECRTP/DEP-1 on sections of neonatal kidney produced a distinct vascular labeling pattern (FIG. 4C). Arteriolar, glomerular, and peritubular capillary endothelia all labeled intensely (FIG. 3C). Glomerular endothelial cells were also brightly labeled in adult mouse kidney (FIG. 4D), as they were in sections of human kidney. Other cells within the immature and mature kidneys did not bind ECRTP-Ab1-FITC, and sections labeled with control monoclonal IgG-FITC conjugates, or mixtures of ECRTP-Ab1-FITC and the immunization peptide (Ec) showed no staining.

Independent immunoblot and immunofluorescence staining experiments using ECRTP-Ab1 showed high level expression in endothelial cells cultured from a range of different vascular sites, including the HRMEC from which it was cloned, a dermal microvascular endothelial cell line, HMEC-1 (Ades et al., *J Invest Dermatol* 99:683–690 (1992); human umbilical vein endothelial cells; and a HUVEC derived cell line, Eahy926 (Bauer et al., *J Cell Physiol* 153:437–449 (1992). Epitopes recognized by this antibody were not detected in non-endothelial cell lines; including HEK293 cells, glomerular mesangial cells, vascular smooth muscle cells, and P19 embryonic carcinoma cells.

Figure 5A:
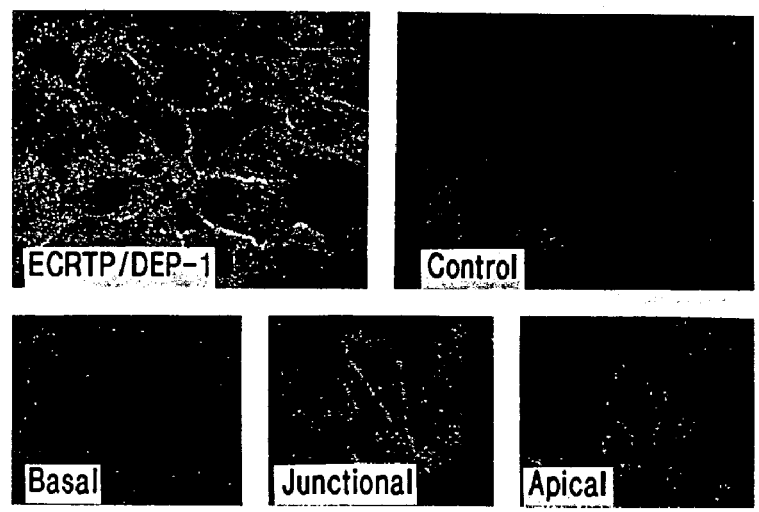
FIG. 5A depicts distribution of ECRTP/DEP-1 of inter-endothelial contacts in cultured human endothelial cells, but ECRTP/DEP-1 does not dissociate from junctions with VE cadherin and is a series of photographs depicting Methanol fixed HRMEC cells were labeled with ECRTPAb-2 as described in Methods of Example 1. ECRTP/DEP-1 is distributed between points of inter-endothelial membrane contact and punctate regions of the apical membrane in serial confocal images.
Figure 5B:
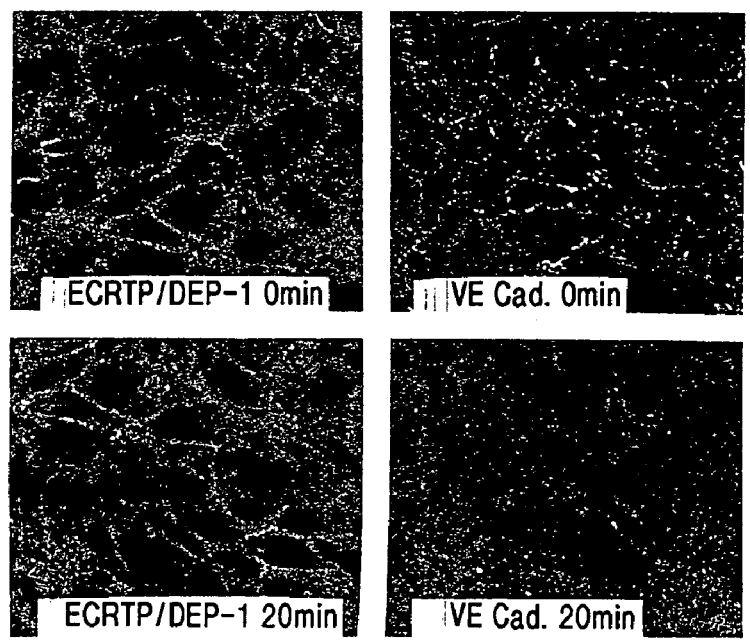
FIG. 5B depicts distribution of ECRTP/DEP-1 of inter-endothelial contacts in cultured human endothelial cells, but ECRTP/DEP-1 does not dissociate from junctions with VE cadherin and is a series of photographs depicting HMEC-1 cells were grown to confluency, then incubated with media containing 5 mM EGTA for 0 min (panels a & c) or 20 min (panels b & d), prior to fixation. The distribution of ECRTPAb-2 and VE cadherin labeling was examined as described in Methods of Example 1 at each time. While the distribution of ECRTP/DEP-1 immunoreactivity was not altered in the low $Ca^{2+}$ medium, junctional VE cadherin staining dissipated, consistent with dissociation of VE cadherin junctions and redistribution across the cell membrane.

Shown in FIG. 5 are patterns of ECRTP/DEP-1 localization in human renal microvascular endothelial cells, HRMEC (Panel A), and human dermal microvascular endothelial cells, HMEC (Panel B). Confluent HRMEC cultures displayed prominent staining with ECRTP-Ab2 at points of inter-endothelial contact. In addition, there were punctate accumulations of apical membrane staining in confocal planes capturing the apical surface (Panel A), but not on the basal membrane surface. Endothelial cells plated at sufficiently low density to be isolated from contact with one another did not show the prominent pattern of cell border staining seen in contacting cells. It should be noted that ECRTP-Ab1 did not demonstrate the inter-endothelial localization seen with ECRPT-Ab2, but stained only the subpopulation of receptors evident on the apical surface.

This apparent accumulation of ECRTP/DEP-1 at sites of endothelial cell—cell contact is consistent with the punctate accumulations of staining seen in intact mature vessels, and suggests that a subpopulation of receptors distribute to points of inter-endothelial contact. Thus, the distribution of ECRTP/DEP-1 was compared with that of VE cadherin. Confocal localization of ECRTP/DEP-1 and VE cadherin immunoreactivity in double labeling experiments of confluent HMEC cultures again showed modest overlap of ECRTP/DEP-1 staining with the VE-cadherin localized in inter-endothelial junctions. Similar patterns of colocalization were seen in double labeled sections of human kidney tissue (FIG. 3). Finally, experiments were conducted to ascertain whether the intercellular accumulation of ECRTP/DEP-1 immunoreactivity required the integrity of VE-cadherin interactions. Shown in FIG. 5B, EGTA treatment of the HMEC-1 cells dissociates VE cadherin from the inter-endothelial junctional complexes, but has no apparent effect on ECRTP/DEP-1 localization over the 20–30 minute time period of the experiment. This result suggests that any inter-endothelial junctions that can retain ECRTP/DEP-1 do not require cadherin integrity. Furthermore, these data are consistent with the observations that ECRTP/DEP-1 and VE cadherin overlap, but do not co-localize precisely in intact vessel endothelium (FIG. 3).

DISCUSSION—Several of the observations presented here provide new insights about the ECRTP/DEP-1 tyrosine phosphatase in vascular development and in endothelial cell—cell interactions. The significance of the initial identification of ECRTP/DEP-1 as a transcript expressed in cultured human renal microvascular endothelial cells has been confirmed at several levels. Schoecklmann et al., *J Am Soc Nephrol* 5:730 (1994)(abstract). Cultured HRMEC's express the protein on cell membranes, just as glomerular and peritubular capillaries do in intact kidney tissue. Indeed, capillary and arterial endothelium appear to be the dominant cellular sources of ECRTP/DEP-1 expression in mature human and mouse kidney. In contrast with the previous in situ experiments in rat kidney kidneys, described in Borges et al., *Circulation Research* 79:570–580 (1996), high level expression were found in glomeruli of both mouse and human.

Careful evaluation of the sites of membrane to which ECRTP/DEP-1 distributes has shown prominent apical membrane staining in arterial endothelium in addition to the inter-endothelial membrane staining that appears responsible for the somewhat granular staining pattern in the glomerular capillaries. The lateral cell membrane distribution of ECRTP/DEP-1 in the artificial MDCK epithelial cell system and in contacting cultured HRMEC (FIG. 5), led to the formally evaluation of the relationship of lateral ECRTP/DEP-1 membrane accumulation with VE cadherin complex integrity. The in situ overlap of ECRTP/DEP-1 and VE cadherin immunostaining is modest (FIG. 3), and is restricted to very focal regions of inter-endothelial contact in some, but not all junctional complexes. As ECRTP/DEP-1 lateral membrane distribution is maintained in cultured endothelial cells in which VE cadherin complexes have been dissociated by calcium chelation, it is concluded that there is neither anatomical co-localization nor functional correlation of ECRTP/DEP-1 distribution with maintenance of inter-endothelial complexes. These findings, however, cannot exclude the possibility that lateral ECRTP/DEP-1 membrane distribution can function to establish conditions permissive to assembly of inter-endothelial complexes containing VE cadherin.

Alternatively, the lateral membrane distribution can reflect interaction of the ECRTP/DEP-1 extracellular domain with a putative ligand expressed on contacting membranes that is capable of redistributing receptors or stabilizing them in ligand-receptor complexes created through juxtacrine engagement. Certainly there is available evidence that membrane associated receptor tyrosine phosphatase activity is increased in cultured cells, including endothelial cells, that are in close contact. Pallen and Tong, *Proc Natl Acad Sci USA* 88:6996–7000 (1991); Batt et al., *J Biol Chem* 273:3408–3414 (1998). In the culture systems presented in this Example, an increase in ECRTP/DEP-1 activity that correlates with cell density and with cell-density mediated growth arrest has been demonstrated.

The apical membrane distribution of ECRTP/DEP-1 in arterial and apparently in capillary endothelium is intriguing, particularly in the context of data showing that platelets and all hematopoietic lineages express the ECRTP/DEP-1. Palou et al., *Immunol Lett* 57:101–103 (1997). Homophilic interactions between ECRTP/DEP-1s of endothelial cells and circulating cells that can encounter them on luminal membranes of intact vessels suggest that it is likely that regulatory factors, or co-receptors on each of the engaging cells are important in modulating any downstream responses.

Finally, the data assessing the developmental pattern of ECRTP/DEP-1 expression on cells that contribute to assembly of the glomerular capillary network offers insight about roles for this receptor in this coordinated process. Receptor tyrosine phosphatases of the ECRTP/DEP-1 subclass, including DPTP10D, have been assigned important roles in the targeting of neurons to correct destinations during development. Desai et al., *Cell* 84:599–609 (1996). Previous reports have identified expression in hematopoietic progenitors, including erythroid, lymphoid and myeloid series lineages. Palou et al., *Immunol Lett.* 57:101–103 (1997). With the accumulating evidence that hemangioblasts serve as common precursors of both hematopoietic and vascular endothelial lineages, it now appears that ECRTP/DEP-1 expression is initiated early in the ontogeny of these precursors. Furthermore, it appears that ECRTP/DEP-1 can function to promote differentiation of erythroid lineage cells that express it. Kumet et al., *J Biol. Chem.* 271:30916–30921 (1996).

Example 2

ECRTP/DEP-1 Mediates Signals for Endothelial Growth Arrest and Migration Inhibition Powerful endogenous inhibitors of angiogenesis, such as thrombospondin, angiostatin and endostatin, inhibit the proliferation and migration of cultured endothelial cells in vitro. Such angiogenesis inhibitory controls appear to signal arrest of endothelial growth and migration by engaging endothelial surface receptors. One of the most powerful growth inhibitory signals for cultured endothelial cells is imposed by cell—cell contact, which is described in the art as "density mediated growth arrest" or "contact mediated growth arrest". High level expression of the receptor tyrosine phosphatase, ECRTP/DEP-1, at inter-endothelial contacts in microvascular and large vessel endothelium of human kidney and other organs is described in Example 1.

In this Example, the ECRTP/DEP-1 has been determined to mediate endothelial growth and migration arrest signals. The ECRTP/DEP-1 is catalytically activated in conjunction with cell—cell contact. Transient overexpression of full length ECRTP/DEP-1 arrests endothelial growth and migration. Bivalent forms of a monoclonal antibody, ECRTPAb-1, that binds the ECRTP/DEP-1 ectodomain inhibits endothelial proliferation and migration, while Fab fragments are inactive. This antibody imposes inhibition on corneal angiogenic responses in a mouse system. These findings indicate that the ECRTP/DEP-1 signals endothelial growth and migration arrest upon engagement of its ligand on the surfaces of contacting endothelial cells, and that surrogate activators, or modulators, of endothelial growth arrest signals are viable candidates for angiogenesis inhibitors.

Methods

Cell Culture—Primary human renal microvascular endothelial cells, HRMEC, were isolated, cultured, and used at third or fourth passage after thawing, as described in Martin et al., *In Vitro Cell Dev Biol* 33:261–269 (1997). Human dermal microvascular endothelial cells (HMEC-1 cells, CDC) were grown in MCDB131 media (Sigma Chemical Co. of St. Louis, Mo.) containing 15% fetal bovine serum (Hyclone Laboratories, Logan Utah, USA), 10 ng/mL epidermal growth factor (Collaborative Biomedical Products; Becton Dickinson, Bedford, Mass.), and 1 µg/mL hydrocortisone (Sigma Chemical Co. of St. Louis, Mo.). Ades et al., *J Invest Dermatol* 99:683–690 (1992). All growth media were supplemented with 1 mM L-glutamine (GIBCO BRL, Rockville, Md.), 100 units/mL penicillin and 100 µg/mL streptomycin (GIBCO BRL, Rockville, Md.).

Antibodies—Ectodomain (ECRTP/DEP-$1_{ec}$, amino acids 175–536) and catalytic domain (ECRTP/DEP-$1_{cy}$, amino acids 1048–1338) sequences of human ECRTP/DEP-1 (SEQ ID NOs: 3 and 4; Ostman et al., *Proc Nat/Acad Sci USA* 91:9680–9684 (1994) were subcloned into the pRSET vector (Invitrogen, Carlsbad, Calif.). Recombinant fusion proteins were expressed in bacteria, purified by Ni-agarose affinity (Invitrogen, Carlsbad, Calif.), and characterized by SDS-PAGE as greater than 95% homogeneous proteins of 40 and 36 kDa, respectively. Rabbit antiserum to the ECRTP/DEP-$1_{cy}$ protein was generated by repetitive immunization, and was affinity purified, as described in Koenig et al., *J Clin Immunol* 13:204–211 (1993). Mouse hybridoma antibody ECRTPAb-1 was obtained following immunization with ECRTP/DEP-$1_{ec}$ protein by intraperitoneal immunization, fusion with SP2-0 cells, ELISA screening, selection, expansion and purification by affinity chromatography on protein A-agarose (Sigma Chemical Co. of St. Louis, Mo.).

Assays for ECRTP/DEP-1 Abundance and Tyrosine Phosphatase Activity—Cells plated at the densities and harvested at the times indicated in the Figure Descriptions were washed repeatedly with iced phosphate buffered saline before in situ addition of 2 ml of buffer containing 50 mM Hepes (pH 7.5), 50 mM NaCl, 5 mM EDTA, 1 mM PMSF, 1 mM β-mercaptoethanol, 1% Triton X-100. Detergent solubilized cells were incubated for 15 min at 4° C. and insoluble material was removed by repeated microcentrifugation (two times) at 13,000×g, 10 min, 4° C. Proteins in solubilized fractions were quantitated using a modified BCA assay (Pierce Chemical Company of Rockford, Ill.). In some experiments, batch adsorption and elution from *triticum vulgaris* lectin (WGA) conjugated to agarose (Sigma Chemical Co. of St. Louis, Mo.) was conducted as described in Stein et al., *J Biol Chem* 271:23588–23593 (1996). Final elution for fractions subjected to phosphatase assays was in buffer containing 25 mM imidazole (pH 7.2), 0.1 mg/ml bovine albumin, 10 mM dithiothreitol (phosphatase assay buffer), plus 3 mM N,N',N" triacetylchitotriose (Sigma Chemical Co. of St. Louis, Mo.).

$^{32}$P-labeled, phosphorylated substrate (Raytide) was prepared by the manufacturer's recommendations as described (Oncogene Sciences of Uniondale, N.Y.) to achieve specific activities of (dpm/fmol). Phosphatase activity in lectin purified fractions was assayed in triplicate at 30° C. for times indicated in the Figure Descriptions in 200 µl volumes of phosphatase buffer using 300 ng/ml substrate in the presence or absence of Na$_3$VO$_4$, as described. Released phosphate was quantitated by scintillation counting and data are expressed as mean cpm+/−SEM. Assays were linear over 1–10 min periods.

Figure 8A:
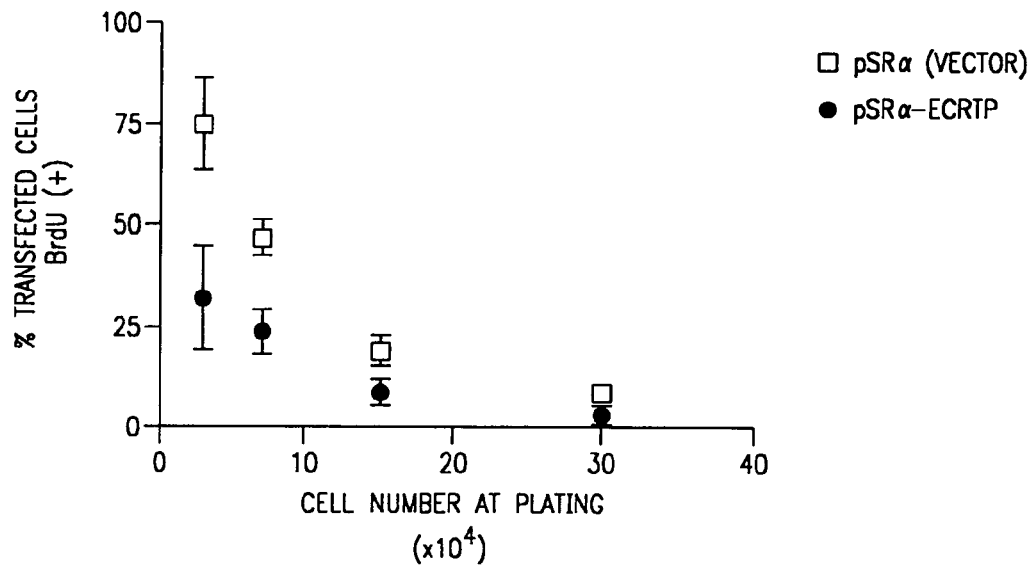
FIG. 8A shows that ECRTP/DEP-1 overexpression, or bivalent antibody against ECRTP/DEP-1, ECRTPAb-1, imposes proliferation arrest on HRMEC and is a graph showing transient transfection of HMREC with ECRTP/DEP-1 cDNA imposes a growth inhibition at low cell densities. Approximately 3×10$^5$ HRMEC were cotransfected with 1.7 µg pSRa (vector control) or HA epitope tagged (hemagglutinin) pSRα-ECRTP/DEP-1 (pSRα-ECRTP), as indicated, and 0.4 µg pEGFP (Clontech) to permit scoring of BrdU labeling of transfected cells, as described in Methods of Example 2. At 24 hours, transfected cells were replated on p35 dishes in the numbers indicated. Thirty six hours later, S phase cells were labeled for 30 min with BrdU, as described in Methods of Example 2, and +GFP positive cells were scored for BrdU incorporation. Data represent means+/−SEM for quadruplicate determinations.

For determination of ECRTP/DEP-1 activity and abundance (FIG. 8) HRMEC cells were plated at cell densities indicated in the Figure Descriptions. At 36 hours after plating, a subset of cells, as indicated, was treated for 10 min with pervanadate (1 mM H$_2$O$_2$+1 mM Na$_3$VO$_4$), then cells were lysed in buffer containing 50 mM HEPES/pH7.5, 150 mM NaCl, 5 mM EDTA, 1% Triton X-100, 0.1 mM, 5 µg/ml aprotinin, 1 µg/ml leupeptin, 1 mM PMSF, clarified by centrifugation and equivalent lysate proteins(150 µg) were immunoprecipitated by incubation with affinity-purified monospecific ECRTP/DEP-1 rabbit antibody (12.5 µg/mL) overnight at 4° C., and collected on protein A-sepharose (Sigma Chemical Co. of St. Louis, Mo.).

The washed immunocomplexes were assayed for PTP activity with p-nitrophenylphosphate, pNPP (Sigma Chemical Co. of St. Louis, Mo.) as previously described in Wang, Y. and Pallen, C. J., *J Biol Chem* 267:16696–16702 (1992). Briefly, the immunocomplexes were incubated with reaction mixture (50 mM sodium acetate/pH5.5, 0.5 mg/mL bovine albumin, 0.5 mM DTT, 5 mM pNPP) at 30° C. for 30 min in the absence or presence of 1 mM Na$_3$VO$_4$. Reactions were stopped by addition of 2N NaOH, and the absorbance at 410 nm was measured.

For quantification of ECRTP/DEP-1 abundance, immunoprecipitated fractions were also resolved by 7% SDS-PAGE under reducing conditions, transferred to PVDF membranes (sold under the trademark Immobilon-P™ by Millipore Corporation, Bedford, Mass.), and blocked in 5% non-fat dry milk in Tris-buffered saline (50 mM Tris/HCl pH7.5, 137 mM NaCl) containing 0.2% Tween 20 (TBST) overnight at 4° C. Blots were incubated with ECRTPAb1 (10 µg/mL) or phosphotyrosine monoclonal antibody, 4G10, (1.0 µg/mL, Upstate Biotechnology) and bound antibodies detected with horseradish peroxidase-conjugated rabbit anti-mouse IgG antibody (Boehringer) and a chemiluminescent reagent (ECL; Amersham, Buckinghamshire, England).

Proliferation Assays—In initial assays of HRMEC proliferation (FIG. 6), cells were plated at the indicated density, harvested at the indicated times and counted in quintriplicate. Data represent means±SEM. In other experiments (FIGS. 8 and 9), HMEC-1, cells were grown on a 35 mm diameter dish (sold under the registered trademark FALCON® by Becton, Dickinson and Company, Franklin Lakes, N.J.) and cotransfected with ECRTP/DEP-1 expression plasmids (either parent vector, pSRα, or pSRα-ECRTP/DEP-1/3xHA, driving high level expression of a carboxy-terminal hemagglutinin (HA) epitope tagged human ECRTP/DEP-1, 1.8 µg) and a green fluorescent protein expression plasmid (pEGFP, Clontech, 0.4 µg). An adenovirus-assisted lipofectamine procedure that transfects 40–50% of HMEC-1 cells under these conditions was used, as is also described in Example 1. Transfected cells were harvested 48 h after transfection and replated on glass coverslips in individual wells of a 12 well plate at densities indicated in the Figure Descriptions (range 2–10×10$^4$), to achieve attached cell confluencies of 20–90+%). Proliferating cells were labeled by addition of 10 µM 5-Bromo-2'-deoxyuridine (BrdU) to culture media for 30 min at 70 hours after transfection. BrdU incorporation was immunocytochemically detected using a monoclonal BrdU antibody and rhodamine-conjugated anti-mouse IgG, according to manufacturer's protocol (Boehringer Mannheim, Indianapolis, Ind.). The cells of at least five independent fields were observed under epifluorescence microscopy (Nikon ECLIPSE® E600™) and the frequency of BrdU labeling in GFP positive cells was scored.

Planar Endothelial Migration Assay—A planar endothelial migration assay was developed to assess the rate of endothelial closure of circular "wounds" of 300–500µ diameter. A rotating silicon-tipped bit attached to a drill press was used to generate 3–5 "wounds" in confluent endothelial monolayers within individual wells of multi-well plates. At the time of "wounding", medium in individual wells were supplemented with agents at concentrations indicated in the Figure Descriptions. Residual areas of individual wounds in photomicroscopic images captured at the indicated times (4 & 8 hours) were quantitated using a Bioquant (Nashville, Tenn.) software package calibrated to a Nikon DIAPHOT™ microscope. Expressed in this manner, the rates of wound closure are remarkably linear, with linear regression r$^2$ values≧0.985. Each data point displayed here represent the mean±SEM of three or more individual determinations from the same well. Each experiment described is representative of findings from three or more independent observations.

In situ Transfection Assay for Migration—Confluent HMEC-1 cells grown on 6 well culture plate were transfected with 2.2 µg of expression plasmids, pSRα ECRTP/DEP-1/3xHA, or pSRα-EphB1/3xHA (Stein et al., *Genes Dev* 12:667–678 (1998)) and circular wounds were prepared at 48 hours after transfection as described above. When the wounds were almost closed (12 h after wounding), monolayers were fixed with 2% paraformaldehyde for 20 min, washed with phosphate buffered saline, permeabilized with 0.02% saponin for 60 min, blocked with 5% goat serum and incubated with 5 µg/mL of monoclonal HA antibody, 12CA5, (Berkeley Antibody Company (BAbCo), Richmond, Calif.) for 60 min. Coverslips were then washed with phosphate buffered saline, incubated with biotinylated goat anti-mouse IgG (Vector Laboratories, Inc. of Burlingame, Calif., 7.5 µg/mL) for 60 min, washed, incubated with HRP conjugated avidin-biotin complexes (Vector Laboratories, Inc. of Burlingame, Calif.) for 30 min and finally developed using 6 mg/mL of 3, 3'-diaminobenzidine (Sigma Chemical Co. of St. Louis, Mo.).

Cornea Pocket Angiogenesis Assay—Agents to be tested for angiogenic or anti-angiogenic activity were immobilized in a slow release form in an inert hydron pellet of approximately 0.2 µl volume, as described in Kenyon, Voest, et al. (1996). That pellet is implanted into the corneal epithelium of an anesthetized C57BL mice in a pocket created by micro-dissection. Over a 5 to 7 day period angiogenic factors stimulate the ingrowth of vessels from the adjacent vascularized corneal limbus. A photographic record is generated using slit lamp photography. The appearance, density and extent of these vessels are evaluated and scored. In some cases the time course of the progression is followed in anesthetized animals, prior to sacrifice. Vessels are evaluated for length, density and the radial surface of the limbus from which they emanate (expressed as clock-face hours).

Figure 6A:
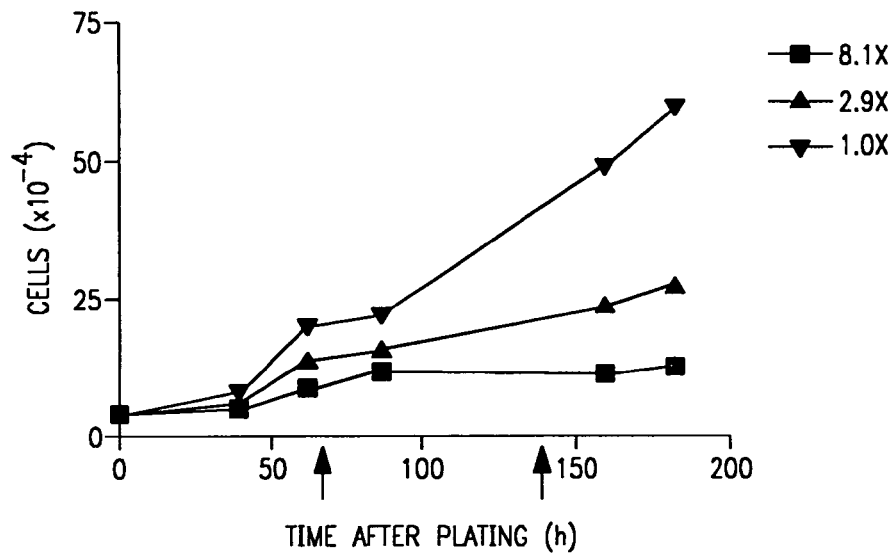
FIG. 6A shows that endothelial cell density imposes growth arrest and increases lectin recoverable tyrosine phosphatase activity and is a line graph showing identical numbers of human renal microvascular endothelial cells (HRMEC) were plated in growth medium on 100 (1×), 60 (2.9×) or 35 (8.1×) mm diameter plastic dishes, effecting the indicated fold differences in cell density at the time of plating. Medium was replaced with growth medium at points indicated by arrows. Cells were counted in a Coulter counter and means of quadruplicate samples are displayed. Proliferation was arrested in cells at 8.1× density after a single cell doubling, and after approximately 3 doublings in cells plated at 2.9×density.
Figure 6B:
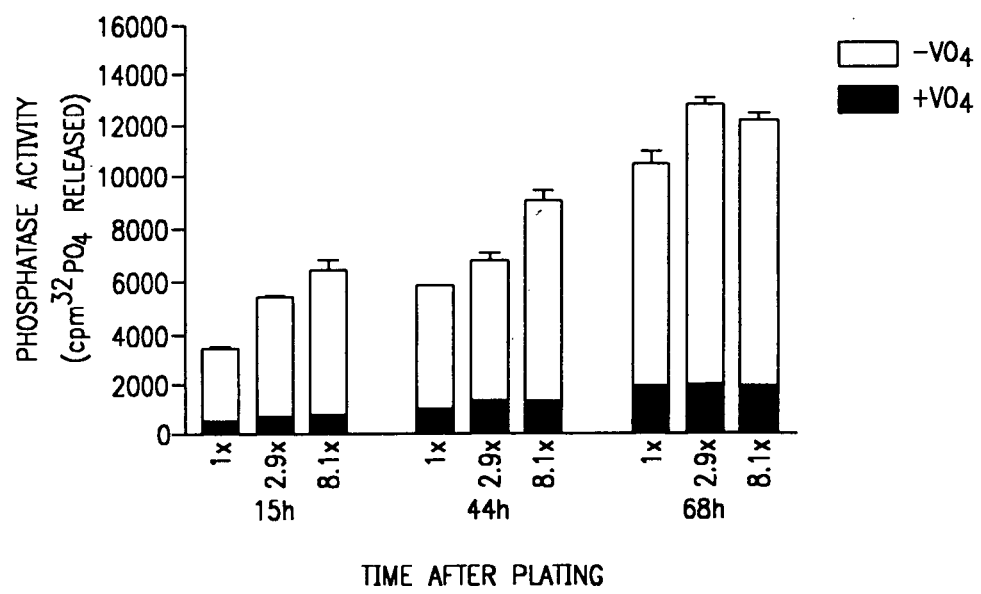
FIG. 6B shows that endothelial cell density imposes growth arrest and increases lectin recoverable tyrosine phosphatase activity and is a bar graph showing cells plated for the indicated times at the indicated densities were lysed, and receptor tyrosine phosphatase activity, including that attributable to ECRTP/DEP-1, was recovered by lectin affinity chromatography and assayed as described in Methods of Example 2 in the absence or presence of the tyrosine phosphatase inhibitor, sodium orthovanadate (VO$_4$, 100 µM).

Results—Initial experiments were conducted to establish the cell density (cell number/surface area) at which human renal microvascular endothelial cells (HRMEC) display growth arrest in serum supplemented growth medium. In situ experiments have shown high level expression of ECRTP/DEP-1 in glomerular and extraglomerular microvascular endothelial cells of human kidney, as well as in arteries and a wide range of other tissues. In FIG. 6A, identical numbers of HRMEC were plated on cell culture plates of 9.6, 28.3, or 78.5 cm$^2$, representing 1, 2.9, or 8.1 fold the surface area of a 35 mm diameter dish, as indicated. Growth medium was replaced every 3 days. Depending upon passage number, HRMEC reached growth arrest at a density of approximately 1.3–6×10$^4$ cells/cm$^2$, a response that supercedes responses to maximal growth stimuli. Doubling time under density unrestricted conditions is approximately 44 hours. The established human dermal microvascular endothelial cell line, HMEC-1, similarly displayed density-mediated growth arrest properties.

Increasing fibroblast cell density was previously associated with increases in tyrosine phosphatase activity recovered from membrane-associated fractions. See e.g., Pallen, C. J. and Tong, P. H. *Proc Natl Acad Sci USA* 88:6996–7000 (1991). Among membrane-associated proteins, can surface receptors, including ECRTP/DEP-1, are modified by N-linked glycosylation of the ectodomain region and can be recovered using lectin affinity chromatography. Honda et al., *Blood* 84:4186–4194 (1994). Shown in FIG. 6B, tyrosine phosphatase activity of the *triticum vulgaris* (wheat germ agglutinin, WGA) lectin fraction recovered from identical numbers of HRMEC plated was analyzed for the indicated times at densities determined by the culture dish surface area. As early as 15 hours after plating, marked differences in vanadate-sensitive tyrosine phosphatase activity were evident. Lectin-recovered receptor-associated tyrosine phosphatase activity was 2 fold higher in cells plated at a density sufficient to impose growth arrest (8.1×), compared with those plated at lower density (1×). As cells plated at lower densities (2.9 and 1×) proliferated, increases in activity were seen, eliminating the marked difference. The increased lectin-recovered activity was evident at times anticipating the imposition of proliferation arrest, suggesting that either the prevalence of specific tyrosine phosphatases was increasing, that the activity of pre-existing phosphatases was increased, or that tyrosine phosphatases were being recruited to associate with lectin recovered proteins. The previous report that DEP-1 receptor prevalence increased with increasing cell density lead us to evaluate the activity and distribution of DEP-1. Ostman et al., *Proc Natl Acad Sci USA* 91:9680–9684 (1994).

Figure 7:
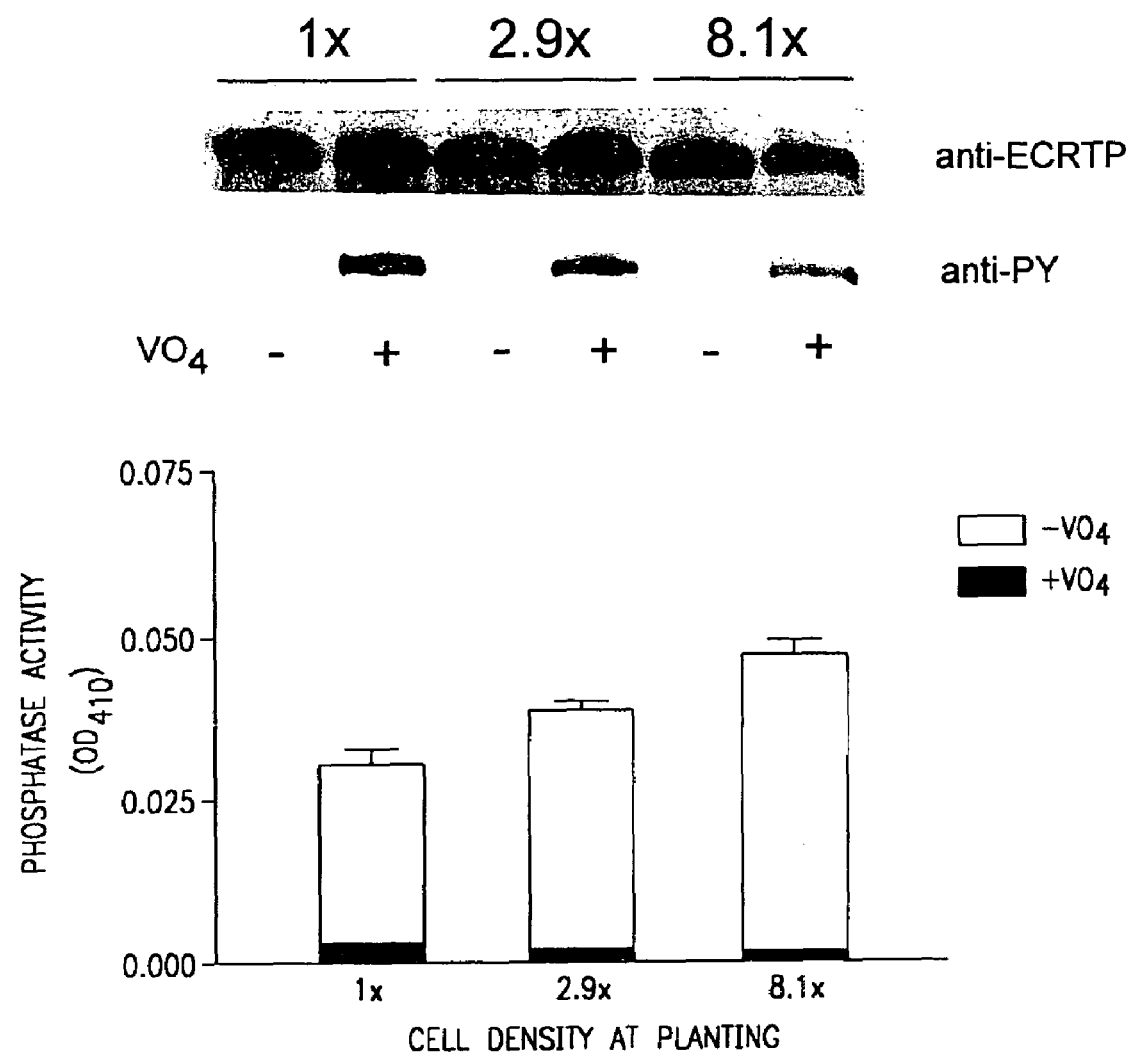
FIG. 7 is an autoradibgraph and a bar graph showing that increased cell density imposes increases in activity, but not amount, of immunoprecipitated ECRTP/DEP-1. Identical numbers of HRMEC were plated as in FIG. 6 at the indicated cell densities. Monospecific affinity purified rabbit polyclonal antibodies were used to immunoprecipitate ECRTP/DEP-1 from cells treated for 10 min immediately before harvest with 1 mM peroxyvanadate (+VO$_4$) or vehicle (−VO$_4$) at 36 hours after plating, as described in Methods of Example 2. Recovered ECRTP/DEP-1 antigen was quantitated by immunoblot with the monospecific antibody and its endogenous phosphotyrosine content assessed by phosphotyrosine immunoblot using the 4G10 monoclonal antibody. Phosphatase activity in immunoprecipitated samples was assayed using pNPP as substrate in the absence (−VO$_4$) or presence (VO$_4$) of sodium orthovanadate, as described. Data are displayed as optical density of the product in triplicate samples+/−SEM.

Shown in FIG. 7, differences in the amount of immunoprecipitated ECRTP/DEP-1 antigen could not be detected when cells plated for 33 hours at different densities were compared. Additional experiments failed to show a change in the ratio of Triton X-100 soluble to insoluble fractions at these densities. However, 1.8 fold increases in the vanadate-sensitive ECRTP/DEP-1 associated tyrosine phosphatase activity were recovered by immunoprecipitation from cells plated at the highest (8.1×) compared with the lowest (1×) cell density. Shown in the lower panel immunoblot (FIG. 7), immunoprecipitated ECRTP/DEP-1 is itself a tyrosine phosphoprotein in cells pretreated with vanadate. Moreover, the level of intrinsic phosphotyrosine is decreased in the immunoprecipitated ECRTP/DEP-1 recovered from cells plated at high density, correlating with the increased tyrosine phosphatase activity in that fraction. These findings indicate that the abundance of ECRTP/DEP-1 does not change acutely in endothelial cells plated at high density, but that the ECRTP/DEP-1-associated phosphatase activity does increase. Efforts to demonstrate by in gel zymographic phosphatase assays that the increased activity is intrinsic to ECRTP/DEP-1 have not been successful.

To further pursue the possibility that ECRTP/DEP-1 mediates signals capable of arresting endothelial proliferation and migration, HMEC-1 cells were cotransfected with an expression plasmid driving high level expression of an epitope-tagged ECRTP/DEP-1, and with a plasmid driving expression of green fluorescent protein to mark transfected cells. Using adenovirus-assisted transfection method, transfection of 40–50% of HMEC-1 cells that display survival, migration and proliferation properties similar to nontransfected cells was routinely accomplished. Shown in FIG. 8A, high level expression of a full length ECRTP/DEP-1 imposes marked suppression of BrdU incorporation across a range of plating densities of transfected cells when compared with the empty expression vector.

ECRTP/DEP-1 overexpression imposed similar effects upon endothelial migration as those observed with proliferation. Shown in FIG. 9A, HMEC-1 cells transfected with plasmids driving expression of hemagglutinin epitope (HA) tagged versions of either ECRTP/DEP-1/HA or a receptor tyrosine kinase, EphB1/HA, were plated at densities to permit them to rapidly attain a confluent monolayer. A circular "wound" of approximately 500 µm diameter was generated, and migration of transfected and non-transfected cells to close the "wound" was determined after 33 hours, by staining for the expressed protein HA epitope. Unlike cells transfected with the EphB1/HA control, ECRTP/DEP-1/HA expressing cells did not migrate to contribute to the wound closure. While forced overexpression of ECRTP/DEP-1 can be informative about the potential for this receptor to affect proliferation or migration, this approach is much less discriminatory than use of high affinity reagents interacting with endogenously expressed ECRTP/DEP-1s. To this end, a panel of monoclonal antibodies generated against ECRTP/DEP-1 ectodomain sequences was screened for activity.

Figure 8B:
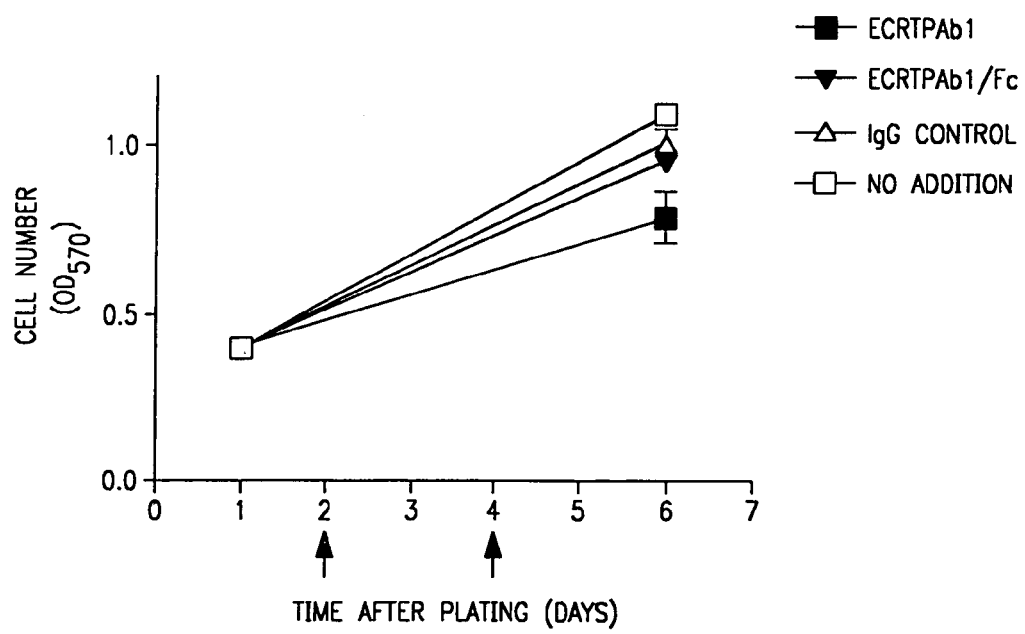
FIG. 8B shows that ECRTP/DEP-1 overexpression, or bivalent antibody against ECRTP/DEP-1, ECRTPAb-1, imposes proliferation arrest on HRMEC and is a line graph showing that ECRTPAb-1 inhibits endothelial proliferation and migration. HRMEC (3×10$^4$) were plated in p35 dishes at time 0. Growth medium was replaced at 24 h, cells were counted, and either IgG control (10 µg/ml) or ECRTPAb1 (10 µg/ml) antibodies were added. Replicate samples (5) of cells were counted on day 4, and are expressed as means+/−SEM.

Shown in FIG. 8B, bivalent forms of the monoclonal, ECRTPAb1, imposed a marked inhibitory effect on proliferation of HRMEC plated at low density, in spite of repeated growth medium exchanges. Equivalent concentrations of a class matched monoclonal control antibody were inactive. Because oligomerization is a critical determinant of activation of many receptor tyrosine kinases and phosphatases (Weiss, A. and Schlessinger, J., *Cell* 94:277–280 (1998)), ECRTPAb1 Fab fragments were prepared to test whether bivalency of the interacting monoclonal was required for activity. Also shown in FIGS. 8B and 8C, equimolar concentrations of the ECRTPAb1 Fab fragments were inactive as growth inhibitors in endothelial cells plated at subconfluent densities in serum-containing growth medium.

Figure 8C:
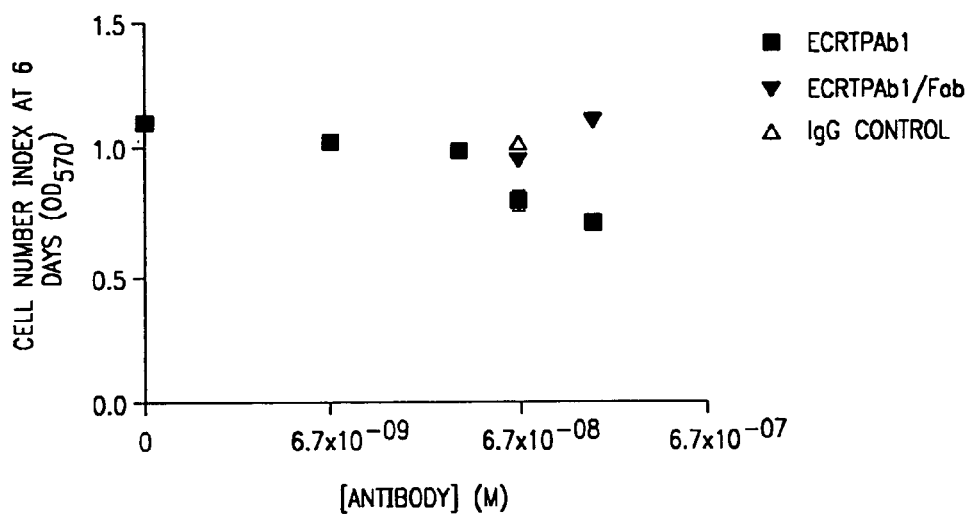
FIG. 8C is a data point plot depicting that equal numbers of HRMEC were plated at time 0, and antibodies or Fab fragments added at the concentrations indicated. Replicate plates were harvested on day 1, to confirm homogeneous plating efficiency in each condition, and on day 6 to assess cell proliferation, respectively. Data points represent mean values of five replicates±SEM.
Figure 9B:
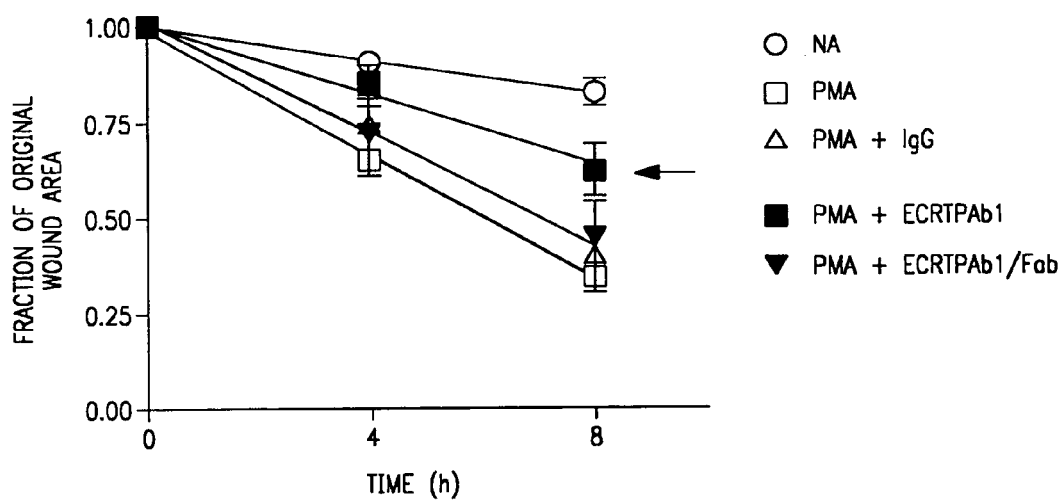
FIG. 9B depicts inhibition of endothelial migration by ECRTPAb-1 and is a line graph reflecting analysis of 300 to 420 µm diameter "wounds" which were created in HRMEC confluent monolayers at time 0, as medium was exchanged to serum-free medium supplemented by either no addition (NA), or phorbol myristate acetate (20 ng/ml) in the presence of the indicated antibodies or fragments, including a class matched IgG control (IgG, 10 µg/ml), ECRTPAb1 (10 µg/ml), or Fab fragments of ECRTPAb1 (3 µg/ml, molar equivalency). Triplicate wounds were used to generate microscopic images at the indicated times, and the residual "wound" area calculated and expressed as a fraction of the original wound, by an automated capture sequence using Bioquant Image Analysis Software. Each data point represents the mean±SEM of three determinations.
Figure 9A:
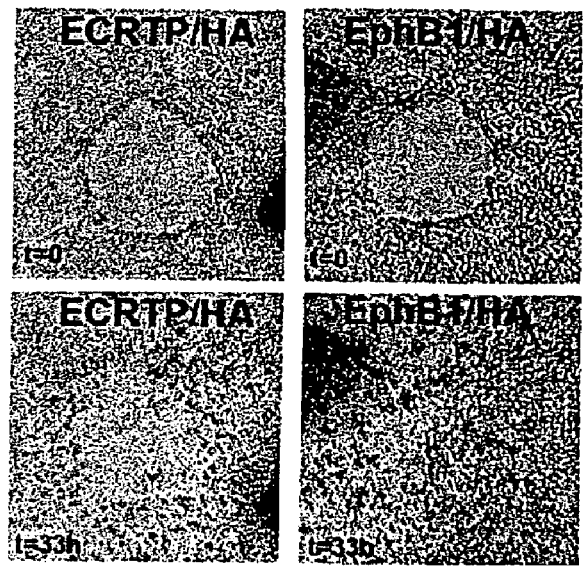
FIG. 9A depicts inhibition of endothelial migration by ECRTPAb-1 and is a series of photographs depicting monolayers of HRMEC were transiently transfected with plasmid pSRαECRTP/DEP-1/HA, or pSRαEphB1/HA, as indicated. Forty eight hours later, "wounds" were created in the confluent monolayers and permitted to close over the ensuing 30 h. Monolayers were then stained with the monoclonal hemagglutinin antibody, 12CA5, to detect the positions of cells transiently expressing high levels of ECRTP/DEP-1/HA or EphB1/HA, respectively. Only rare ECRTP/DEP-1 overexpressing cells migrated to close the "wound".
Figure 9C:
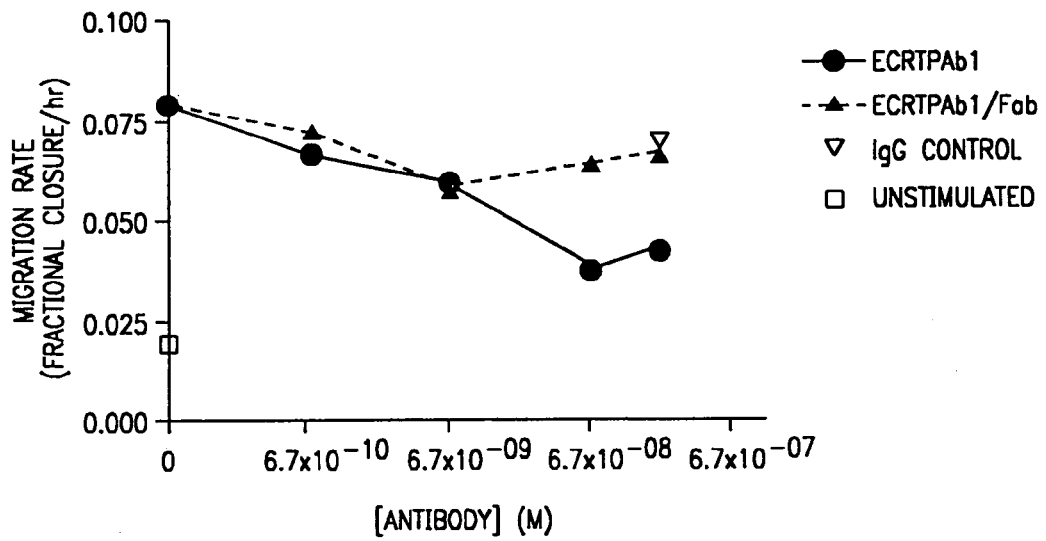
FIG. 9C depicts inhibition of endothelial migration by ECRTPAb-1 and is a line graph analyzing data produced by the same assay procedure as FIG. 9B. Using the same assay procedure, migration rates were calculated by linear regression of mean values determined in cells exposed to IgG control, ECRTPAb1, or ECRTPAb1/Fab, using three independent time points. r$^2$ values≧0.90 for each data point plotted. The open square (□) indicates the migration rate for closure of unstimulated cells.

Additional endothelial "wound" closure assays, similar in design to those presented in FIG. 9A, were conducted to evaluate effects of bivalent and monovalent ECRTPAb1 on endothelial migration. Displayed in FIG. 9B are the residual fractions of original wound areas remaining at the times indicated. Phorbol myrisate acetate (PMA) markedly accelerated the rate of migration and wound closure, compared with unstimulated cells in serum-free medium. Bivalent ECRTPAb1 displayed marked activity to inhibit the PMA stimulated migration, while equimolar concentrations of monovalent Fab fragments, and a control monoclonal were inactive. The linear characteristics of time dependent "wound" closure in this assay permitted us to determine relative migration rates for the population, expressed in FIG. 9C as fractional closure/hr. Effective concentrations of bivalent ECRTPAb1 (67 and 200 nM) were similar to those active as inhibitors of proliferation (FIG. 8C).

Figure 10:
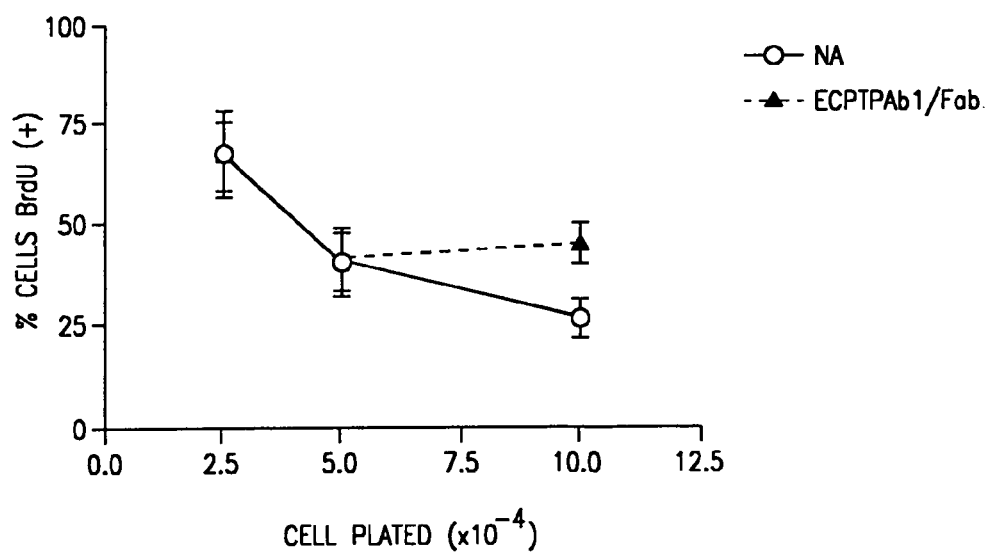
FIG. 10 is line graph depicting that ECRPTAb1 Fab fragments attenuate endothelial density mediated growth arrest. HMEC-1 cells of the indicated numbers were plated in on coverslips in 12 well dishes at time 0 in growth media supplemented by no addition (NA) or ECRTPAb1 (67 nM). Twenty four hours later BrdU staining was assayed as described in Methods of Example 2 and the percentage of BrdU positive cells scored by counting of five independent fields for each condition (greater than 400 cells/point). Data represent means±SEM.

In aggregate, these findings suggested that engagement of endogenous ECRTP/DEP-1s by bivalent antibodies can function like a "surrogate ligand" to emulate responses normally evoked by an endogenous membrane-associated ligand upon cell—cell contact. Since the ECRTPAb1 Fab fragments were inactive as "surrogate ligands" to inhibit migration and proliferation in subconfluent cells, it was asked whether they can have activity as antagonists of endogenous ligand engagement of ECRTP/DEP-1 in cells plated at high density. It was reasoned that Fab fragments can interrupt endogenous ligand-receptor engagement and subsequent growth arrest signals in cells plated at high density. Shown in FIG. 10, ECRTPAb-1 Fab had a marked effect to release cells from the density-imposed inhibition of BrdU uptake that marks S phase entry.

Figure 11:
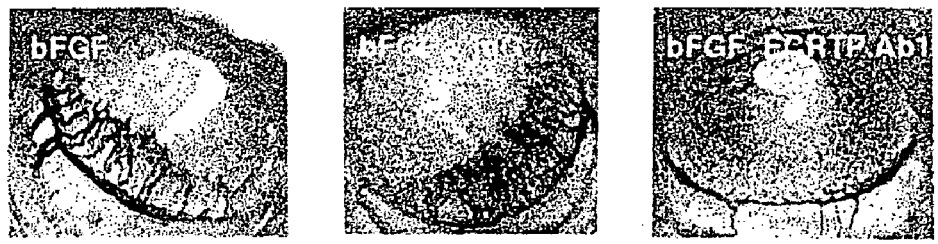
FIG. 11 is a series of photographs depicting that ECRTPAb1 inhibits corneal pocket angiogenesis responses to bFGF. Hydron pellets were impregnated with the angiogenesis stimulant, basic FGF (90 ng), alone, or supplemented with a class matched control monoclonal antibody (IgG, 200 ng) or ECRTPAb1 (200 ng), and placed in a pocket created in the corneal epithelium of anesthetized mice. Five days after implantation, angiogenic responses were scored, and photographed. Representative examples show inclusion of the ECRTPAb1 inhibits the zone of proliferation around the implanted pellet.

As a final test to determine whether ECRTPAb-1 functions to induce an angiostatic signal, it was tested whether this antibody modified angiogenic responses to basic FGF in the mouse corneal pocket assay. Shown in FIG. 11, inclusion of ECRTPAb-1, but not a control IgG, in the implanted slow release hydron pellet inhibited angiogenesis, scored by reducing the length of capillary sprouts as they approached the source of the angiogenic stimulus. This attenuation of capillary length, without effect on radial distribution of new vessels, suggests that pro-angiogenic basic FGF can diffuse more rapidly from the slow release pellet than ECRTPAb-1, permitting brisk initiation of angiogenesis with subsequent attenuation.

Example 3

Method of Screening for Endogenous Ligand of ECRTP/DEP-1

Labeled ECRTP/DEP-1 is used to perform binding studies to identify cells with ECRTP/DEP-1 ligands using Scatchard analysis; and to perform cross-linking studies which demonstrate the ECRTP/DEP-1 ligand(s) on polyacrylamide gels. These initial characterization methods are used to identify cells with high and low numbers of ECRTP/DEP-1 ligand(s) for purification and isolation studies. Once a cell line with high levels of ECRTP/DEP-1 ligand has been identified, then the protein is purified by the following approaches:

Approach A: Biochemical Purification

A cell line which expresses high levels of ECRTP/DEP-1 ligand is lysed and the protein from lysates or membrane preparations is purified by gel filtration followed by purification of the ligand with a column containing the ECRTP/DEP-1 bound to a solid phase such as sepharose. The purified ligand protein can then be microsequenced and the gene cloned using degenerate oligonucleotides derived form the protein sequence.

Approach B: cDNA Library Purification

The ECRTP/DEP-1 is radiolabeled with $^{125}$I and then used to screen cell lines or tissues by Scratchard analysis for specific binding of ligand. Once such ligand binding is identified, a cDNA library is constructed from that tissue or cell line and transfected into a cell line that does not exhibit specific binding. These transfected cells are then screened for newly acquired specific binding which indicates they have been transfected with a construct containing the gene for the ECRTP/DEP-1 ligand. Plasmid DNA from positive clones is then isolated and sequenced for identification. A single construct is then transfected back into the null cells to verify that binding between ligand and receptor is mediated by the transfected gene. Kluzen et al. *Proc Natl Acad Sci USA* 89:4618–4622 (1992).

Alternatively, chimeric ECRTP/DEP-1 and immunoglobulin Fc molecules are constructed. LaRochelle et al., *J Cell Biol* 129:357–366 (1995). The chimeric molecules can then be used to screen for binding to ECRTP/DEP-1 ligand on whole cells via flow cytometry. Alternatively, due to the presence of the immunoglobulin component of the molecule, cell lysates are screened by immunoblotting or by immunoprecipitation of metabolically labeled cells. This technique can identify ECRTP/DEP-1 binding proteins by a variety of different methods. Peptide digests of the identified proteins are then generated so that peptides can be sequenced and the whole molecule cloned by the degenerative oligonucleotide approach.

Thus, this Example pertains to a method for isolating a ligand for an ECRTP/DEP-1, and to a purified and isolated ligand for an ECRTP/DEP-1. The method comprises contacting cells or cell lysates having the ligand or suspected of having the ligand with ECRTP/DEP-1; and isolating the ligand which binds with ECRTP/DEP-1. The cells having the ligand are identified by labeling the ECRTP/DEP-1; screening cell cultures with the labeled ECRTP/DEP-1; and isolating cells that bind an elevated amount of the labeled ECRTP/DEP-1.

The ligand is isolated by lysing the cells and passing the cell lysate over a column containing the ECRTP/DEP-1 bound to a solid phase matrix within the column. Alternatively, the ligand is isolated by constructing a cDNA library from the cells binding the ligand; transfecting the cDNA library into a cell line that does not exhibit binding of the ligand; screening the cell line for newly acquired specific binding; isolating DNA form cells exhibiting specific binding; and sequencing the isolated DNA to determine the DNA sequence for the ligand.

The ECRTP/DEP-1 is optionally labeled by binding the ECRTP/DEP-1 to an immunoglobulin. In this case, the ligand is isolated by immunoprecipitation of the ECRTP/DEP-1-ligand-immunoglobulin complex. Alternatively, the ligand of the ECRTP/DEP-1 is isolated using flow cytometry.

Example 4

Identification of Binding Epitope for ECRTPAb-1

Figure 12:
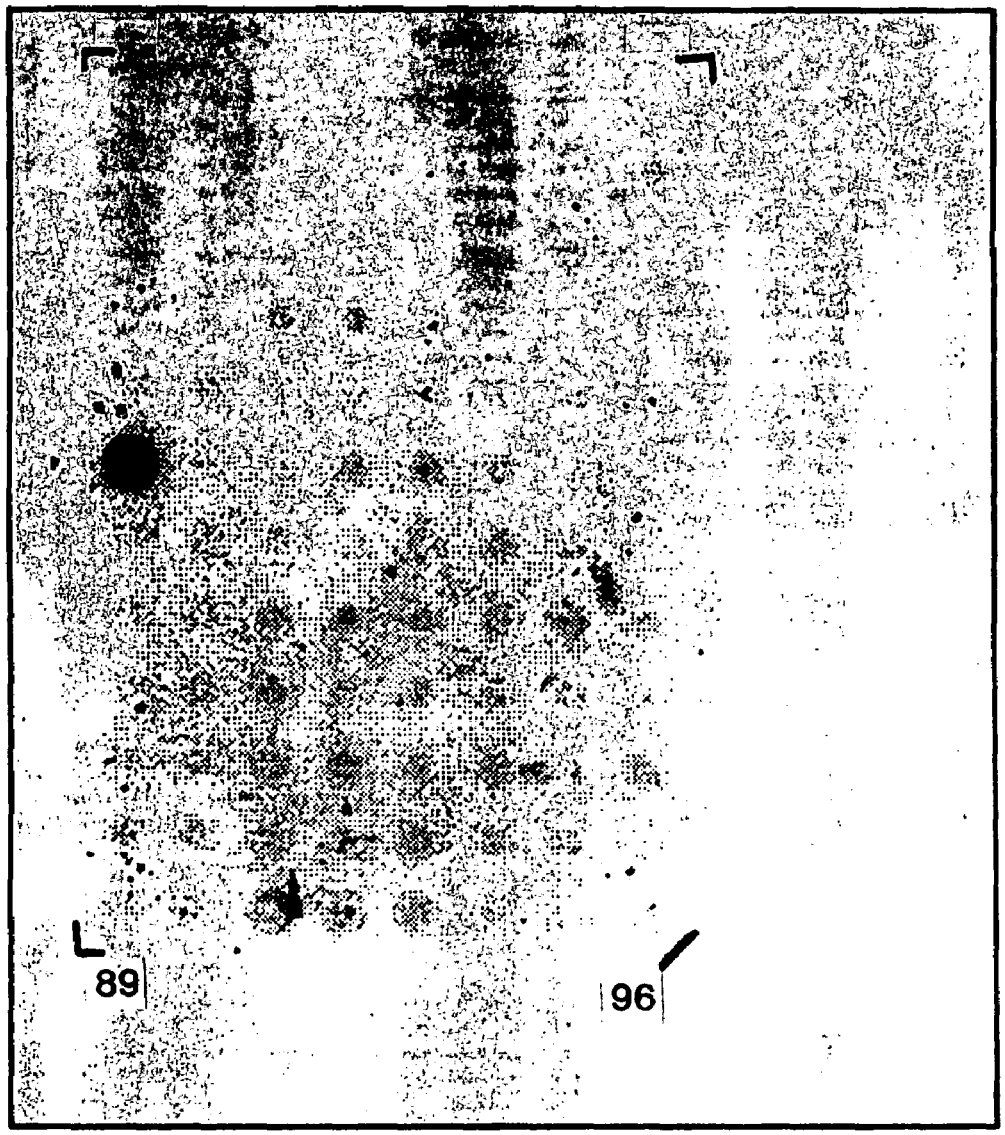
FIG. 12 is an autoradiograph showing that ECRTPAb-1 binds peptide sequence QSRDTEVL (SEQ ID NO: 1) of ECRTP/DEP-1 ectodomain.

A series of 96 eight to nine amino acid peptides was generated. The eight to nine amino acid peptides span in overlapping epitopes the 351 amino acid sequence against which ECRTPAb-1 was derived was generated. These peptides were generated and immobilized in a defined array on the surface of a membrane that was probed with ECRTPAb-1. Binding of ECRTPAb-1 to peptide #41 in the array was identified using a peroxidase-conjugated anti-mouse IgG second antibody, by chemiluminescence autoradiography (FIG. 12). The sequence of this peptide derived from the array is n-QSRDTEVL-c (SEQ ID NO:1). The 8-amino acid epitope represents the target sequence within the ECRTP ectodomain against which functional ECRTP agonists and antagonists interact, based on biological activities of ECRTPAb-1. Antibodies, including humanized antibodies, and other peptides with high affinity for this defined amino acid sequence have biological activities comparable to those demonstrated herein using ECRTPAb-1.

Example 5

Assay for Scoring Biological Activity of Antibodies, Proteins and Peptides that Bind ECRTP In an effort to develop a simplified reconstitution assay system capable of scoring biological activities mediated through ECRTP, Chinese Hamster Ovary (CHO) cells that do not express endogenous ECRTP were transfected with a plasmid construct driving high level expression of ECRTP (pSRα-ECRTP/HA), or catalytically inactive mutated forms (pSRa-ECRTP/HA/C—S, pSRα-ECRTP/HAΔcy), in these cells. Transiently transfected CHO cells were then dispersed and plated on 24 well plates and exposed to either control IgG, or ECRTPAb-1, or monovalent forms of ECRTP (ECRTPAb-1-Fab). Proliferation of cells transfected with wild type ECRTP, but not with either mutant form, was inhibited (approximately 40%) by incubation with ECRTPAb-1, but not with either control IgG, or ECRTPAb-1-Fab.

In parallel, ECRTP was immunoprecipitated from CHO cells transfected with these plasmids and expressing equivalent amounts of ECRTP or mutant forms (shown in the inserts above FIGS. 13A and 13B) following a time course of exposure (0–30 min) to either ECRTPAb-1 or ECRTPAb-1-Fab. Shown in the immunoblot panels on the right in FIGS. 13A and 13B, Ab1 evoked a rapid de-phosphorylation of tyrosine residues on the wild type (WT) ECRTP, but had no effect on catalytically inactive C/S mutant forms. These findings provide primary evidence that the catalytic phosphatase function is critical to the action of ECRTPAb-1 to inhibit proliferation and to provoke de-phosphorylation of ECRTP.

Finally, co-expression of either catalytically inactive C/S or Cy deleted forms of ECRTP with the functional ECRTP form abrogates inhibitory effects of the ECRTPAb-1 on CHO proliferation (FIG. 13B). This proliferation assay thus evaluates whether putative counter-receptors (ligands) are competent to function through ECRTP to inhibit cell growth. In each case, the monovalent and bivalent forms of ECRTPAb-1 provide a reagent that can be used in the assay to define functional counter-receptors.

Example 6

Transgenic Animal Having Catalytically Inactive ECRTP/DEP-1

A transgenic mouse expressing a catalytically inactive form of ECRTP/DEP-1 was prepared. The mouse was prepared using a "knockout" approach with respect to the ECRTP/DEP-1 gene. Embryonic death was observed in homozygous "knockout" animals. Heterozygous animals displayed significant vascularization malformations. Thus, the transgenic mouse further established the role of ECRTP/DEP-1 in cell growth, cell survival and angiogenesis.

REFERENCES

The references listed below as well as all references cited in the specification are incorporated herein by reference to the extent that they supplement, explain, provide a background for or teach methodology, techniques and/or compositions employed herein.

Ades et al., *J Invest Dermatol* 99:683–690 (1992).
Augenlicht and Baserga, *Exp Cell Res* 89:255–262 (1974).
Ausprunk et al., *Am J Pathol*, 79:597–618 (1975).
Batt et al., *J Biol Chem* 273:3408–3414 (1998).
Bauer et al., *J Cell Physiol* 153:437–449 (1992).
Beekhuizen, H. and van Furth, R. *J Vascular Res* 31:230–239 (1994).
Billard, C., et al., *Blood* (2000 Feb. 1) 95(3):965–72.
Bittner et al., *Methods in Enzymol* 153:516–544 (1987).
Bodanszky, et al., "Peptide Synthesis", John Wiley & Sons, Second Edition, (1976).
Borges et al., *Circulation Research* 79:570–580 (1996).
Cheresh et al., *J Biol Chem*, 262:17703–17711 (1987).
Choime et al., *J Biol Chem* 270:21144–21150 (1995).
Coomber, B. L. *J Cell Biochem* 52:289–296 (1993).
Daniel et al., *Kidney Int* 50:S-73–S-81 (1996).
de la Fuente-Garcia et al., *Blood* 91:2800–2809 (1998).
Desai et al., *Cell* 84:599–609 (1996).
Dillman et al., *Antibody Immunocon Radiopharm* 1:65–77 (1988).
Dulbecco et al., *Virol* 8:396 (1959).
Eijgenraam, F., *Science* 261:883–884 (1993).
Engerman et al., *Laboratory Investigation* 17:738–744 (1967).
EP 44167
Fields et al., *Int. J. Peptide Protein Res* 35:161–214 (1990).
Flickinger & Trost, *Eu. J. Cancer* 12(2):159–60 (1976).
Ghose et al., *CRC Critical Reviews in Therapeutic Drug Carrier Systems* 3:262–359 (1987).
Ghose et al., *Meth. Enzymology* 93:280–333 (1983).
Gumkowski et al., *Blood Vessels* 24:11–23 (1987).
Hailing et al., *Nucl Acids Res* 13:8019–8033 (1985).
Honda et al., *Blood* 84:4186–4194 (1994).
Huse et al., *Science* 246:1275–1281 (1989).
Hyink et al., *Am J Physiol* 270:F886–F899 (1996).
Inouye et al., *Nucleic Acids Res* 13:3101–3109 (1985).
Keane et al., *Cancer Research* 56:4236–4243 (1996).
Kimura et al., *Immunogenetics* 11:373–381 (1980).
Kitamoto et al., *J Clin Invest* 99:2351–2357 (1997).
Kluzen et al. *Proc Natl Acad Sci USA* 89:4618–4622 (1992).
Knowles & Thorpe, *Anal. Biochem* 120:440–443 (1987).
Koenig et al., *J Clin Immunol* 13:204–211 (1993).
Kohler and Milstein, *Nature* 256:495–497 (1975).
Kumet et al., *J Biol Chem* 271:30916–30921 (1996).
Lamb et al., *Eur Jrnl Biochem* 148:265–270 (1985).
Lampugnani et al., *J Cell Biol* 129:203–217 (1995).
LaRochelle et al., *J Cell Biol* 129:357–366 (1995).
Leveen et al., *Genes Dev* 8:1875–1887 (1994).
Logan et al., *Proc Natl Acad Sci USA* 81:3655–3659 (1984).
Lord et al., In *Genetically Engineered Toxins* (Ed. A. Frank, M. Dekker Publ., p. 183) (1992)
Lowy et al., *Cell* 22:817 (1980).
Martin et al., *In Vitro Cell Dev Biol* 33:261–269 (1997).
McOmie, J. F. W., "Protective Groups in Organic Chemistry", Plenum Press, New York, (1973).
Meienhofer, J., "Hormonal Proteins and Peptides", Vol. 2, p. 46, Academic Press (New York) (1983).
Merrifield, *Adv Enzymol*, 32:221–96 (1969).
More et al., *J Patho* 172:287–292 (1994).
Mulligan et al., *Proc Natl Acad Sci USA* 78:2072 (1981).
O'Hare et al., *FEBS Lett* 210:731 (1987).
Ogata et al., *J Biol Chem* 256:20678–20685 (1990).
Ossonski et al., *Cancer Res* 40:2300–2309 (1980)
Ostman et al., *Proc Natl Acad Sci USA* 91:9680–9684 (1994).
Pallen, C. J. and Tong, P. H. *Proc Natl Acad Sci USA* 88:6996–7000 (1991).
Palou et al., *Immunol Lett* 57:101–103 (1997).
Pietersz et al., *Antibody, Immunoconj Radiopharm* 1:79–103 (1988).

Pluckthun, in *The Pharmacology of Monoclonal Antibodies*, vol. 113,
Rosenburg and Moore eds., Springer-Verlag, New York, pp. 269–315 (1994). *Remington's Pharmaceutical Sciences*, 16th Ed. Mack Publishing Company, (1980)
Rijksen et al., *J Cell Physiol* 154:393–401 (1993).
Robert et al., *Am J Physiol* 271:F744–F753 (1996).
Robert et al., *Am J Physiol* 275:F164–F172 (1998).
Ruther et al., *EMBO J.* 2:1791 (1983).
Sastry, et al., *Proc Natl Acad Sci USA* 86:5728–5732 (1989).
Schoecklmann et al., *J Am Soc Nephrol* 5:730 (1994) (abstract).
Scholz et al., *Cell Tissue Res* 290:623–631 (1997).
Schroder et al., "The Peptides", Vol. 1, Academic Press (New York) (1965).
Smith et al., *J Virol* 46:584 (1983).
Soriano, P., *Genes Dev* 8:1888–1896 (1994).
Stein et al., *J Biol Chem* 271:23588–23593 (1996)
Stein et al., *Genes Dev* 12:667–678 (1998).
Steward et al., "Solid Phase Peptide Synthesis", W. H. Freeman Co., San Francisco, (1969).
Szybalska et al., *Proc Natl Acad Sci USA* 48:2026 (1962).
Takahashi et al., *Kidney Int* 53:826–835 (1998).
Thomas et al., *J Biol Chem* 269:19953–19962 (1994).
Thorpe et al., *Cancer Res* 47:5924–5931 (1987).
Tsiotra et al., *J Biol Chem* 271:29216–29222 (1996).
U.S. Pat. No. 4,244,946
U.S. Pat. No. 4,215,051
U.S. Pat. No. 4,340,535
U.S. Pat. No. 4,472,509
U.S. Pat. No. 5,660,827
U.S. Pat. No. 5,733,876
U.S. Pat. No. 5,753,230
U.S. Pat. No. 5,762,918
U.S. Pat. No. 5,766,591
U.S. Pat. No. 5,776,427
Vaickus et al., *Cancer Invest* 9:195–209 (1991).
Van Heeke et al., *J Biol Chem* 264:5503–5509 (1989).
Vogel & Muller-Eberhard, *Anal. Biochem* 118(2):262–268 (1981).
Wallner et al., *Microsc Res Tech* 39:261–284 (1997).
Wang, Y. and Pallen, C. J., *J Biol Chem* 267:16696–16702 (1992).
Weiss, A. and Schlessinger, J., *Cell* 94:277–280 (1998).
Wigler et al., *Cell* 11:223 (1977).
WO 84/03564
Zimmer et al., *Peptides* (1992) pp. 393–394, ESCOM Science Publishers, B. V., (1993).
Zola, *Monoclonal Antibodies: a Manual of Techniques*, CRC Press, Inc. (1987).

It will be understood that various details of the invention can be changed without departing from the scope of the invention. Furthermore, the foregoing description is for the purpose of illustration only, and not for the purpose of limitation—the invention being defined by the claims.

What is claimed is:

1. An isolated monoclonal antibody, or fragment thereof, which binds to an eight amino acid epitope consisting of the sequence QSRDTEVL (SEQ ID NO: 1) present within amino acids 175–536 of SEQ ID NO: 4, in a diluent or excipient pharmaceutically acceptable in humans.

2. The antibody of claim 1, wherein the monoclonal antibody is monoclonal antibody ECRTPAb-1, produced by a hybridoma cell line having American Type Culture Collection (ATCC) accession number HB12570.

3. The antibody of claim 1, wherein the antibody, or fragment or thereof is human or humanized.

4. An isolated monoclonal antibody having a binding specificity of an antibody produced by a hybridoma cell line having American Type Culture Collection (ATCC) accession number HB12570.

5. A composition comprising a therapeutically effective amount of an isolated monoclonal antibody, or fragment thereof, which specifically binds to an epitope present within amino acids 324–331 of SEQ ID NO: 4 and a diluent or excipient pharmaceutically acceptable in humans, wherein the composition inhibits angiogenesis.

6. The composition of claim 5, wherein the antibody or fragment, or thereof has activity in inhibiting angiogenesis in an assay selected from the group consisting of a planar endothelial migration assay, an in situ transfection assay for migration, a cornea pocket angiogenesis assay, a chick chorioallantoic membrane assay, a proliferation assay, and an endothelial wound closure assay.

7. The composition of claim 5, wherein the fragment is selected from the group consisting of an Fab fragment, an Fab' fragment, an F(ab')2 fragment, an F(v) fragment, and an single chain fragment variable (scFv) fragment.

8. The composition of claim 5, wherein the antibody or fragment thereof is human or humanized.

9. A composition for modulating angiogenesis, the composition comprising:
(a) a therapeutically effective amount of an isolated monoclonal antibody, or fragment thereof, which binds to an eight amino acid epitope consisting of the sequence QSRDTEVL (SEQ ID NO: 1) present within amino acids 175–536 of SEQ ID No: NO: 4., and
(b) a diluent or excipient pharmaceutically acceptable in humans.

10. The composition of claim 9, wherein the antibody, or fragment thereof, is human or humanized.

* * * * *

UNITED STATES PATENT AND TRADEMARK OFFICE
CERTIFICATE OF CORRECTION

PATENT NO. : 7,176,289 B1  Page 1 of 1
APPLICATION NO. : 09/516728
DATED : February 13, 2007
INVENTOR(S) : Daniel et al.

It is certified that error appears in the above-identified patent and that said Letters Patent is hereby corrected as shown below:

Column 71, line 32, replace "wherein the antibody, or fragment or thereof is human or humanized" with --wherein the antibody, or fragment thereof is human or humanized--.

Column 71, line 44, replace "wherein the antibody or fragment, or thereof has activity…" with --wherein the antibody or fragment thereof has activity…--.

Signed and Sealed this

Twenty-fifth Day of December, 2007

JON W. DUDAS
*Director of the United States Patent and Trademark Office*